(12) United States Patent
Krishnan et al.

(10) Patent No.: US 12,171,806 B2
(45) Date of Patent: Dec. 24, 2024

(54) THERAPEUTIC REGIMENS AND METHODS FOR LOWERING BLOOD GLUCOSE AND/OR BODY WEIGHT USING GLP-1R AND GCGR BALANCED AGONISTS

(71) Applicant: Spitfire Pharma LLC, Gaithersburg, MD (US)

(72) Inventors: Vyjayanthi Krishnan, Gaithersburg, MD (US); Joyce James, Gaithersburg, MD (US); Omar Roble Olhaye, Gaithersburg, MD (US); Matthew Scott Harris, Gaithersburg, MD (US)

(73) Assignee: Spitfire Pharma LLC, Gaitehrsburg (MD)

( * ) Notice: Subject to any disclaimer, the term of this patent is extended or adjusted under 35 U.S.C. 154(b) by 224 days.

(21) Appl. No.: 17/544,908

(22) Filed: Dec. 7, 2021

(65) Prior Publication Data

US 2023/0104501 A1   Apr. 6, 2023

Related U.S. Application Data

(60) Provisional application No. 63/249,468, filed on Sep. 28, 2021.

(51) Int. Cl.
| | |
|---|---|
| *A61K 38/26* | (2006.01) |
| *A61K 47/18* | (2017.01) |
| *A61K 47/26* | (2006.01) |
| *A61P 1/16* | (2006.01) |

(Continued)

(52) U.S. Cl.
CPC ............ *A61K 38/26* (2013.01); *A61K 47/183* (2013.01); *A61K 47/26* (2013.01); *A61P 1/16* (2018.01); *A61P 3/04* (2018.01); *A61P 3/10* (2018.01)

(58) Field of Classification Search
CPC ...... A61K 38/26; A61K 47/183; A61K 47/26; A61K 31/7012; A61P 1/16; A61P 3/04; A61P 3/10
See application file for complete search history.

(56) References Cited

U.S. PATENT DOCUMENTS

| | | |
|---|---|---|
| 3,219,656 A | 11/1965 | Boettner |
| 3,839,318 A | 10/1974 | Mansfield |
| 4,179,337 A | 12/1979 | Davis et al. |

(Continued)

FOREIGN PATENT DOCUMENTS

| | | |
|---|---|---|
| AU | 2013347975 B2 | 7/2018 |
| AU | 2015266854 B2 | 3/2020 |

(Continued)

OTHER PUBLICATIONS

Scheen et al., Dual GIP/GLP-1 receptor agonists: New advances for treating type-2 diabetes, 2023, Annales d'Endrocrinologie, 84:316-321 (Year: 2023).*

(Continued)

*Primary Examiner* — James H Alstrum-Acevedo
*Assistant Examiner* — Claudia Espinosa
(74) *Attorney, Agent, or Firm* — Koren Anderson; Duane Morris LLP

(57) ABSTRACT

This disclosure relates to the once weekly dosing regimen of a dual GLP-1R and GCGR agonist, formulations, and methods of using the same for treatment of chronic weight management, obesity and/or blood glucose control, including but not limited to dual agonist peptide product of SEQ ID NO. 1.

19 Claims, 15 Drawing Sheets

Specification includes a Sequence Listing.

(51) Int. Cl.
    *A61P 3/04* (2006.01)
    *A61P 3/10* (2006.01)

(56) References Cited

U.S. PATENT DOCUMENTS

| | | | |
|---|---|---|---|
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,675,189 | A | 6/1987 | Kent et al. |
| 4,791,192 | A | 12/1988 | Nakagawa et al. |
| 5,574,142 | A | 11/1996 | Meyer, Jr. et al. |
| 6,309,633 | B1 | 10/2001 | Ekwuribe et al. |
| 6,720,407 | B1 | 4/2004 | Hughes et al. |
| 6,815,530 | B2 | 11/2004 | Ekwuribe et al. |
| 6,835,802 | B2 | 12/2004 | Ekwuribe et al. |
| 6,864,069 | B2 | 3/2005 | Pan et al. |
| 7,390,788 | B2 | 6/2008 | Pert et al. |
| 7,425,542 | B2 | 9/2008 | Maggio |
| 9,150,652 | B2 | 10/2015 | Theuer et al. |
| 9,178,201 | B2 | 11/2015 | Lee et al. |
| 9,856,306 | B2 | 1/2018 | Nestor |
| 10,005,817 | B2 | 6/2018 | Nestor |
| 10,010,617 | B2 | 7/2018 | Nestor et al. |
| 10,420,844 | B2 | 9/2019 | Nestor et al. |
| 10,471,127 | B2 | 11/2019 | Nestor et al. |
| 10,577,405 | B2 | 3/2020 | Nestor |
| 11,541,028 | B2 | 1/2023 | Nestor |
| 2003/0202981 | A1 | 10/2003 | Kream |
| 2004/0137557 | A1 | 7/2004 | Defrees et al. |
| 2006/0045868 | A1 | 3/2006 | Meezan et al. |
| 2006/0045869 | A1 | 3/2006 | Meezan et al. |
| 2007/0111938 | A1 | 5/2007 | Pert et al. |
| 2008/0200390 | A1 | 8/2008 | Prickett et al. |
| 2008/0227722 | A1 | 9/2008 | Wang |
| 2008/0268032 | A1 | 10/2008 | Maggio |
| 2008/0299079 | A1 | 12/2008 | Maggio et al. |
| 2009/0186819 | A1 | 7/2009 | Carrier et al. |
| 2010/0048462 | A1 | 2/2010 | Ryge et al. |
| 2010/0190701 | A1 | 7/2010 | Day et al. |
| 2011/0257096 | A1 | 10/2011 | Maggio |
| 2012/0290732 | A1 | 11/2012 | Suganthi et al. |
| 2014/0314742 | A1 | 10/2014 | Theuer et al. |
| 2014/0349928 | A1 | 11/2014 | Nestor et al. |
| 2015/0031630 | A1 | 1/2015 | Nestor et al. |
| 2015/0290334 | A1 | 10/2015 | Nestor |
| 2015/0307550 | A1 | 10/2015 | Nestor et al. |
| 2017/0087096 | A1 | 3/2017 | Enherr et al. |
| 2017/0096468 | A1 | 4/2017 | Nestor et al. |
| 2018/0044394 | A1* | 2/2018 | Sensfuss et al. ...... C07K 14/605 |
| 2018/0186853 | A1 | 7/2018 | Kim et al. |
| 2018/0194826 | A1 | 7/2018 | Nestor et al. |
| 2018/0296681 | A1 | 10/2018 | Nestor |
| 2018/0327454 | A1 | 11/2018 | Nestor |
| 2018/0327457 | A1 | 11/2018 | Goel et al. |
| 2019/0161431 | A1 | 5/2019 | Jennings et al. |
| 2020/0277351 | A1 | 9/2020 | Nestor |
| 2020/0289653 | A1 | 9/2020 | Nestor |
| 2020/0352900 | A1 | 11/2020 | Nestor |
| 2021/0077629 | A1 | 3/2021 | Nestor |
| 2021/0290732 | A1* | 9/2021 | Nestor et al. .......... A61K 47/10 |
| 2022/0348611 | A1 | 11/2022 | Nestor |
| 2022/0362345 | A1 | 11/2022 | Nestor |
| 2023/0218564 | A1 | 7/2023 | Nestor |

FOREIGN PATENT DOCUMENTS

| | | | |
|---|---|---|---|
| CA | 2586771 | A1 | 5/2006 |
| CA | 2702289 | A1 | 5/2009 |
| EP | 1767545 | A1 | 3/2007 |
| WO | 9500151 | A1 | 1/1995 |
| WO | 0078302 | A1 | 12/2000 |
| WO | 02098446 | A1 | 12/2002 |
| WO | 2003031464 | A2 | 4/2003 |
| WO | 2004093902 | A1 | 11/2004 |
| WO | 2006064530 | A2 | 6/2006 |
| WO | 2006121860 | A2 | 11/2006 |
| WO | 2007060692 | A2 | 5/2007 |
| WO | 2008052043 | A2 | 5/2008 |
| WO | 2008052043 | A3 | 1/2009 |
| WO | 2009155258 | A2 | 12/2009 |
| WO | 2010151703 | A1 | 12/2010 |
| WO | 2011088837 | A1 | 7/2011 |
| WO | 2011117415 | A1 | 9/2011 |
| WO | 2012088116 | A2 | 6/2012 |
| WO | 2012158962 | A2 | 11/2012 |
| WO | 2012158965 | A2 | 11/2012 |
| WO | 2014081864 | A1 | 5/2014 |
| WO | 2014081872 | A1 | 5/2014 |
| WO | 2014170496 | A1 | 10/2014 |
| WO | WO2015184177 | A1 * | 12/2015 |
| WO | 2016065090 | A1 | 4/2016 |
| WO | 2019136158 | A1 | 7/2019 |
| WO | WO2020109526 | A2 * | 6/2020 |

OTHER PUBLICATIONS

Bass et al. Dual gut hormone receptor agonists for diabetes and obesity, 2023, The Journal of Clinical Investigation, 122(3), pp. 1-5 (Year: 2023).*

Behrendt, R., et al. "Advances in Fmoc solid-phase peptidesynthesis" (2015) J Peptide Sci 22: 4-27.

Clark, M. J. "Prediction of clinical risks by analysis of preclinical and clinical adverse events" Biomed. Inf., 54, Apr. 2015, pp. 167-173).

Day, J, et al., A new glucagon and GLP-1 co-agonist eliminates obesity in rodents. Nat Chem Biol. Oct. 2009;5(10):749-57.

Handbook of Pharmaceutical Excipients, 5th Ed., Rowe et ah, Eds., The Pharmaceutical Press and the American Pharmaceutical Association (2005).

Hedley, A.A., et al. "Prevalence of overweight and obesity among US children, adolescents, and adults, 1999-2002" (2004) JAMA 291: 2847-2850.

International Preliminary report on Patentability dated Aug. 23, 2022; WO/2021/168386.

International Search Report dated Jun. 11, 2021; WO/2021/168386.

Lau J, et al., Discovery of the Once-Weekly Glucagon-Like Peptide-1 (GLP-1) Analogue Semaglutide. J Med Chem. Sep. 24, 2015;58(18):7370-80.

Medical Dictionary for Regulatory Activities (MedDRA) (Pharm., Med. Transl. Med. 2018).

Pharmaceutical Pre-formulation and Formulation, Gibson, Ed., CRC Press (Boca Raton, Florida) (2004).

Santoprete et al., "DPP-IV-resistant, long-acting oxyntomodulin derivatives" Pept. Sci., 17:270-280 (2011).

Wilding, Step 1 Study Group. "Once-Weekly Semaglutide in Adults with Overweight or Obesity." N Engl J Med. Mar. 18, 2021;384(11):989).

Written Opinion of the International Search Committee dated Jun. 11, 2021; WO/2021/168386.

Goldman, M.E., et al., A new highly potent parathyroid hormone antagonist: [D-Trp12,Tyr34]bPTH-(7-34)NH2, Endocrinology, Nov. 1988;123(5):2597-2599.

Gonzalez-Periz, A., et al., Resolution of adipose tissue inflammation, Scientific World Journal, May 4, 2010;10:832-856.

Gopalan, V., et al., Transglucosylation as a probe of the mechanism of action of mammalian cytosolic beta-glucosidase, J Biol Chem, 1992;267(14):9629-9638.

Gourlet, P., et al., "Interaction of lipophilic VIP derivatives with recombinant VIP1/PACAP and VIP2/PACAP receptors", Eur J Pharmacol, Jul. 31, 1998;354(1):105-111.

Greenwald, R.B., et al., Effective drug delivery by PEGylated drug conjugates, Adv Drug Deliv Rev, 2003;55(20):217-250.

Gregoriadis,G., et al., "Polysialic acids: potential in improving the stability and pharmacokinetics of proteins and other therapeutics", Cell Mol Life Sci, Dec. 2000;57(13-14):1964-1969.

Grotenbreg, G.M., et al., "A practical synthesis of gramicidin s and sugar amino Acid containing analogues", J Org Chem, Nov. 12, 2004;69(23):7851-7859.

(56) References Cited

OTHER PUBLICATIONS

Gruner, S.A., et al., "Sugar amino acid containing somatostatin analogues that induce apoptosis in both drug-sensitive and multidrug-resistant tumor cells", Org Lett, Nov. 15, 2001;3(23):3723-3725.
Guo, Z., et al., "Glycopeptide and glycoprotein synthesis involving unprotected carbohydrate building blocks", Med Res Rev., Nov. 2005;25(6):655-678.
Haque, T.S., et al., Exploration of structure-activity relationships at the two C-terminal residues of potent 11mer Glucagon-Like Peptide-1 receptor agonist peptides via parallel synthesis, Peptides, Jul. 2010;31(7):1353-1360.
Haque, T.S., et al., Identification of potent 11mer glucagon-like peptide-1 receptor agonist peptides with novel C-terminal amino acids: Homohomophenylalanine analogs, Peptides, May 2010;31(5):950-955.
Heppner, K.M., et al., Glucagon regulation of energy metabolism, Physiol Behav, Jul. 14, 2010;100(5):545-8.
Hjorth, S.A., et al., Glucagon and glucagon-like peptide 1: selective receptor recognition via distinct peptide epitopes, J Biol Chem, Dec. 2, 1994;269(48):30121-30124.
Hodsman, A.B., et al., "Parathyroid hormone and teriparatide for the treatment of osteoporosis: a review of the evidence and suggested guidelines for its use", Endocr Rev, Aug. 2005;26(5):688-703.
Holtmann, M.H., et al., "Critical contributions of amino-terminal extracellular domains in agonist binding and activation of secretin and vasoactive intestinal polypeptide receptors. Studies of chimeric receptors", J Biol Chem, Jun. 16, 1995;270(24):14394-14398.
Horvat, S., et al., Glycosylation of Lysine-Containing Pentapeptides by Glucuronic Acid: New Insights Into the Maillard Reaction, Carbohydr Res, 2010, 345(3), 377-84.
Jensen, K.J., et al., "Carbohydrates in peptide and protein design", Biopolymers, 2005;80(6):747-761.
Jorgensen, R., et al., Oxyntomodulin differentially affects glucagon-like peptide-1 receptor beta-arrestin recruitment and signaling through Galpha(s), J Pharmacol Exp Ther, Jul. 2007;322(1):148-154.
Kaul, R., et al., "Stereochemical control of peptide folding", Bioorg Med Chem, Jan. 1999;7(1):105-117.
King, H.D., et al., "Monoclonal antibody conjugates of doxorubicin prepared with branched peptide linkers: inhibition of aggregation by methoxytriethyleneglycol chains", J Med Chem, Sep. 12, 2002;45(19):4336-4343.
Koda, Y., et al., "Synthesis and in vitro evaluation of a library of modified endomorphin 1 peptides", Bioorg Med Chem, Jun. 1, 2008;16(11):6286-6296.
Koeltzow, D., et al., Preparation and properties of pure alkyl glucosides, maltosides and maltotriosides, J Am Oil Chem Soc, 1984;61(10):1651-1655.
Kosinski, J.R., et al., The Glucagon Receptor is Involved in Mediating the Body Weight-Lowering Effects of Oxyntomodulin, Obesity, Oct. 17, 2012;20(8):1566-1571.
Law, P.Y., et al., delta-Opioid receptor activates cAMP phosphodiesterase activities in neuroblastoma x glioma NG108-15 hybrid cells, Mol Pharmacol, May 1993;43(5):684-693.
Lazarus, L.H., et al., "Engineering endomorphin drugs: state of the art", Expert Opin Ther Patents, Jan. 2012;22(1):1-14.
Le Chevalier Isaad, A., et al., Side chain-to-side chain cyclization by click reaction, J Peptide, Jul. 2009;15(7):451-454.
Li, Y., et al., Disulfide bond prolongs the half-life of therapeutic peptide-GLP-1, Peptides, Jul. 2011;32(7):1400-1407.
Li, Y.T., et al., Synthesis of neoglycoconjugates using oligosaccharide transferring activity of ceramide glycanase, J Biol Chem, 1991;266(17):10723-10726.
Liebert, et al, "Systemic Absorption of Insulin and Glucagon Applied Topically to the Eyes of Rats and a Diabetic Dog", Journal of Ocular Pharmacology and Therapeutics Volume, (Jan. 1, 1995).
Liu, M., et al., "Parallel solid-phase synthesis of mucin-like glycopeptides", Carbohydr Res, Sep. 26, 2005;340(13):2111-2122.
Lohof, E., et al., "Carbohydrate Derivatives for Use in Drug Design: Cyclic alpha(v)-Selective RGD Peptides", Angew Chem Int Ed Engl, Aug. 4, 2000;39(15):2761-2764.

Lopez, O., et al., Dodecyl maltoside as a solubilizing agent of stratum corneum lipid liposomes, Colloid Polym Sci, 2002;280:352-357.
Lowery, J.J., "In Vivo Characterization of MMP-2200, a Mixed δ/μ Opioid Agonist, in Mice", J Pharmacol Exp Ther, Mar. 2011;336(3):767-778.
Luck, M.D., et al., "The (1-14) fragment of parathyroid hormone (PTH) activates intact and amino-terminally truncated PTH-1 receptors", Mol Endocrinol, May 1999;13(5):670-680.
Mack, C.M., et al., Antiobesity action of peripheral exenatide (exendin-4) in rodents: effects on food intake, body weight, metabolic status and side-effect measures, Int J Obes (Lond), Sep. 2006;30(9):1332-1340.
Mahaffey, J.E., et al., Parathyroid hormone inhibitors. Determination of minimum sequence requirements, J Biol Chem, Jul. 25, 1979;254(14):6496-6498.
Maji, S.K., et al., "Amyloid as a depot for the formulation of long-acting drugs", PLoS Biol, Feb. 2008;6(2):e17.
Mandal, T.K., Inhaled insulin for diabetes mellitus, Am J Health Syst Pharm, Jul. 1, 2005;62(13):1359-1364.
Mapelli, C., et al., Eleven amino acid glucagon-like peptide-1 receptor agonists with antidiabetic activity, J Med Chem, Dec. 10, 2009;52(23):7788-7799.
Marx, U.C., et al., Structure of human parathyroid hormone 1-37 in solution, J Biol Chem, Jun. 23, 1995;270(25):15194-15202.
Melchiorri, P., et al., "The dermorphin peptide family", Gen Pharmacol, Oct. 1996;27(7):1099-1107.
Mero, A., et al., Synthesis and characterization of poly(2-ethyl 2-oxazoline)-conjugates with proteins and drugs: suitable alternatives to PEG-conjugates?, J Control Release, Jan. 22, 2008; 125(2):87-95.
Milkereit, G., et al., Thermotropic and lyotropic properties of long chain alkyl glycopyranosides: part III: pH-sensitive headgroups, Chem Phys Lipids, Jan. 2004;127(1):47-63.
Miller, M.A., et al., Amphiphilic conjugates of human brain natriuretic peptide designed for oral delivery: in vitro activity screening, Bioconjug Chem, 2006;17(2):267-274.
Miranda, L., et al., Design and Synthesis of Conformationally Constrained Glucagon-Like Peptide-1 Derivatives with Increased Plasma Stability and Prolonged in Vivo Activity, J Med Chem, 2008;51:2758-2765.
Moon et al., "Evolutionary Conserved Residues at Glucagon-like peptide-1 (GLP-1) Receptor Core Confer Ligand-induced receptor activation." The American Society for Biochemistry and Molecular Biology, 2012. Journal of Biological Chemistry vol. 287, No. 6, p. 3873-3884.
Murage, E.N., Development of potent glucagon-like peptide-1 agonists with high enzyme stability via introduction of multiple lactam bridges, J Med Chem, Sep. 9, 2010;53(17):6412-6420.
Murage, E.N., et al., Search for alpha-helical propensity in the receptor-bound conformation of glucagon-like peptide-1, Bioorg Med Chem, Dec. 1, 2008;16(23):10106-10112.
Negri, L., et al., "Dermorphin and deltorphin glycosylated analogues: synthesis and antinociceptive activity after systemic administration", J Med Chem, Feb. 11, 1999;42(3):400-404.
Australian Patent Application No. 2012255116 Patent Examination Report No. 1 dated Jun. 14, 2016.
BACHEM compound H-8865. 1 page. Downloaded Aug. 23, 2017 from: http://shop.bachem.com/h-8865.html.
Bryant, S., et al. Dmt and opioid peptides: a potent alliance. Biopolymers. 2003;71(2):86-102.
Chinese Patent Application No. 201280035528.1 Second Office Action dated Sep. 9, 2015 (English translation).
Chinese Patent Application No. 201280035629.9 Third Office Action dated Aug. 16, 2016.
Constantino L., et al., Peptide-derivatized biodegradable nanoparticles able to cross the blood-brain barrier. Journal of Controlled Release, Nov. 2, 2005;108(1):84-96.
Database—UniProtKB, accession No. P68955 (GLUC_TRASC), last sequence update: Jul. 21, 1986.
Egleton, R., et al., Development of neuropeptide drugs that cross the blood-brain barrier. The Journal of the American Society for Experimental Neuro Therapeutics, Jan. 2005;2:44-53.

(56) References Cited

OTHER PUBLICATIONS

EP12784971.1 Suppl European Search Report dated Jan. 21, 2015.
EP12784971.9 Extended European Search Report dated Jan. 12, 2015.
EP12785861.1 Extended European Search Report dated Sep. 12, 2014.
European Patent Application No. 12784971.9 Communication dated Sep. 20, 2016.
European Patent Application No. 12784971.9 Supplementary European Search Report dated Jan. 21, 2015.
European Patent Application No. 12785861.1 Extended European Search Report dated Sep. 12, 2014.
European Patent Application No. 13856357.2 Extended European Search Report dated May 2, 2016.
European Patent Application No. 13857269.8 extended European Search Report dated Apr. 29, 2016.
Farkas et al. Chemical conjugation of biomacromolecules: A mini-review. Chemical Papers. 2010; 64 (6):683-695.
Ferguson, M.A., et al. Glycosyl-phosphatidylinositol moiety that anchors Trypanosoma brucei variant surface glycoprotein to the membrane, Science, Feb. 12, 1988;239(4841 Pt 1):753-9.
Japanese Patent Application No. 2014-511554 Decision of Rejection dated Oct. 19, 2016.
Kalyuzhin, O.V., et al., Biological activity of anomeric pairs of lipophilic glycosides of N-Acetylmuramyl-L-Alanyl-D-Isoglutamine. Bulletin of Experimental Biology and Medicine, 2008;145(5):623-625.
Lichtenthaler, "Carbohydrates as Organic Raw Materials", VCH Publishers, (19910000) 2010.
Lindhout, Theresia et al, "Site specific enzymatic polysialylation of therapeutic proteins using bacterial enzymes." PNAS (2011) 108(18) p. 7397-7402.
Matsumoto, et al., Stimulation of nonspecific resistance to infection induced by muramyl dipeptide analogs substituted in the gamma-carboxyl group and evaluation of N alpha-muramyl dipeptide-N epsilon-stearoyllysine, Infect Immun, 1983;39(3):1029-40.
Mexican Patent Application No. MX/a/2013/013395 first Office Action dated Aug. 26, 2016 (in Spanish), with reporting letter from the foreign associate (in English).
Minden, H.M. et al., "Thermotropic and lyotropic properties of long chain alkyl glycopyranosides. Part II. Disaccharide headgroups." Chem Phys Lipids, (20000000), vol. 106, pp. 157-179.
NCBI Gen Bank accession No. 1DOR A, Oct. 10, 2012, "Chain A, Dihydroorotate Dehydrogenase A From Lactococcus Lactis" downloaded Aug. 18, 2020, 3 pages.
Nonyl beta-D-glucopyranoside (PubChem CID 155448). http://pubchem.ncbi.nlm.nih.gov/compound/155448. downloaded Jan. 12, 2016. (Year: 2016).
Nonyl beta-D-glucopyranoside chemical structure. PubChem Compound Summary for CID 155448. 17 pages, printed Jan. 12, 2016.
Park, et al., "Mucosal immunity induced by adenovirus-based H5N1 HPAI vaccine confers protection against a lethal H5N2 avian influenza virus challenge," Virology, 2009, 395:182-189.
Paulick and Bertozzi, The Glycosylphosphatidylinositol anchor: A complex membrane-anchoring structure for proteins Biochemistry, 47:6991-7000 (2008).
Paulick, M.G., et al. The glycosylphosphatidylinositol anchor: a complex membrane-anchoring structure for proteins, Biochemistry, Jul. 8, 2008;47(27):6991-7000.
PCT Patent Application No. PCT/US2012/038429 International Preliminary Report on Patentability dated Nov. 19, 2013.
PCT Patent Application No. PCT/US2012/038429 Written Opinion of the International Searching Authority dated Mar. 28, 2013.
PCT Patent Application No. PCT/US2012/038433 International Preliminary Report on Patentability dated Nov. 19, 2013.
PCT Patent Application No. PCT/US2012/038433 International Search Report dated Oct. 29, 2012.
PCT Patent Application No. PCT/US2012/038433 Written Opinion dated Oct. 29, 2012.
PCT Patent Application No. PCT/US2012/038434 International Preliminary Report on Patentability dated Nov. 19, 2013.
Van Bekkum, H., Carbohydrates as Organic Raw Materials, 1990, 289-310.
Van Den Bos, L.J., et al., Uronic Acids in Oligosaccharide Synthesis, Eur J Org Chem, 2007;(24):3963-3976.
Veronese, F.M., et al., PEGylation, successful approach to drug delivery, Drug Discov Today, Nov. 1, 2005;10(21):1451-1458.
Veronese, F.M., et al., The impact of PEGylation on biological therapies, BioDrugs, 2008;22(5):315-329.
Vill, V. et al., Thermotropic and lyotropic properties of long chain alkyl glycopyranosides. Part I: monosaccharide headgroups, Chem Phys Lipids, 2000;104(1):75-91.
Von Minden, H.M., et al., Thermotropic and lyotropic properties of long chain alkyl glycopyranosides. Part II. Disaccharide headgroups, Chem Phys Lipids, 2000;106(2):157-179.
Wang, J.B., et al., Human mu opiate receptor. cDNA and genomic clones, pharmacologic characterization and chromosomal assignment, FEBS Lett, Jan. 31, 1994;338(2):217-222.
Whitfield, J.F., et al., "Small bone-building fragments of parathyroid hormone: new therapeutic agents for osteoporosis", Trends Pharmacol Sci, Nov. 1995;16(11):382-386.
Wynne, K., et al., Subcutaneous oxyntomodulin reduces body weight in overweight and obese subjects: a double-blind, randomized, controlled trial, Diabetes, Aug. 2005;54(8):2390-2395.
Yamamoto, T., et al., Improving metabolic stability by glycosylation: bifunctional peptide derivatives that are opioid receptor agonists and neurokinin 1 receptor antagonists, J Med Chem, Aug. 27, 2009;52(16):5164-5175.
Zhou, B, et al., Small Surfactant-like peptides can drive soluble proteins into active aggregates, Microbial Cell Factories, Epub, Jan. 2012, vol. 11, No. 10, pp. 1-8.
European Patent Application No. 15798956.7 European Search Opinion dated Feb. 22, 2019.
PCT Patent Application No. PCT/US2012/038434 Written Opinion dated Nov. 9, 2012.
PCT Patent Application No. PCT/US2013/071067 International Preliminary Report on Patentability dated Jun. 4, 2015.
PCT Patent Application No. PCT/US2013/071067 International Search Report dated Feb. 25, 2014.
PCT Patent Application No. PCT/US2013/071077 International Preliminary Report on Patentability dated Jun. 4, 2015.
PCT Patent Application No. PCT/US2013/071077 International Search Report dated Mar. 14, 2014.
PCT Patent Application No. PCT/US2015/033042 International Search Report mailed Aug. 25, 2015.
PCT/US2012/038429 International Preliminary Report on Patentability dated Nov. 19, 2013.
PCT/US2012/038429 International Search Report and Written Opinion dated Mar. 28, 2013.
PCT/US2012/038434 International Search Report and Written Opinion dated Nov. 9, 2012.
PCT/US2013/071067 International Preliminary Report on Patentability dated Jun. 4, 2015.
PCT/US2013/071067 International Search Report dated Feb. 25, 2014.
PCT/US2013/071077 International Preliminary Report on Patentability dated Jun. 4, 2015.
PCT/US2013/071077 International Search Report dated Mar. 14, 2014.
PCT/US2015/033042 International Search Report and Written Opinion dated Aug. 25, 2015.
Pillion et al., Systemic absorption of insulin and glucagon applied topically to the eyes of rats and a diabetic dog. Journal of Ocular Pharmacology and Therapeutics, 11(3):13 pages, 1995.
Product Block n-Dodecyl-B-D-maltoside / CAS 69227-93-6 / Santa Cruz Biotech 2 pages, 2007.
PubChemCompound, datasheet [online compound summary] retrieved from the Internet: Oct. 27, 2006; See CID 11600623, 9 pages.
PubChemCompound, datasheet [online compound summary] retrieved from the Internet: Oct. 27, 2006; See CID 11708016, 9 pages.
Pure Applied Chemistry A one-letter notation for amino acid sequences (definitive rules) vol. 31, pp. 639-645.

(56) References Cited

OTHER PUBLICATIONS

Ribosa, I., et al., Solubilization of Large Unilamellar Liposomes by Alkyl Glycosides. J Colloid Interface Sci, Mar. 15, 1997;187(2):443-6.
RN 115414-60-3, Task History. Task began Aug. 31, 2016, 02:16 PM. Explore substances by Substructure ID(1). 4 pages.
Santa Cruz Biotechnology Product. n-Dodecyl-p-D-maltoside. http://www.scbt.com/datasheet-281071.html downloaded Dec. 28, 2015. (Year: 2015).
Santonicola, M., et al., "Binding of alkyl polyglucoside surfactants to bacteriorhodopsin and its relation to protein stability", Biophys J, 2008;94(9):3647-3658.
Sasaki, K., et al., X-ray analysis of glucagon and its relationship to receptor binding, Nature, Oct. 30, 1975;257(5529):751-757.
Saurer, et al., Neuroimmune mechanisms of opioid-mediated conditioned immunomodulation. Brain Behav Immun. Jan. 2008; 22(1): 89-97.
Savic et al., From conventional towards new-natural surfactants in drug delivery systems design: current status and perspectives. Expert Opinion on Drug Delivery, 7(3):353-369, 2010.
Suhara, Y., et al., Peptide-sugar hybrids: Like peptide, like oligosaccharide, Tetrahedron Letters, 1997;38(41):7167-7170.
U.S. Appl. No. 14/118,546 Office Action dated Aug. 14, 2015.
U.S. Appl. No. 14/118,546 Office Action dated Jan. 17, 2017.
U.S. Appl. No. 14/118,546 Office Action dated Jan. 29, 2016.
U.S. Appl. No. 14/118,546 Office Action dated Sep. 6, 2017.
U.S. Appl. No. 14/118,546 Office Action dated Sep. 9, 2016.
U.S. Appl. No. 14/646,246 Office Action dated Dec. 15, 2015.
U.S. Appl. No. 14/646,246 Office Action dated Feb. 7, 2017.
U.S. Appl. No. 14/646,246 Office Action dated Mar. 25, 2016.
U.S. Appl. No. 14/646,246 Office Action dated Sep. 22, 2016.
U.S. Appl. No. 14/646,246 Office Action dated Sep. 6, 2017.
U.S. Appl. No. 14/646,246 Restriction Requirement dated Dec. 15, 2015.
Ueda, et al., "Chemoenzymatic Synthesis of Glycosylated Glucagon-like Peptide 1: Effect of Glycosylation on Proteolytic Resistance and in Vivo Blood Glucose-Lowering Activity," J. Am. Chem. Soc. 2009;131(17): 6237-6245.
Vill, V. et al., Chem Phys Lipids, (20000000), vol. 104, pp. 75-91.
Vinke. Oxidation of carbohydrates and derivatives using carbon supported noble metal catalysts Dissertation, 1981, 156 pages.
Bhattacharya,A, Crystallographic Analysis Reveals Common Modes of Binding of Medium and Long-chain Fatty Acids to Human Serum Albumin. J. Mol. Biol. (2000) 303, 721-732.
Abbenante, G., et al., Protease inhibitors in the clinic, Med Chem, Jan. 2005;1(1):71-104.
Adelhorst, K., et al., Structure-activity studies of glucagon-like peptide-1, J Biol Chem, Mar. 4, 1994;269(9):6275-6278.
Ahsan, F., et al., Enhanced bioavailability of calcitonin formulated with alkylglycosides following nasal and ocular administration in rats, Pharm Res, Dec. 2001;18(12):1742-1746.
Akiyama, K., et al., "Characterization of [3H][2-D-penicillamine, 5-D-penicillamine]-enkephalin binding to delta opiate receptors in the rat brain and neuroblastoma—glioma hybrid cell line (NG 108-15)", PNAS USA, Apr. 1985;82(8):2543-7.
Andya, J.D. et al., Pharm Res, (19990000), vol. 16, pp. 350-358.
Arakawa, T., et al., Stabilization of protein structure by sugars, Biochemistry, Dec. 7, 1982;21(25):6536-6544.
Arakawa, T., et al., The stabilization of proteins by osmolytes, Biophys J, Mar. 1985;47(3):411-414.
Avidor-Reiss, T., et al., kappa-Opioid receptor-transfected cell lines: modulation of adenylyl cyclase activity following acute and chronic opioid treatments, FEBS Lett, Mar. 13, 1995;361(1):70-74.
Barazza, A., et al., "Bioactive N-terminal undecapeptides derived from parathyroid hormone: the role of alpha-helicity", J Pept Res, Jan. 2005;65(1):23-35.
Bergwitz, C., et al., "Full activation of chimeric receptors by hybrids between parathyroid hormone and calcitonin. Evidence for a common pattern of ligand-receptor interaction", J Biol Chem, Oct. 25, 1996;271(43):26469-26472.

Biondi, L., et al., "Novel glycosylated [Lys(7)]-dermorphin analogues: synthesis, biological activity and conformational investigations", J Pept Sci, 2007;13(3):179-189.
Boyce, B.F., et al., "Biology of RANK, RANKL, and osteoprotegerin", Arthritis Res Ther, 2007;9(Suppl 1):S1.
Brixen, K.T., et al., Teriparatide (biosynthetic human parathyroid hormone 1-34): a new paradigm in the treatment of osteoporosis, Basic Clin Pharmacol Toxicol, Jun. 2004;94(6):260-270.
Buse, J.B., et al., DURATION-1: exenatide once weekly produces sustained glycemic control and weight loss over 52 weeks, Diabetes Care, 2010;33:1255-1261.
Caliceti, P., et al., Pharmacokinetic and biodistribution properties of poly(ethylene glycol)-protein conjugates, Adv Drug Deliv Rev, 2003;55(10):1261-1277.
Casadevall, N., et al., "Pure red-cell aplasia and antierythropoietin antibodies in patients treated with recombinant erythropoietin", N Engl J Med, Feb. 14, 2002;346(7):469-475.
Chakraborty, T.K., et al., "Sugar amino acids in designing new molecules", Glycoconj J, Mar. 2005;22(3):83-93.
Cheng, Z., et al., "Prolonged treatments with antiresorptive agents and PTH have different effects on bone strength and the degree of mineralization in old estrogen-deficient osteoporotic rats", J Bone Miner Res, Feb. 2009;24(2):209-220.
Chicchi, G.G., et al., Alterations in receptor activation and divalent cation activation of agonist binding by deletion of intracellular domains of the glucagon receptor, J Biol Chem, Mar. 21, 1997;272(12):7765-7769.
China Patent Application No. 201580041790.0; First Office Action (in Chinese) and translation (English) dated Jun. 28, 2019.
Clodfelter,D.K., et al., "Effects of non-covalent self-association on the subcutaneous absorption of a therapeutic peptide", Pharm Res, Feb. 1998;15(2):254-262.
Codee, J.D., et al., A modular strategy toward the synthesis of heparin-like oligosaccharides using monomeric building blocks in a sequential glycosylation strategy, J Am Chem Soc, Mar. 23, 2005;127(11):3767-3773.
Cohen, M.A., et al., Oxyntomodulin suppresses appetite and reduces food intake in humans, J Clin Endocrinol Metab, Oct. 2003;88(10):4696-4701.
Condon, S.M., et al., "Analogues of human parathyroid hormone (1-31)NH(2): further evaluation of the effect of conformational constraint on biological activity", Bioorg Med Chem, Mar. 2002;10(3):731-736.
Dakin, C.L., et al., Peripheral oxyntomodulin reduces food intake and body weight gain in rats, Endocrinology, Jun. 2004;145(6):2687-2695.
Davidson, M.H., et al., Cardiovascular effects of glucagonlike peptide-1 agonists, Am J Cardiol, Aug. 2, 2011;108(3 Suppl):33B-41B.
De Graaf, A.J., et al., Nonnatural amino acids for site-specific protein conjugation, Bioconjug Chem, Jul. 2009;20(7):1281-1295.
De Mico, A., et al., A Versatile and Highly Selective Hypervalent Iodine (III)/2,2,6,6-Tetramethyl-1-piperidinyloxyl-Mediated Oxidation of Alcohols to Carbonyl Compounds, J Org Chem, 1997;62(20):6974-6977.
Deacon, et al., "Dipeptidyl peptidase IV resistant analogues of glucagon-like peptide-1 which have extended metabolic stability and improved biological activity", Diabetologia, 1998;41(3):271-278.
Dean, T., et al., "Role of amino acid side chains in region 17-31 of parathyroid hormone (PTH) in binding to the PTH receptor", J Biol Chem, Oct. 27, 2006;281(43):32485-32495.
Defronzo, R.A., et al., Effects of exenatide (exendin-4) on glycemic control and weight over 30 weeks in metformin-treated patients with type 2 diabetes, Diabetes Care, May 2005, 28(5);1092-1100.
Deiters, A., et al., Site-specific PEGylation of proteins containing unnatural amino acids, Bioorg Med Chem Lett, Dec. 6, 2004;14(23):5743-5745.
Drab, S.R., Incretin-based therapies for type 2 diabetes mellitus: current status and future prospects, Pharmacotherapy, Jun. 2010;30(6):609-624.

(56) References Cited

OTHER PUBLICATIONS

Drouillat, B., et al., Solid phase synthesis of C-terminal carbohydrate modified enkephalins, Bioorg Med Chem Letters, Sep. 9, 1997;7(17):2247-2250.

Druce, M.R., et al., Investigation of structure-activity relationships of Oxyntomodulin (Oxm) using Oxm analogs, Endocrinology, Apr. 2009;150(4):1712-1722.

Elofsson, M., et al., Preparation of Tn and sialyl Tn building blocks used in Fmoc solid-phase synthesis of glycopeptide fragments from HIV gp120, Tetrahedron, 1997;53(1):369-390.

Epp, J.B., et al., Facile Preparation of Nucleoside-5'-carboxylic Acids, J Org Chem, Jan. 8, 1999;64(1):293-295.

Erspamer, V., et al., "Deltorphins: a family of naturally occurring peptides with high affinity and selectivity for delta opioid binding sites", PNAS USA. Jul. 1989;86(13):5188-92.

Etoh, M., et al., Repetition of continuous PTH treatments followed by periodic withdrawals exerts anabolic effects on rat bone, J Bone Miner Metab, Nov. 2010;28(6):641-649.

Ferenci, T., Methyl-alpha-maltoside and 5-thiomaltose: analogs transported by the *Escherichia coli* maltose transport system, J Bacteriol, 1980;144(1):7-11.

Filira, F., et al., Opioid peptides: synthesis and biological properties of [(N gamma-glucosyl,N gamma-methoxy)-alpha, gamma-diamino-(S)-butanoyl]4-deltorphin-1-neoglycopeptide and related analogues, Org Biomol Chem, Sep. 7, 2003;1(17):3059-3063.

Frolik, C.A., "Anabolic and catabolic bone effects of human parathyroid hormone (1-34) are predicted by duration of hormone exposure", Bone, Sep. 2003;33(3):372-379.

Gardella, T.J, et al., Inverse agonism of amino-terminally truncated parathyroid hormone (PTH) and PTH-related peptide (PTHrP) analogs revealed with constitutively active mutant PTH/PTHrP receptors, Endocrinology, Sep. 1996;137(9):3936-3941.

Gauthier, M.A., et al., Peptide/protein-polymer conjugates: synthetic strategies and design concepts, Chem Commun, Jun. 21, 2008;(23):2591-2611.

Geary, N., et al., Individual, but not simultaneous, glucagon and cholecystokinin infusions inhibit feeding in men, Am J Physiol, Jun. 1992;262(6 Pt 2):R975-980.

Gejl, M., et al., Exenatide alters myocardial glucose transport and uptake depending on insulin resistance and increases myocardial blood flow in patients with type 2 diabetes, J Clin Endocrinol Metab, Jul. 2012;97(7):E1165-9.

Gijsen, H.J., et al., "Recent Advances in the Chemoenzymatic Synthesis of Carbohydrates and Carbohydrate Mimetics", Chem Rev, Feb. 1, 1996;96(1):443-474.

Negri, L., et al., "Glycodermorphins: opioid peptides with potent and prolonged analgesic activity and enhanced blood-brain barrier penetration", Br J Pharmacol, Aug. 1998;124(7):1516-1522.

Nestor et al., "Design and Characterization of a surfactant-conjugated, long-acting, balanced GLP-1/glucagon receptor dual agonist." Peptide Science, 2021;113:e24221.

New Zealand Application No. 726623; First examination report dated Feb. 13, 2019.

Park, D.W., et al., Enzymatic synthesis of alkylglucosides by amphiphilic phase enzyme reaction, Biotechnology Letters, Jun. 2000;22(11):951-956.

Payne, R.J., et al., "Extended sugar-assisted glycopeptide ligations: development, scope, and applications", J Am Chem Soc, Nov. 7, 2007;129(44):13527-13536.

PCT Patent Application No. PCT/US2012/038429 International Search Report dated Mar. 28, 2013.

PCT Patent Application No. PCT/US2012/038434 International Search Report dated Nov. 9, 2012.

PCT Patent Application No. PCT/US2015/033042 Written Opinion mailed Aug. 25, 2015.

Pean, C., et al., "Pharmacological in vitro evaluation of new substance P-cyclodextrin derivatives designed to drug targeting towards NK1-receptor bearing cells", Biochim Biophys Acta, Dec. 19, 2001;1541(3):150-160.

Pedersen, S.L., Glyco-scan: varying glycosylation in the sequence of the peptide hormone PYY3-36 and its effect on receptor selectivity, Chembiochem, Feb. 15, 2010;11(3):366-374.

Peleg-Shulman, T., et al., Reversible PEGylation: a novel technology to release native interferon alpha2 over a prolonged time period, J Med Chem, 2004;47(20):4897-4904.

Pioszak, A.A., et al., "Molecular recognition of parathyroid hormone by its G protein-coupled receptor", PNAS USA, Apr. 1, 2008;105(13):5034-5039.

Pioszak, A.A., et al., "Structural basis for parathyroid hormone-related protein binding to the parathyroid hormone receptor and design of conformation-selective peptides", J Biol Chem, Oct. 9, 2009;284(4):28382-391.

Pocai, A., et al., Glucagon-like peptide 1/glucagon receptor dual agonism reverses obesity in mice, Diabetes, Oct. 2009;58(10):2258-2266.

Potetinova, Z., et al., "C-terminal analogues of parathyroid hormone: effect of C-terminus function on helical structure, stability, and bioactivity", Biochemistry, Sep. 19, 2006;45(37):11113-11121.

Rattan, S.I., et al., Protein synthesis, posttranslational modifications, and aging, Ann NY Acad Sci, 1992;663:48-62.

Reeve, J., et al., "Anabolic effect of human parathyroid hormone fragment on trabecular bone in involutional osteoporosis: a multicentre trial", Br Med J, Jun. 7, 1980;280(6228):1340-1344.

Roberts, M.J., et al., Chemistry for peptide and protein PEGylation, Adv Drug Deliv Rev, Jun. 17, 2002;54(4):459-476.

Roccatano, D., et al., "Mechanism by which 2,2,2-trifluoroethanol/water mixtures stabilize secondary-structure formation in peptides: a molecular dynamics study", PNAS USA, Sep. 17, 2002;99(19):12179-12184.

Rosen, C.J., et al., "Clinical review 123: Anabolic therapy for osteoporosis", J Clin Endocrinol Metab, Mar. 2001;86(3):957-964.

Rosevear, P., et al., Alkyl glycoside detergents: a simpler synthesis and their effects on kinetic and physical properties of cytochrome c oxidase, Biochemistry, 1980;19(17):4108-4115.

Runge, S., et al., Three distinct epitopes on the extracellular face of the glucagon receptor determine specificity for the glucagon amino terminus, J Biol Chem, Jul. 25, 2003;278(30):28005-28010.

Runge, S., et al., Crystal structure of the ligand-bound glucagon-like peptide-1 receptor extracellular domain, J Biol Chem, Apr. 25, 2008;283(17):11340-11347.

Runge, S., et al., Different domains of the glucagon and glucagon-like peptide-1 receptors provide the critical determinants of ligand selectivity, Br J Pharmacol, Mar. 2003;138(5):787-794.

Saito, S., et al., Synthesis of Alkyl-β-D-thioglucopyranosides, a Series of New Nonionic Detergents, Chem Pharm Bull, 1985;33(2):503-508.

Salvador, L.A., et al., "Preparation of building blocks for glycopeptide synthesis by glycosylation of Fmoc amino acids having unprotected carboxyl groups", Tetrahedron, May 8, 1995;51(19):5643-5656.

Sanger, G.J., et al., Hormones of the gut-brain axis as targets for the treatment of upper gastrointestinal disorders, Nat Rev Drug Discov, Mar. 2008;7(3):241-254.

Sato, S., et al., Prevention of insulin self-association and surface adsorption, J Pharm Sci, Mar. 1983;72(3):228-232.

Schamann, M., et al., TEMPO-Mediated Anodic Oxidation of Methyl Glycosides and 1-Methyl and1-Azido Disaccharides, Eur J Org Chem, 2003:351-358.

Schievano, E., et al., "Conformational studies of parathyroid hormone (PTH)/PTH-related protein (PTHrp) chimeric peptides", Biopolymers, Nov. 2000;54(6):429-447.

Schiller, P.W., Bi- or multifunctional opioid peptide drugs, Life Sci, Apr. 10, 2010;86(15-16):598-603.

Schiller, P.W., Opioid peptide-derived analgesics, AAPS J, Oct. 14, 2005;7(3):E560-565.

Schiller, P.W., The TIPP opioid peptide family: development of delta antagonists, delta agonists, and mixed mu agonist/delta antagonists, Biopolymers, 1999;51(6):411-425.

Sears, P., et al., "Enzyme action in glycoprotein synthesis", Cell Mol Life Sci, Mar. 1998;54(3):223-252.

Shenoy, SK., et all, β-Arrestin-mediated Receptor Trafficking and Signal Transduction, Trends Pharmacol Sci, 2011, 32(9), 521-533.

(56) References Cited

OTHER PUBLICATIONS

Shimizu, M., et al., "Minimization of parathyroid hormone. Novel amino-terminal parathyroid hormone fragments with enhanced potency in activating the type-1 parathyroid hormone receptor", J Biol Chem, Jul. 21, 2000;275(29):21836-21843.

Shimizu, N., et al., "Amino-terminal parathyroid hormone fragment analogs containing alpha,alpha-di-alkyl amino acids at positions 1 and 3", J Bone Miner Res, Dec. 2004;19(12):2078-2086.

Shimizu, N., et al., "Parathyroid hormone (PTH)-(1-14) and -(1-11) analogs conformationally constrained by alpha-aminoisobutyric acid mediate full agonist responses via the juxtamembrane region of the PTH-1 receptor", J Biol Chem, Dec. 28, 2001;276(52):49003-49012.

Sluzky, V., et al., "Kinetics of insulin aggregation in aqueous solutions upon agitation in the presence of hydrophobic surfaces", PNAS USA, Nov. 1, 1991;88(21):9377-9381.

Smits, E., et al., Reliable method for the synthesis of aryl β-D-glucopyranosides, using boron trifluoride-diethyl ether as catalyst, J Chem Soc, Perkin Trans 1, 1996;2873-2877.

Smits, E., et al., Thermotropic and lyotropic liquid crystalline behaviour of 4-alkoxyphenyl beta-D-glucopyranosides, Liquid Crystals, 1997;23(4):481-488.

Sokos, G.G., et al., Glucagon-like peptide-1 infusion improves left ventricular ejection fraction and functional status in patients with chronic heart failure, J Card Fail, Dec. 2006;12(9):694-699.

Son, S., et al., Preparation and Structural, Biochemical, and Pharmaceutical Characterizations of Bile Acid-Modified Long-Acting Exendin-4 Derivatives, J Medical Chem, 2009;52:6889-6896.

Stein, C., et al., Peripheral mechanisms of pain and analgesia, Brain Res Rev, Apr. 2009;60(1):90-113.

Stevenson, C.L., Advances in peptide pharmaceuticals, Curr Pharm Biotechnol, Jan. 2009;10(1):122-137.

Tashjian, A.H., et al., "On the interpretation of rat carcinogenicity studies for human PTH(1-34) and human PTH (1-84)", J Bone Miner Res, Jun. 2008;23(6):803-811.

Thurow, Stabilisation of dissolved proteins against denaturation at hydrophobic interfaces, Diabetologia, Aug. 1984;27(2):212-218.

Tyndall, J.D., et al., Over one hundred peptide-activated G protein-coupled receptors recognize ligands with turn structure, Chem Rev, Mar. 2005;105(3):793-826.

U.S. Appl. No. 14/118,545 Restriction Requirement dated Sep. 5, 2018.

Underwood et al., "Crystal structure of Glucagon-like Peptide-1 in Complex with Extracellular Domain of the Glucagon-like Peptide-1 Receptor." Journal of Biological Chemistry vol. 285 No. 1 p. 723-730. 2010.

\* cited by examiner

Figure 14

| Characteristic | | 1.5 mg | 15 mg | 3.0 mg | Pooled Placebo |
|---|---|---|---|---|---|
| Weight Loss | | | | | |
| BMI Baseline (cm) | mean (SD) | 30.03 (3.9) | 30.09 (3.9) | 31.75 (2.9) | 30.96 (4.3) |
| BMI Day 85 (cm) | Mean (SD) | 29.08 (3.8) | 26.99 (3.6) | 29.33 (3.1) | 30.32 (4.5) |
| % lost compared to baseline | mean (SD) | -4.93 (3) | -10.28 (3.4)* | -8.98 (3.4)* | -1.64 (3.1) |

Figure 15

| Characteristic | | 2.4mg | 1.2mg | 2.4mg (Titration) | Placebo |
|---|---|---|---|---|---|
| Weight Loss | | | | | |
| early satiety | n(%) | 0 | 0 | 1 (9.1) | 0 |
| decreased appetite | n(%) | 1 (14.3%) | 5 (55.6%) | 7 (63.6%) | 2 (28.6%) |

THERAPEUTIC REGIMENS AND METHODS FOR LOWERING BLOOD GLUCOSE AND/OR BODY WEIGHT USING GLP-1R AND GCGR BALANCED AGONISTS

RELATED APPLICATIONS

This application claims priority to provisional application Nos. U.S. Ser. No. 63/122,117 filed 7 Dec. 2020; U.S. Ser. No. 63/211,157 filed 16 Jun. 2021; and, U.S. Ser. No. 63/249,468 filed 28 Sep. 2021 each of which are hereby incorporated into this application in their entirety.

SEQUENCE LISTING

The instant application contains a Sequence Listing which has been submitted electronically in ASCII format via EFS-Web and hereby incorporated by reference in its entirety. Said ASCII copy, created on 7 Dec. 2021, is named MED008US1_ST25.TXT and is 12,288 bytes in size.

FIELD OF THE DISCLOSURE

This disclosure relates to the field of GLP-1R and GCGR agonists, formulations, and methods of using the same.

BACKGROUND OF THE DISCLOSURE

The increasing prevalence of obesity, diabetes mellitus, non-alcoholic fatty liver disease (NAFLD) and its advanced form, non-alcoholic steatohepatitis (NASH), is a world health crisis of epidemic proportions that is a major contributor to patient morbidity and mortality as well as a major economic burden. Obesity is an important risk factor for type 2 diabetes and NASH, and roughly 90% of patients with type 2 diabetes are overweight or obese. Obesity is a rapidly increasing problem worldwide and currently more than 65% of adults in the U.S. are overweight (Hedley, A. A., et al. (2004) JAMA 291: 2847-2850). NASH is anticipated to be the leading cause of liver transplant in the near future. There is a need for development of safe and efficacious pharmaceutical treatments for obesity and diabetes mellitus. The disclosure provides improved peptide pharmaceuticals for treatment of disorders associated with obesity or/and diabetes, such as non-alcoholic steatohepatitis (NASH) and polycystic ovary syndrome (PCOS).

In the United States (US), NASH has become the leading cause of end-stage liver disease or liver transplantation. Obesity is the core driver of NASH and weight loss results in reduction in liver fat and NASH improvement. More than 80% of individuals with NASH are overweight or obese, and with no currently available US Food and Drug Administration (FDA)-approved pharmacologic options for inducing weight loss, therapy has largely been based on lifestyle interventions directed at achieving weight loss. However, it is difficult to attain and maintain long-term weight loss with lifestyle changes alone.

Glucagon-like peptide-1 receptor agonists (GLP-1RA) are associated with modest degrees of weight loss at approved doses, and these agents have emerged as a treatment option for patients with NASH. In a recent clinical trial, liraglutide, a daily GLP-1RA, was associated with resolution of NASH, with a trend towards improvement of liver fibrosis. However, patients lost only 5.5% body weight. In one study, 10% or greater weight loss was required for optimal NASH resolution. Higher levels of weight loss have also been associated with lower incidences of cardiovascular disease and non-hepatic malignancies, which represent the most serious co-morbidities facing NASH patients.

GLP-1RAs exert central effects on appetite and food intake, while GCR agonists drive increased energy expenditure in animal models and humans. The effects of GCR agonist and GLP-1RA have been shown to be synergistic in driving greater degrees of weight loss compared to a GLP-1RA alone. GCRs also enhance lipolysis and suppress liver fat synthesis, providing an additional pathway for liver fat reduction and NASH resolution.

Dual agonists combine GCR with GLP-1RA in the same molecule. In obese non-human primates, chronic administration of a GLP-1R/GCR dual agonist reduced body weight and improved glucose tolerance to a greater degree compared to a GLP-1RA mono-agonist. Clinical studies of cotadutide, a GLP-1/GCR dual agonist with a 5:1 bias of GLP-1 to glucagon activity, demonstrated an impressive 39% reduction in liver fat content in just 6 weeks and greater improvement in NASH-related alanine aminotransferase (ALT) reduction than liraglutide alone. However, the degree of weight loss over 26 weeks of cotadutide administration was comparable to liraglutide (5.4% vs. 5.5%), suggesting that the 5:1 ratio was acceptable for liver fat reduction but suboptimal for weight reduction. Balanced (1:1) agonism has been shown to be associated with greater weight loss and metabolic effects than biased ratios that favor one agonist over the other. A recent study with JNJ 64565111, a balanced dual agonist, achieved an impressive 8% reduction in body weight in just 12 weeks (NCT03586830).

Unfortunately, GLP-1RAs have been associated with high rates of nausea, vomiting and diarrhea. These agents must also be titrated over prolonged periods to reduce side effects, and agents with improved tolerability and dosing regimens are needed. Accordingly, there remains a need for convenient dosing (e.g., weekly instead of daily) with a therapeutic dose to control blood glucose and/or induce weight loss that does not need to be titrated to reach a therapeutic level in the absence of gastrointestinal side effects.

SUMMARY OF THE DISCLOSURE

Described herein are dual agonist peptides and products thereof (e.g., formulations) and uses of the same for treating disorders associated with the function of glucagon-like peptide 1 receptor (GLP-1R) and glucagon receptor (GCGR), including but not limited to insulin resistance or/and obesity, such as type 2 diabetes, metabolic syndrome, cardiovascular diseases (including coronary artery diseases such as atherosclerosis and myocardial infarction), hypertension, NASH, chronic kidney disease, chronic weight management and PCOS, and in treating conditions associated with such disorders. Such dual agonist peptides have affinity for both GLP-1R and GCGR, as can be determined for example by a cellular assay as described herein or, using another assay for making such determinations. In some embodiments, the dual agonist peptide is any one of SEQ ID NOS. 1-10, or a derivative thereof, such as a conservatively substituted derivative thereof, and/or combinations thereof. In some embodiments, the dual agonist peptide exhibits about equal affinity for GLP-1R and GCGR as can be determined using the aforementioned cellular assay, which in preferred embodiments is SEQ ID NO: 1, or a derivative thereof.

In some embodiments, this disclosure provides pharmaceutical dosage formulation of such dual agonist peptide(s) configured to control blood glucose with reduction of one or more adverse events as compared to an agonist with unbalanced affinity for GLP-1R and GCGR (e.g., semaglutide) or with an excessively large maximal concentration (Cmax). In some embodiments, this disclosure provides pharmaceutical dosage formulation of such dual agonist peptide(s) configured to induce weight loss for chronic weight management with reduction of one or more adverse events as compared to an agonist with unbalanced affinity to GLP-1R and GCGR. The adverse events being in some embodiments selected from nausea, vomiting, diarrhea, abdominal pain and constipation, upon administration to a mammal. Those adverse events are typically observed following administration of a (dual) agonist with rapid entry into the circulation, leading to an excessively high Cmax. In some embodiments, administration of the dual agonist peptide(s) disclosed herein (e.g., SEQ ID NOS. 1-10 or derivatives thereof) can result in improvements in other results (e.g., weight loss, fat loss, lipid profile) and/or pharmacokinetic (PK) parameters as compared to an agonist with unbalanced affinity for GLP-1R and GCGR (e.g., semaglutide).

In preferred embodiments, this disclosure provides methods for lowering the blood glucose and/or lowering the body weight of a human being, the method comprising administering to the human being a pharmaceutical dosage formulation comprising SEQ ID NO: 1, wherein the occurrence of one or more adverse events is decreased as compared to an agonist with unbalanced affinity for GLP-1R and GCGR, the adverse events being selected from nausea, vomiting, diarrhea, abdominal pain and constipation, upon administration to the human being.

In certain embodiments, this disclosure provides pharmaceutical dosage formulation of such dual agonist peptide(s) configured for treatment of chronic weight management. In embodiments is provided a treatment for chronic weight management of a human being with a body mass index (BMI kg/m$^2$) of at least 25 by inducing weight loss in the human being, the method comprising administering to the human being a once weekly therapeutic effective amount of a pharmaceutical dosage formulation comprising SEQ ID NO: 1, wherein the weight of the human being is reduced by at least 5% (preferably from at least about 5% to about 10%) from baseline at week 12.

Other aspects of this disclosure are also contemplated as will be understood from the same by those of ordinary skill in the art.

BRIEF DESCRIPTION OF THE DRAWINGS

FIG. 14 shows BMI (body mass index) as measured at baseline (screening) and following 12 weeks (Day 85) of treatment with ALT-801 at a weekly dose of 1.2 mg, 1.8 mg and 2.4 mg, as compared to placebo. All treatment groups reduced BMI, with 1.8 mg and 2.4 dose treatment groups demonstrating a significant reduction as compared to placebo.

FIG. 15 shows appetite suppression as measured at early satiety and following 12 weeks of treatment with ALT-801 at a weekly dose of 1.2 mg, 1.8 mg and 2.4 mg, as compared to placebo. All treatment groups demonstrated a decreased appetite and a dose response.

DETAILED DESCRIPTION OF THE DISCLOSURE

Figure 1:
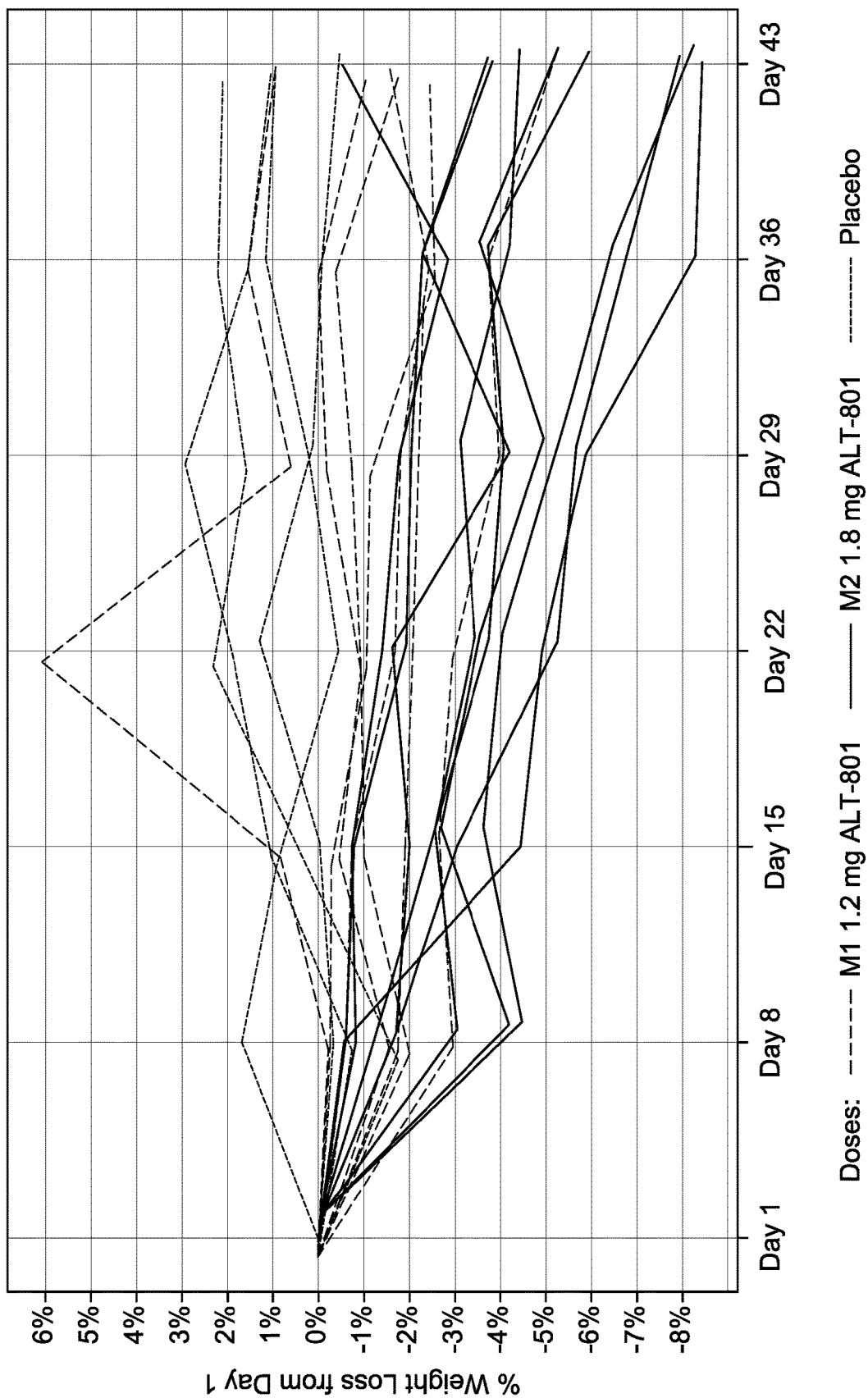
FIG. 1 illustrates the weight loss results following administration of ALT-801 (also referred to herein as pemvidutide) at a dose of 1.2 mg and 1.8 mg as compared to placebo measured over 43 days (see also Table 7).

This disclosure relates to a dual agonist peptide(s) as well as pharmaceutical dosage formulations comprising, and methods for using, the same. The dual agonist peptides have affinity for, and in preferred embodiments about equal affinity for, glucagon-like peptide 1 receptor (GLP-1R) and glucagon receptor (GCGR), as may be determined using a cellular assay. In some embodiments, this disclosure provides pharmaceutical dosage formulations configured to control blood glucose. In some embodiments, blood glucose is better controlled (e.g., lowered and stabilized) following administration of a dual agonist peptide as compared to a selective (e.g., semaglutide) and/or unbalanced agonist. In some embodiments, this disclosure provides pharmaceutical dosage formulations configured to induce weight loss including for treatment of chronic weight management. In some embodiments, weight loss is improved (e.g., lowered and/or stabilized) following administration of a dual agonist peptide as compared to a selective (e.g., semaglutide) and/or unbalanced agonist. In some embodiments, such pharmaceutical dosage formulations exhibit a reduction in adverse events as compared to an agonist with selective (e.g., semaglutide) and/or unbalanced affinity for GLP-1R and GCGR. In some embodiments, the adverse events can include nausea, vomiting, diarrhea, abdominal pain and/or constipation, that are typically observed following administration of upon administration an agonist with unbalanced affinity for GLP-1R and GCGR (e.g., semaglutide) to a mammal. In some embodiments, this disclosure provides novel peptide-based dual GLP-1/glucagon receptor agonists designed to treat the underlying metabolic dysfunction that leads to non-alcoholic steatohepatitis (NASH).

In some embodiments, the dual agonist peptide is any one of SEQ ID NOS. 1-10, or a derivative thereof. In preferred embodiments, the dual agonist peptide is EU-A1873 (SEQ ID NO: 1), EU-A1588 (SEQ ID NO: 2), EU-A1871 (SEQ ID NO:3), EU-A1872 (SEQ ID NO: 4), as shown in Table 1:

TABLE 1

| | SEQ. ID. NO. | 1 | | | | 5 | | | | | 10 | | | | 15 | | | | | 20 | | | | | 25 | | | | 30 |
|---|---|---|---|---|---|---|---|---|---|---|---|---|---|---|---|---|---|---|---|---|---|---|---|---|---|---|---|---|---|
| semaglutide | 11 | H | Aib | E | G | T | F | T | S | D | Y | S | S | Y | L | E | G | Q | A | A | Lys (EPP C17C O2H) | E | F | I | A | W | L V R G | R G |
| EU-A1S73 | 1 | H | Aib | Q | G | T | F | T | S | D | Y | S | K | Y | L | D | E* | Y | Lys (Z17 CO2H) | A | A | K* | E | F | I | Q | W | L L Q T | NH$_2$ |
| EU-A1588 | 2 | H | Aib | Q | G | T | F | T | S | D | Y | S | K | Y | L | D | E* | | Lys (Me 15C O2H) | A | A | K* | E | F | I | Q | W | L L Q T | NH$_2$ |
| EU-A187-1 | 3 | H | Aib | Q | G | T | F | T | S | D | Y | S | K | Y | L | D | E* | | Q | A | A | K* | E | F | I | Lys (Z15 CO2H) | W | L L Q T | NH$_2$ |
| EU-A1372 | 4 | H | Aib | Q | G | T | F | T | S | D | Y | S | K | Y | L | D | E* | | Q | A | A | K* | E | F | I | Lys (Z17 CO2H) | W | L L Q T | NH$_2$ |
| EU-A1880 | 5 | H | Aib | Q | G | T | F | T | S | D | Y | S | R | Y | L | D | E* | | Lys (Z17 CO2H) | A | A | K* | E | F | I | Q | W | L L Q T | NH$_2$ |

E* and K* indicate a side chain lactam linkage between these residues (EPC17CO2H) = (17-carboxyhepadecanoyl-(γ-Glu)-AEEA-AEEA); Z17CO2H = (beta-D-glucuron-1-yl)-1-oxa)17-carboxy-heptadecane;

Me15CO2H = (beta-D-melobiouranyl-1-yl)-1-oxa)15-carboxypentadecane

In Table 1, the numbers 1, 5, 10, 15, 20, 25 and 30 in the top row refer to amino acid residue numbers (29 total amino acid residues being present in each of SEQ ID NOS. 1-5). Semaglutide shown in Table 1 is SEQ ID NO. 11 (31 amino acid residues). As shown in Table 1, SEQ ID NO: 1 (EU-A1873 of Table 1; also known as ALT-801 or pemvidutide) has the following amino acid sequence:

¹His-²Aib-³Gln-⁴Gly-⁵Thr-⁶Phe-⁷Thr-⁸Ser-⁹Asp-

¹⁰Tyr-¹¹Ser-¹²Lys-¹³Tyr-¹⁴Leu-¹⁵Asp-¹⁶Glu*-

¹⁷Lys#-¹⁸Ala-¹⁹Ala-²⁰Lys*-²¹Glu-²²Phe-²³Ile-

²⁴Gln-²⁵Trp-²⁶Leu-²⁷Leu-²⁸Gln-²⁹Thr-NH₂, where * indicates a lactam bridge is formed between Glu16 and Lys 20, and 17Lys# indicates the attachment site for glucuronic acid C-18 *(EuPort G, Z17CO2H).

Illustrated differently, SEQ ID NO: 1 is a peptide amide consisting of 29 amino acid residues and a glucuronic acid/C₁₈ diacid moiety attached to ¹⁷Lys, in which the side-chains of ¹⁶Glu and ²⁰Lys forming an intramolecular cycle as shown below:

wherein: Xaa1 is any amino acid, preferably Aib (α-aminoisobutyric acid (or 2-methylalanine or Calpha-methylalanine)); Xaa2 is Lys(N-omega(1-(17-carboxyl-heptadecyloxy)beta-D-glucuronyl)) or Lys(Z17CO2H) where Z17CO2H is (beta-D-glucuron-1-yl)-1-oxa)17-carboxyheptadecane; and, Glu16 and Lys20 are cyclized with one another through their respective side chains to form a lactam linkage; or a derivative thereof;

2)
```
                                      (SEQ ID NO: 7)
His Xaa1 Gln Gly Thr Phe Thr Ser Asp
1               5

Tyr Ser Lys Tyr Leu Asp Glu Xaa2 Ala
10                  15

Ala Lys Glu Phe Ile Gln Trp Leu Leu Gln Thr
        20                  25
``` wherein: Xaa1 is any amino acid, preferably Aib (α-aminoisobutyric acid (or 2-methylalanine or Calpha-methylalanine)); Xaa2 is Lys(Me17CO2H), where Me17CO2H is beta-D-melobiouranyl-1-yl)-1-oxa)17-carboxyheptadecane; and, Glu16 and Lys20 are cycl-

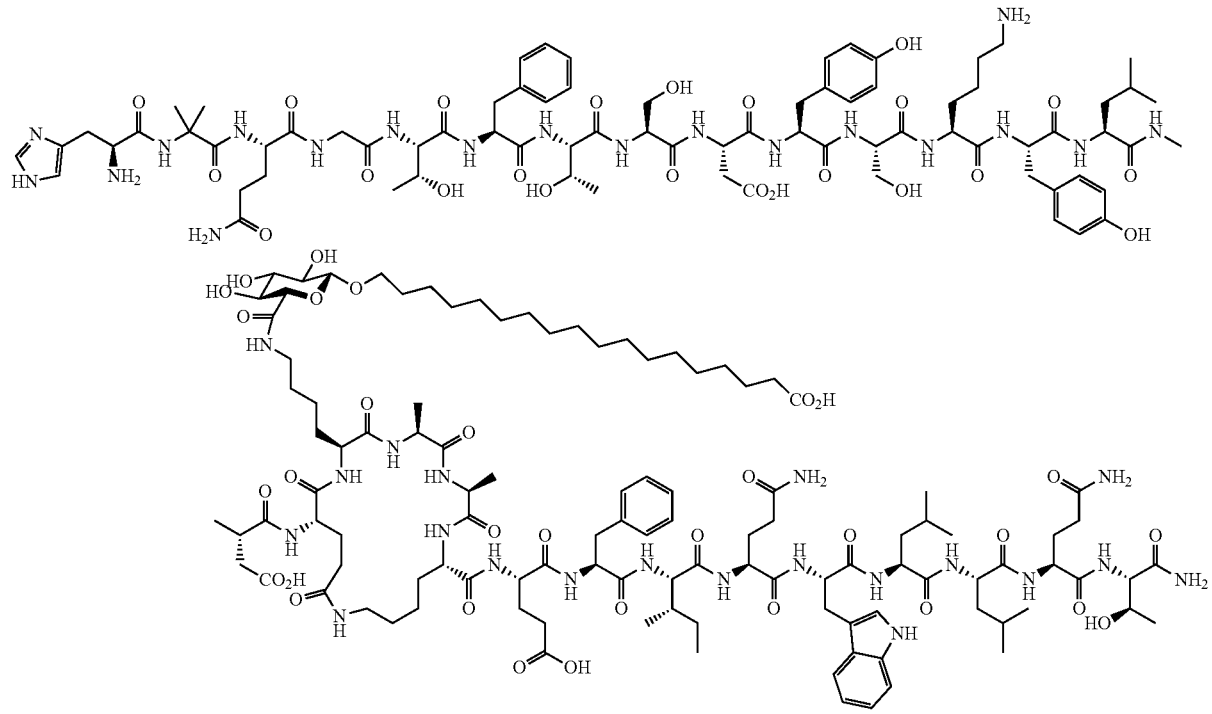

In some embodiments, the dual agonist peptide can be any of:

1)
```
                                      (SEQ ID NO: 6)
His Xaa1 Gln Gly Thr Phe Thr Ser Asp Tyr
1               5                   10

Ser Lys Tyr Leu Asp Glu Xaa2 Ala Ala
            15                  20

Lys Glu Phe Ile Gln Trp Leu Leu Gln Thr
                25
``` ized with one another through their respective side chains to form a lactam linkage; or a derivative thereof;

3)
```
                                      (SEQ ID NO: 8)
His Xaa1 Gln Gly Thr Phe Thr Ser Asp Tyr
1               5                   10

Ser Lys Tyr Leu Asp Glu Gln Ala Ala
            15

Lys Glu Phe Ile Xaa3 Trp Leu Leu Gln Thr
20                  25
``` wherein: Xaa1 is any amino acid, preferably Aib (α-aminoisobutyric acid (or 2-methylalanine or Calpha-methylalanine); Glu16 and Lys20 are cyclized with one another through their respective side chains to form a lactam linkage; Xaa3 is Lys(Z15CO2H) where Z15CO2H is (beta-D-glucuron-1-yl)-1-oxa)15-carboxyheptadecane; or a derivative thereof;

4)
(SEQ ID NO: 9)
His Xaa1 Gln Gly Thr Phe Thr Ser Asp Tyr
1               5                       10
Ser Lys Tyr Leu Asp Glu Gln Ala Ala
                15
Lys Glu Phe Ile Xaa4 Trp Leu Leu Gln Thr
20                   25 wherein: Xaa1 is any amino acid, preferably Aib (α-aminoisobutyric acid (or 2-methylalanine or Calpha-methylalanine); Glu16 and Lys20 are cyclized with one another through their respective side chains to form a lactam linkage; Xaa4 is Lys(Z17CO2H) where Z17CO2H is (beta-D-glucuron-1-yl)-1-oxa)17-carboxyheptadecane; or a derivative thereof;
or, 5)
(SEQ ID NO: 10)
His Xaa1 Gln Gly Thr Phe Thr Ser Asp Tyr
1               5                       10

Ser Xaa5 Tyr Leu Asp Glu Xaa2 Ala Ala
                15

Lys Glu Phe Ile Gln Trp Leu Leu Gln Thr
20                   25 wherein: Xaa1 is any amino acid, preferably Aib (α-aminoisobutyric acid (or 2-methylalanine or Calpha-methylalanine)); Xaa2 is Lys(N-omega(1-(17-carboxyl-heptadecyloxy)beta-D-glucuronyl)) or Lys(Z17CO2H) where Z17CO2H is (beta-D-glucuron-1-yl)-1-oxa)17-carboxyheptadecane; Xaa5 is Arg, and, Glu16 and Lys20 are cyclized with one another through their respective side chains to form a lactam linkage; or a derivative thereof.

In preferred embodiments, the dual agonist peptide is one having the amino acid sequence of any one of SEQ ID NOS: 1-10, or a derivative thereof. In preferred embodiments, the dual agonist peptide is SEQ ID NO: 1. In embodiments provided herein is a pharmaceutical formulation of SEQ ID NO: 1 in an aqueous buffer solution, referred to herein as ALT-801. The dual agonist peptide products herein, including SEQ ID NO: 1, comprise an amino acid side chain amide linkage (lactam bridge), and a EuPort side chain composed of a glucuronic acid linked to an fatty acid side chain. The side chain, a surfactant comprised of a hydrophilic saccharide group covalently attached to the peptide via a linker amino acid, and a hydrophobic alkyl chain portion, results in the formation of micelles after subcutaneous (SC) injection, slowing the entry into the circulation. The lower maximal concentration (Cmax) associated with slower entry could result in fewer GI side effects and better tolerability. This latter feature also enhances binding to plasma proteins and improves the metabolic stability, extending the half-life (t½). The design of SEQ ID NO: 1 has successfully led to a co-agonist with equipotent (1:1) activity at both receptors of approximately 40 pM and 100% activity.

The synthesis of the dual agonist peptides (e.g., SEQ ID NOS. 1-10, or derivatives thereof) is described herein (e.g., Example 1) and in U.S. Pat. No. 9,856,306 B2, which is incorporated by reference in its entirety into this disclosure. In some embodiments, the dual agonist peptides can include one or more conservatively substituted amino acids as described herein. In preferred embodiments, SEQ ID NO: 1 can include one or more conservatively substituted amino acids, but preferably not at amino acid residues 16, 17, or 20. In preferred embodiments, SEQ ID NO: 2 can include one or more conservatively substituted amino acids, but preferably not at amino acid residues 16, 17, or 20. In preferred embodiments, SEQ ID NO: 3 can include one or more conservatively substituted amino acids, but preferably not at amino acid residues 16, 20, or 24. In preferred embodiments, SEQ ID NO: 4 can include one or more conservatively substituted amino acids, but preferably not amino acid residues 16, 20, or 24, SEQ ID NO:5 can include one or more conservatively substituted amino acids, but preferably not amino acid residues 12, 16, 17, or 20.

The peptides of SEQ ID NOS. 1-10 can be collectively referred to herein as the "dual agonist peptides" (or individually as "dual agonist peptide") as each is an agonist for the glucagon-like peptide 1 receptor (GLP-1R) and glucagon receptor (GCGR). In some embodiments, the peptide is a dual agonist of GLP-1R and GCGR as can be determined by a cellular assay such as that described in Example 2 herein. Briefly, in some embodiments, cellular assays can be carried out by measuring cAMP stimulation or arrestin activation in CHO cells into which human GLP-1R or GCGR are expressed ((LeadHunter assays (DiscoveRx)). Preferably, such assays are carried out in the presence of 0.1% ovalbumin as compared to 0.1% bovine serum albumin (BSA) as may be typical, since the dual agonist peptides of SEQ ID NOS. 1-10 can bind very tightly to serum albumin (>99%) and distort the results (see, e.g., Example 2 herein). In some embodiments, as determined using such assays, the dual agonist peptide can have affinity for both GLP-1R and GCGR, and in preferred embodiments about equal affinity for GLP-1R and GCGR. "About equal affinity" means that the dual agonist peptide has no more than about two to three times, preferably not more than two times, the affinity for GLP-1R or GCGR as for the other, as can be determined by such a cellular assay. For instance, as shown in the Examples herein, the dual agonist peptide SEQ ID NO: 1 (EU-A1873) has been surprisingly found to be a dual agonist peptide with about equal affinity for GLP-1R and GCGR (e.g., an EC50 of about 39 pm (115% intrinsic activity) for GLP-1R and 44 pm (115% intrinsic activity) for GCGR). This is unlike the GLP-1 "specific" compounds including semaglutide and Exendin-4, that present affinity strongly biased toward, or only for, GLP-1R; or the strongly GCGR-biased hormone glucagon, which do not show high, or about equal, affinity for both of GLP-1R and GCGR. The native hormone oxyntomodulin has agonistic action at both GLP-1 and glucagon receptors, but this activity is not potent and is not balanced. Those of ordinary skill in the art will understand that affinity to GLP-1R and GCGR can be determined by methods and/or assays other than those described herein and that such methods and/or assays for determining affinity are contemplated herein (e.g., a determination of about equal affinity can be made by such other methods and/or assays).

In embodiments, "a dual agonist peptide with about equal affinity for glucagon-like peptide 1 receptor (GLP-1R) and glucagon receptor (GCGR)" as used herein means a dual agonist peptide that has no more than about two times the affinity for GLP-1R or GCGR as for the other, as can be determined by such a cellular assay. In embodiments, the binding affinity of the present dual agonist peptide for one receptor as compared to the other is no more than 1.9, 1.8, 1.6, 1.5, 1.4, or 1.2 times, as can be determined by known cellular assays. In embodiments, "an agonist with unbalanced affinity for GLP-1R and GCGR" as used herein means an agonist peptide that has at least about 1.5 times the affinity for GLP-1R or GCGR as for the other, as can be determined by known cellular assays. In embodiments, the binding affinity of an agonist with an unbalanced affinity for GLP-1R and GCGR is at least 1.6, 1.8, 2, 2.5, 3, 5, 7.5, 10, 20 times, or more as can be determined by known cellular assays.

A "peptide" (e.g., dual agonist peptide) comprises two or more natural or/and unnatural amino acid residues linked typically via peptide bonds. Such amino acids can include naturally occurring structural variants, naturally occurring non-proteinogenic amino acids, or/and synthetic non-naturally occurring analogs of natural amino acids. The terms "peptide" and "polypeptide" are used interchangeably herein. Peptides include short peptides (about 2-20 amino acids), medium-length peptides (about 21-50 amino acids) and long peptides (>about 50 amino acids, which can also be called "proteins"). In some embodiments, a peptide product comprises a surfactant moiety covalently and stably attached to a peptide of no more than about 50, 40 or 30 amino acids. Synthetic peptides can be synthesized using an automated peptide synthesizer, for example. Peptides can also be produced recombinantly in cells expressing nucleic acid sequences that encode the peptides. Conventional notation is used herein to portray peptide sequences: the left-hand end of a peptide sequence is the amino (N)-terminus, and the right-hand end of a peptide sequence is the carboxyl (C)-terminus. Standard one-letter and three-letter abbreviations for the common amino acids are used herein. Although the abbreviations used in the amino acid sequences disclosed herein represent L-amino acids unless otherwise designated as D- or DL- or the amino acid is achiral, the counterpart D-isomer generally can be used at any position (e.g., to resist proteolytic degradation). Abbreviations for other amino acids used herein include: Aib=a-aminoisobutyric acid (or 2-methylalanine or Ca-methylalanine); Xaa: any amino acid, typically specifically defined within a formula. Abbreviations for other amino acids that can be used as described herein include: Ac3c=1-aminocyclopropane-1-carboxylic acid; Ac4c=1-aminocyclobutane-1-carboxylic acid; Ac5c=1-aminocyclopentane-1-carboxylic acid; Ac6c=1-aminocyclohexane-1-carboxylic acid; Aib=alpha-aminoisobutyric acid (or 2-methylalanine or Calpha-methylalanine); Bip=3-(biphenyl-4-yl)alanine; Bip2Et=3-(2'-ethylbiphenyl-4-yl)alanine; Bip2EtMeO=3-(2'-ethyl-4'-methoxybiphenyl-4-yl)alanine; Cit=citrulline; Deg=2,2-diethylglycine; Dmt=(2,6-dimethyl)tyrosine; 2FPhe=(2-fluorophenyl)alanine; 2FMePhe or 2FaMePhe=Ca-methyl-(2-fluorophenyl)alanine; hArg=homoarginine; MeLys or aMeLys=Ca-methyllysine; MePhe or aMePhe=Ca-methylphenylalanine; MePro or aMePro=Ca-methylproline; Nal1 or Nal(1)=3-(1-naphthyl)alanine; Nal2 or Nal(2)=3-(2-naphthyl)alanine; Nle=norleucine; Orn=ornithine; and Tmp=(2,4,6-trimethylphenyl)alanine; 1,2,3,4-tetrahydroisoquinoline-3-carboxylic acid (Tic) and a Tic-Phe dipeptide moiety with a reduced amide bond between the residues (designated as Tic-Ψ[CF12-NF1]-Ψ-Phe) have the following structures:

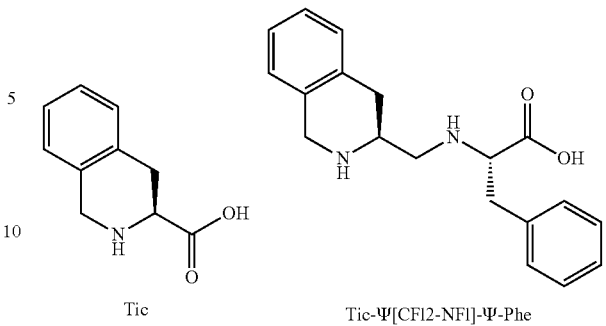

Tic     Tic-Ψ[CF12-NF1]-Ψ-Phe

Unless specifically stated otherwise or the context clearly indicates otherwise, the disclosure encompasses any and all forms of a dual agonist peptide that may be produced, whether the dual agonist peptide is produced synthetically (e.g., using a peptide synthesizer) or by a cell (e.g., by recombinant production). Such forms of a dual agonist peptide can include one or more modifications that may be made during the course of synthetic or cellular production of the peptide, such as one or more post-translational modifications, whether or not the one or more modifications are deliberate. A dual agonist peptide can have the same type of modification at two or more different places, or/and can have two or more different types of modifications. Modifications that may be made during the course of synthetic or cellular production of a dual agonist peptide, including chemical and post-translational modifications, include without limitation glycosylation (e.g., N-linked glycosylation and O-linked glycosylation), lipidation, phosphorylation, sulfation, acetylation (e.g., acetylation of the N-terminus), amidation (e.g., amidation of the C-terminus), hydroxylation, methylation, formation of an intramolecular or intermolecular disulfide bond, formation of a lactam between two side chains, formation of pyroglutamate, and ubiquitination. A dual agonist peptide can have one or more modifications anywhere, such as the N-terminus, the C-terminus, one or more amino acid side chains, or the dual agonist peptide backbone, or any combination thereof. In some embodiments, a dual agonist peptide is acetylated at the N-terminus or/and has a carboxamide (—$CONH_2$) group at the C-terminus, which can increase the stability of the dual agonist peptide.

Potential modifications of a dual agonist peptide also include deletion of one or more amino acids, addition/insertion of one or more natural or/and unnatural amino acids, or substitution with one or more natural or/and unnatural amino acids, or any combination or all thereof. A substitution can be conservative or non-conservative. Such modifications may be deliberate, such as via site-directed mutagenesis or in the chemical synthesis of a dual agonist peptide, or may be accidental, such as via mutations arising in the host cell that produces the dual agonist peptide or via errors due to PCR amplification. An unnatural amino acid can have the same chemical structure as the counterpart natural amino acid but have the D stereochemistry, or it can have a different chemical structure and the D or L stereochemistry. Unnatural amino acids can be utilized, e.g., to promote α-helix formation or/and to increase the stability of the dual agonist peptide (e.g., to resist proteolytic degradation). A dual agonist peptide having one or more modifications relative to a reference dual agonist peptide may be called an "analog" or "variant" of the reference dual agonist peptide as appropriate. An "analog" typically retains one or more essential properties (e.g., receptor binding, activation of a receptor or enzyme, inhibition of a receptor or enzyme, or other biological activity) of the reference dual agonist peptide. A "variant" may or may not retain the biological activity of the reference dual agonist peptide, or/and may have a different biological activity. It is preferred that such a variant maintain its ability to act as an agonist of GLP-1R and GCGR, and in more preferred embodiments, has about equal affinity for GLP-1R and GCGR. In some embodiments, an analog or variant of a reference peptide has a different amino acid sequence than the reference dual agonist peptide.

The term "conservative substitution" refers to substitution of an amino acid in a dual agonist peptide with a functionally, structurally or chemically similar natural or unnatural amino acid. In certain embodiments, the following groups each contain natural amino acids that are conservative substitutions for one another: 1) Glycine (Gly/G), Alanine (Ala/A); 2) Isoleucine (Ile/I), Leucine (Leu/L), Methionine (Met/M), Valine (Val/V); 3) Phenylalanine (Phe/F), Tyrosine (Tyr/Y), Tryptophan (Trp/W); 4) Serine (Ser/S), Threonine (Thr/T), Cysteine (Cys/C); 5) Asparagine (Asn/N), Glutamine (Gln/Q); 6) Aspartic acid (Asp/D), Glutamic acid (Glu/E); and, 7) Arginine (Arg/R), Lysine (Lys/K), Histidine (His/H). In further embodiments, the following groups each contain natural amino acids that are conservative substitutions for one another: 1) non-polar: Ala, Val, Leu, Ile, Met, Pro (proline/P), Phe, Trp; 2) hydrophobic: Val, Leu, Ile, Phe, Trp; 3) aliphatic: Ala, Val, Leu, Ile; 4) aromatic: Phe, Tyr, Trp, His; 5) uncharged polar or hydrophilic: Gly, Ala, Pro, Ser, Thr, Cys, Asn, Gln, Tyr; 6) aliphatic hydroxyl- or sulfhydryl-containing: Ser, Thr, Cys; 7) amide-containing: Asn, Gln; 8) acidic: Asp, Glu; 9) basic: Lys, Arg, His; and, 10) small: Gly, Ala, Ser, Cys. In other embodiments, amino acids may be grouped as conservative substitutions as set out below: 1) hydrophobic: Val, Leu, Ile, Met, Phe, Trp; 2) aromatic: Phe, Tyr, Trp, His; 3) neutral hydrophilic: Gly, Ala, Pro, Ser, Thr, Cys, Asn, Gln; 4) acidic: Asp, Glu; 5) basic: Lys, Arg, His; and, 6) residues that influence backbone orientation: Pro.

Examples of unnatural or non-proteinogenic amino acids include without limitation alanine analogs (e.g., α-ethylGly [α-aminobutyric acid or Abu], α-n-propylGly [norvaline or Nva], α-tert-butylGly [Tbg], α-vinyl Gly [Vg or Vlg], α-allylGly [Alg], α-propargylGly [Prg], 3-cyclopropylAla [Cpa] and Aib), leucine analogs (e.g., nor-leucine, Nle), proline analogs (e.g., α-MePro), phenylalanine analogs (e.g., Phe(2-F), Phe(2-Me), Tmp, Bip, Bip(2'-Et-4'-OMe), Nal1, Nal2, Tic, α-MePhe, α-MePhe(2-F) and α-MePhe(2-Me)), tyrosine analogs (e.g., Dmt and α-MeTyr), serine analogs (e.g., homoserine [isothreonine or hSer]), glutamine analogs (e.g., Cit), arginine analogs (e.g., hArg, N,N'-g-dialkyl-hArg), lysine analogs (e.g, homolysine [hLys], Orn and α-MeLys), a, α-disubstituted amino acids (e.g., Aib, α,α-diethylGly [Deg], α-cyclohexylAla [2-Cha], Ac3c, Ac4c, Ac5c and Ac6c), and other unnatural amino acids disclosed in A. Santoprete et al., Pept. Sci., 17:270-280 (2011). α,α-Di-substituted amino acids can provide conformational restraint or/and α-helix stabilization. A reduced amide bond between two residues (as in, e.g., Tic-Ψ[CF12-NF1]-Ψ-Phe) increases protease resistance and may also, e.g., alter receptor binding. The disclosure encompasses all pharmaceutically acceptable salts of dual agonist peptides, including those with a positive net charge, those with a negative net charge, and those with no net charge.

An "alkyl" group refers to an aliphatic hydrocarbon group. An alkyl group can be saturated or unsaturated, and can be straight-chain (linear), branched or cyclic. In some embodiments, an alkyl group is not cyclic. In some embodiments, an alkyl group contains 1-30, 6-30, 6-20 or 8-20 carbon atoms. A "substituted" alkyl group is substituted with one or more substituents. In some embodiments, the one or more substituents are independently selected from halogens, nitro, cyano, oxo, hydroxy, alkoxy, haloalkoxy, aryloxy, thiol, alkylthio, arylthio, alkylsulfoxide, arylsulfoxide, alkylsulfone, arylsulfone, amino, alkylamino, dialkylamino, arylamino, alkoyl, carboxyl, carboxylate, esters, amides, carbonates, carbamates, ureas, alkyl, haloalkyl, fluoroalkyl, aralkyl, alkyl chains containing an acyl group, heteroalkyl, heteroali-cyclic, aryl, alkoxyaryl, heteroaryl, hydrophobic natural compounds (e.g., steroids), and the like. In some embodiments, an alkyl group as a substituent is linear or branched $Ci$-$C_6$ alkyl, which can be called "lower alkyl". Non-limiting examples of lower alkyl groups include methyl, ethyl, propyl (including n-propyl and isopropyl), butyl (including all isomeric forms, such as n-butyl, isobutyl, sec-butyl and /er/-butyl), pentyl (including all isomeric forms, such as n-pentyl), and hexyl (including all isomeric forms, such as n-hexyl). In some embodiments, an alkyl group is attached to the Na-atom of a residue (e.g., Tyr or Dmt) of a peptide. In certain embodiments, an N-alkyl group is straight or branched C1-$C_{10}$ alkyl, or aryl-substituted alkyl such as benzyl, phenylethyl or the like. One or two alkyl groups can be attached to the Na-atom of the N-terminal residue. In some embodiments, an alkyl group is a 1-alkyl group that is attached to the C-1 position of a saccharide (e.g., glucose) via a glycosidic bond (e.g., an O-, S-, N- or C-glycosidic bond). In some embodiments, such a 1-alkyl group is an unsubstituted or substituted C1-C30, C6-C30, C6-C20 or C8-C20 alkyl group. In some embodiments, an alkyl group (e.g., a 1-alkyl group) is substituted with one or more (e.g., 2 or 3) groups independently selected from aryl, —OH, —OR$^1$, —SH, —SR$^1$, —NH$_2$, —NHR$^1$, —N(R$^1$)$_2$, oxo (=O), —C(=O)R$^2$, carboxyl (—CO$_2$H), carboxylate (—CO$_2$—), —C(=O)OR$^1$, —OC(=O)R$^3$, —C(=O)N(R$^1$)$_2$, —NR$^4$C(=O)R$^3$, —OC(=O)OR$^5$, —OC(=O)N(R$^1$)$_2$, —NR$^4$C(=O)OR$^5$, and —NR$^4$C(=O)N(R$^1$)$_2$, wherein: R$^1$ at each occurrence independently is hydrogen, alkyl or aryl, or both occurrences of R$^1$ and the nitrogen atom to which they are connected form a heterocyclyl or heteroaryl ring; R$^2$ at each occurrence independently is alkyl, heterocyclyl, aryl or heteroaryl; R$^3$ at each occurrence independently is hydrogen, alkyl, heterocyclyl, aryl or heteroaryl; R$^4$ at each occurrence independently is hydrogen or alkyl; and, R$^5$ at each occurrence independently is alkyl or aryl. In some embodiments, an alkyl group (e.g., a 1-alkyl group) is internally or/and terminally substituted with a carboxyl/carboxylate group, an aryl group or an —O-aryl group. In certain embodiments, an alkyl group (e.g., a 1-alkyl group) is substituted with a carboxyl or carboxylate group at the distal end of the alkyl group. In further embodiments, an alkyl group (e.g., a 1-alkyl group) is substituted with an aryl group at the distal end of the alkyl group. In other embodiments, an alkyl group (e.g., al-alkyl group) is substituted with an —O-aryl group at the distal end of the alkyl group. The terms "halogen", "halide" and "halo" refer to fluoride, chloride, bromide and iodide. The term "acyl" refers to —C(=O)R, where R is an aliphatic group that can be saturated or unsaturated, and can be linear, branched or cyclic. In certain embodiments, R contains 1-20, 1-10 or 1-6 carbon atoms. An acyl group can optionally be substituted with one or more groups, such as halogens, oxo, hydroxyl, alkoxy, thiol, alkylthio, amino, alkylamino, dialkylamino, cycloalkyl, aryl, acyl, carboxyl, esters, amides, hydrophobic natural compounds (e.g., steroids), and the like. The terms "heterocyclyl" and "heterocyclic" refer to a monocyclic non-aromatic group or a multicyclic group that contains at least one non-aromatic ring, wherein at least one non-aromatic ring contains one or more heteroatoms independently selected from O, N and S. The non-aromatic ring containing one or more heteroatoms may be attached or fused to one or more saturated, partially unsaturated or aromatic rings. In certain embodiments, a heterocyclyl or heterocyclic group has from 3 to 15, or 3 to 12, or 3 to 10, or 3 to 8, or 3 to 6 ring atoms. Heterocyclyl or heterocyclic groups include without limitation aziridinyl, azetidinyl, pyrrolidinyl, piperidinyl, morpholinyl, piperazinyl, azepanyl, azocanyl, oxiranyl, oxetanyl, tetrahydrofuranyl (oxolanyl), tetrahydropyranyl, oxepanyl and oxocanyl. The term "aryl" refers to a monocyclic aromatic hydrocarbon group or a multicyclic group that contains at least one aromatic hydrocarbon ring. In certain embodiments, an aryl group has from 6 to 15, or 6 to 12, or 6 to 10 ring atoms. Aryl groups include without limitation phenyl, naphthalenyl (naphthyl), fluorenyl, azulenyl, anthryl, phenanthryl, biphenyl and terphenyl. The aromatic hydrocarbon ring of an aryl group may be attached or fused to one or more saturated, partially unsaturated or aromatic rings—e.g., dihydronaphthyl, indenyl, indanyl and tetrahydronaphthyl (tetralinyl). An aryl group can optionally be substituted with one or more (e.g., 2 or 3) substituents independently selected from halogens (including —F and —Cl), cyano, nitro, hydroxyl, alkoxy, thiol, alkylthio, alkylsulfoxide, alkylsulfone, amino, alkylamino, dialkylamino, alkyl, haloalkyl (including fluoroalkyl such as trifluoromethyl), acyl, carboxyl, esters, amides, and the like. The term "heteroaryl" refers to a monocyclic aromatic group or a multicyclic group that contains at least one aromatic ring, wherein at least one aromatic ring contains one or more heteroatoms independently selected from O, N and S. The heteroaromatic ring may be attached or fused to one or more saturated, partially unsaturated or aromatic rings that may contain only carbon atoms or that may contain one or more heteroatoms. In certain embodiments, a heteroaryl group has from 5 to 15, or 5 to 12, or 5 to 10 ring atoms. Monocyclic heteroaryl groups include without limitation pyrrolyl, pyrazolyl, pyrazolinyl, imidazolyl, oxazolyl, isoxazolyl, thiazolyl, thiadiazolyl, isothiazolyl, furanyl, thienyl (thiophenyl), oxadiazolyl, triazolyl, tetrazolyl, pyridyl, pyridonyl, pyrazinyl, pyrimidinyl, pyridazinyl, pyridazinonyl and triazinyl. Non-limiting examples of bicyclic heteroaryl groups include indolyl, benzothiazolyl, benzothiadiazolyl, benzoxazolyl, benzisoxazolyl, benzothienyl (benzothiophenyl), quinolinyl, tetrahydroisoquinolinyl, isoquinolinyl, benzimidazolyl, benzotriazolyl, indolizinyl, benzofuranyl, isobenzofuranyl, chromonyl, coumarinyl, cinnolinyl, quinazolinyl, quinoxalinyl, indazolyl, naphthyridinyl, phthalazinyl, quinazolinyl, purinyl, pyrrol opyridinyl, furopyridinyl, thienopyridinyl, dihydroisoindolyl and tetrahydroquinolinyl.

In some embodiments, for instance, the dual agonist peptides can be associated with a saccharide, such as within a pharmaceutically acceptable composition or lyophilizate. Saccharides include monosaccharides, disaccharides and oligosaccharides (e.g., trisaccharides, tetrasaccharides and so on). A reducing saccharide exists in a ring form and an open-chain form in equilibrium, which generally favors the ring form. A functionalized saccharide of a surfactant moiety has a functional group suitable for forming a stable covalent bond with an amino acid of a dual agonist peptide.

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" excipient or carrier of a pharmaceutical composition is also compatible with the other ingredients of the composition. In one embodiment, a pharmaceutically acceptable composition in which a dual agonist peptide can be formulated comprises polysorbate 20 (e.g., about 0.050% (w/w)); optionally methylparaben (e.g., about 0.300% (w/w)); arginine (about 0.348% (w/w)), and mannitol (e.g., about 4.260% (w/w)) in distilled (DI) water.

The term "therapeutically effective amount" refers to an amount of a compound that, when administered to a subject, is sufficient to prevent, reduce the risk of developing, delay the onset of, slow the progression of or cause regression of the medical condition being treated, or to alleviate to some extent the medical condition or one or more symptoms or complications of that condition, at least in some fraction of the subjects taking that compound. The term "therapeutically effective amount" also refers to an amount of a compound that is sufficient to elicit the biological or medical response of a cell, tissue, organ or human which is sought by a medical doctor or clinician.

The terms "treat," "treating" and "treatment" include alleviating, ameliorating, inhibiting the progress of, reversing or abrogating a medical condition or one or more symptoms or complications associated with the condition, and alleviating, ameliorating or eradicating one or more causes of the condition. Reference to "treatment" of a medical condition includes prevention of the condition. The terms "prevent", "preventing" and "prevention" include precluding, reducing the risk of developing and delaying the onset of a medical condition or one or more symptoms or complications associated with the condition. The term "medical conditions" (or "conditions" for brevity) includes diseases and disorders. The terms "diseases" and "disorders" are used interchangeably herein.

The disclosure also provides pharmaceutical compositions comprising a dual agonist peptide product described herein or a pharmaceutically acceptable salt thereof, and one or more pharmaceutically acceptable carriers or excipients. A pharmaceutical composition contains a therapeutically effective amount of a peptide product or an appropriate fraction thereof. A composition can optionally contain an additional therapeutic agent. In some embodiments, a peptide product is at least about 90%, 95% or 98% pure. Pharmaceutically acceptable excipients and carriers include pharmaceutically acceptable substances, materials and vehicles. Non-limiting examples of types of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, stabilizers, antioxidants, preservatives, antimicrobial agents, antibacterial agents, antifungal agents, chelating agents, adjuvants, sweetening agents, flavoring agents, coloring agents, encapsulating materials and coating materials. The use of such excipients in pharmaceutical formulations is known in the art. For example, conventional vehicles and carriers include without limitation oils (e.g., vegetable oils such as olive oil and sesame oil), aqueous solvents (e.g., saline, buffered saline (e.g., phosphate-buffered saline [PBS]) and isotonic solutions (e.g., Ringer's solution)), and organic solvents (e.g., dimethyl sulfoxide and alcohols [e.g., ethanol, glycerol and propylene glycol]). Except insofar as any conventional excipient or carrier is incompatible with a peptide product, the disclosure encompasses the use of conventional excipients and carriers in formulations containing a peptide product. See, e.g., Remington: The Science and Practice of Pharmacy, 21st Ed., Lippincott Williams & Wilkins (Philadelphia, Pennsylvania) (2005); Handbook of Pharmaceutical Excipients, 5th Ed., Rowe et ah, Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Pre-formulation and Formulation, Gibson, Ed., CRC Press (Boca Raton, Florida) (2004).

In embodiments, a pharmaceutical formulation comprises a peptide product and about 0.025-0.075% (w/w) polysorbate 20, about 0.2-0.5% (w/w) arginine, about 3-6% (w/w) mannitol in deionized water (pH 7.7±0.1); optionally about 0.050% (w/w) polysorbate 20, about 0.348% (w/w) arginine, about 4.260% (w/w) mannitol in deionized water (pH 7.7±0.1). In certain embodiments, a present pharmaceutical formulation comprises SEQ ID NO: 1 and about 0.050% (w/w) polysorbate 20, about 0.348% (w/w) arginine, about 4.260% (w/w) mannitol in deionized water (pH 7.7±0.1). In certain embodiments, the pharmaceutical formulation comprises SEQ ID NO: 1 and is configured for subcutaneous (SC) administration of a weekly therapeutic dose.

An appropriate or suitable formulation can depend on various factors, such as the route of administration chosen. Potential routes of administration of a pharmaceutical composition comprising a peptide product include without limitation oral, parenteral (including intradermal, subcutaneous, intramuscular, intravascular, intravenous, intra-arterial, intraperitoneal, intracavitary and topical), and topical (including transdermal, transmucosal, intranasal (e.g., by nasal spray or drop), ocular (e.g., by eye drop), pulmonary (e.g., by oral or nasal inhalation), buccal, sublingual, rectal (e.g., by suppository), and vaginal (e.g., by suppository). In certain embodiments, a present dual agonist peptide product is administered parenterally (e.g., subcutaneously, intravenously or intramuscularly). In other embodiments, a peptide product is administered by oral inhalation or nasal inhalation or insufflation. In some embodiments, the carrier is an aqueous-based carrier, such as in a parenteral (e.g., subcutaneous, intravenous or intramuscular) formulation. In other embodiments, the carrier is a nonaqueous-based carrier. In certain embodiments, the nonaqueous-based carrier is a hydrofluoroalkane (HFA) or HFA-like solvent that may comprise sub-micron anhydrous α-lactose or/and other excipients, such as in a formulation for administration by oral inhalation or nasal inhalation or insufflation.

In some embodiments, a peptide product is administered parenterally (e.g., subcutaneously, intravenously or intramuscularly) by injection. Parenteral administration bypasses the strongly acidic environment of the stomach, gastrointestinal (GI) absorption and first-pass metabolism. Excipients and carriers that can be used to prepare parenteral formulations include without limitation solvents (e.g., aqueous solvents such as water, saline, physiological saline, buffered saline [e.g., PBS], balanced salt solutions [e.g., Ringer's BSS] and aqueous dextrose solutions), isotonic/iso-osmotic agents (e.g., salts [e.g., NaCl, KCl and $CaCl_2$] and sugars [e.g., sucrose]), buffering agents and pH adjusters (e.g., sodium dihydrogen phosphate [monobasic sodium phosphate]/di sodium hydrogen phosphate [dibasic sodium phosphate], citric acid/sodium citrate and L-histidine/L-histidine HCl), and emulsifiers (e.g., non-ionic surfactants such as polysorbates [e.g., polysorbate 20 and 80] and poloxamers [e.g., poloxamer 188]). Peptide formulations and delivery systems are discussed in, e.g., A. J. Banga, Therapeutic Peptides and Proteins: Formulation, Processing, and Delivery Systems, 3rd Ed., CRC Press (Boca Raton, Florida) (2015). The excipients can optionally include one or more substances that increase peptide stability, increase peptide solubility, inhibit peptide aggregation or reduce solution viscosity, or any combination or all thereof. Such substances include without limitation hydrophilic amino acids (e.g., arginine and histidine), polyols (e.g., myo-inositol, mannitol and sorbitol), saccharides (e.g., glucose (including D-glucose [dextrose]), lactose, sucrose and trehalose}, osmolytes (e.g., trehalose, taurine, amino acids [e.g., glycine, sarcosine, alanine, proline, serine, b-alanine and g-aminobutyric acid], and betaines [e.g., trimethylglycine and trimethylamine N-oxide]), and non-ionic surfactants (e.g., alkyl polyglycosides, ProTek® alkylsaccarides (e.g., a monosaccharide [e.g., glucose] or a disaccharide [e.g., maltose or sucrose] coupled to a long-chain fatty acid or a corresponding long-chain alcohol), and polypropylene glycol/polyethylene glycol block co-polymers (e.g., poloxamers [e.g., Pluronic™ F-68], and Genapol® PF-10 and variants thereof). Because such substances increase peptide solubility, they can be used to increase peptide concentration in a formulation. Higher peptide concentration in a formulation is particularly advantageous for subcutaneous administration, which has a limited volume of bolus administration (e.g., <about 1.5 mL). In addition, such substances can be used to stabilize peptides during the preparation, storage and reconstitution of lyophilized peptides. An exemplary parenteral formulation comprises a peptide product, mannitol, methionine, sodium thioglycolate, polysorbate 20, a pH adjuster (e.g., NaOH or/and HCl) and de-ionized water. Excipients of parenteral formulations that would be suitable for use with the dual agonist peptides described herein (e.g., various combinations of excipients including NaCl and the like) are well-known and available to those of ordinary skill in the art.

For parenteral (e.g., subcutaneous, intravenous or intramuscular) administration, a sterile solution or suspension of a peptide product in an aqueous solvent containing one or more excipients can be prepared beforehand and can be provided in, e.g., a pre-filled syringe of a single-use pen or a pen with a dose counter. Alternatively, a peptide product can be dissolved or suspended in an aqueous solvent that can optionally contain one or more excipients prior to lyophilization (freeze-drying). Shortly prior to parenteral administration, the lyophilized peptide product stored in a suitable container (e.g., a vial) can be reconstituted with, e.g., sterile water that can optionally contain one or more excipients. In other embodiments, an agonist peptide product is administered intranasally. The nasal mucosa provides a big surface area, a porous endothelium, a highly vascular subepithelial layer and a high absorption rate, and hence allows for high bioavailability. An intranasal formulation can comprise a peptide product along with excipients, such as a solubility enhancer (e.g., propylene glycol), a humectant (e.g., mannitol or sorbitol), a buffer and water, and optionally a preservative (e.g., benzalkonium chloride), a mucoadhesive agent (e.g., hydroxyethylcellulose) or/and a penetration enhancer. An intranasal solution or suspension formulation can be administered to the nasal cavity by any suitable means, including but not limited to a dropper, a pipette, or spray using, e.g., a metering atomizing spray pump. Table 2 shows exemplary excipients of nasal-spray formulations.

TABLE 2

Exemplary excipients and carriers of nasal and pulmonary formulations

| Dosage Form | Ingredients in Addition to a Peptide Product |
|---|---|
| nasal spray | microcrystalline cellulose, sodium carboxymethylcellulose, dextrose, water, and optionally a pH adjuster (e.g., HCl) |
| nasal spray | microcrystalline cellulose, carboxymethyl cellulose sodium, dextrose, polysorbate 80, disodium edetate, potassium sorbate, a pH adjuster (e.g., HCl), water, and optionally an alcohol (e.g., ethanol) |
| nasal spray | microcrystalline cellulose, carboxymethyl cellulose sodium, dextrose, polysorbate 80, benzalkonium chloride, phenylethyl alcohol, water, and optionally an alcohol (e.g., ethanol) |
| nasal spray | hypromellose, benzalkonium chloride, NaCl, EDTA, citric acid, sodium phosphate dibasic, water, and optionally an alcohol (e.g., ethanol) |
| inhalation (DPI) | mannitol, glycine, sodium citrate and NaOH |
| inhalation (DPI) | lactose, starch, a starch derivative (e.g., hydroxypropylmethyl cellulose) or polyvinylpyrrolidine, and optionally magnesium stearate or/and leucine |
| inhalation (MDI) | a propellant (e.g., 1,1,1,2-tetrafluoroethane), a surfactant (e.g., lecithin or oleic acid), and a co-solvent (e.g., ethanol) |
| inhalation (nebulizer) | polysorbate 80, edetate disodium, sodium chloride, pH buffering agents (e.g., citric acid/sodium citrate), and water |

In further embodiments, a peptide product is administered via a pulmonary route, such as by oral inhalation or nasal inhalation. Pulmonary administration of a drug can treat a lung disorder or/and a systemic disorder, as the lungs serve as a portal to the systemic circulation. Advantages of pulmonary drug delivery include, for example: 1) avoidance of first-pass metabolism; 2) fast drug action; 3) large surface area of the alveolar region for absorption, high permeability of the lungs (thin air-blood barrier), and profuse vasculature of the airways; and 4) reduced extracellular enzyme levels compared to the GI tract due to the large alveolar surface area. An advantage of oral inhalation over nasal inhalation includes deeper penetration/deposition of the drug into the lungs, although nasal inhalation can deliver the drug into systemic circulation transmucosally in the nasal cavity as well as in the lungs. Oral or nasal inhalation can be achieved by means of, e.g., a metered-dose inhaler (MDI), a nebulizer or a dry powder inhaler (DPI). For example, a peptide product can be formulated for aerosol administration to the respiratory tract by oral or nasal inhalation. The drug is delivered in a small particle size (e.g., between about 0.5 micron and about 5 microns), which can be obtained by micronization, to improve, e.g., drug deposition in the lungs and drug suspension stability. The drug can be provided in a pressurized pack with a suitable propellant, such as a hydrofluoroalkane (HFA, e.g., 1,1,1,2-tetrafluoroethane [HFA-134a]), a chlorofluorocarbon (CFC, e.g., dichlorodifluoromethane, trichlorofluoromethane or dichlorotetrafluoroethane), or a suitable gas (e.g., oxygen, compressed air or carbon dioxide). The drug in the aerosol formulation is dissolved, or more often suspended, in the propellant for delivery to the lungs. The aerosol can contain excipients such as a surfactant (which enhances penetration into the lungs by reducing the high surface tension forces at the air-water interface within the alveoli, may also emulsify, solubilize or/and stabilize the drug, and can be, e.g., a phospholipid such as lecithin) or/and a stabilizer, although the surfactant moiety of the peptide product can perform functions of a surfactant. For example, an MDI formulation can comprise a peptide product, a propellant (e.g., an HFA such as 1,1,1,2-tetrafluoroethane) and a co-solvent (e.g., an alcohol such as ethanol), and optionally a surfactant (e.g., a fatty acid such as oleic acid). The MDI formulation can optionally contain a dissolved gas (e.g., $CO_2$). After device actuation, the bursting of $CO_2$ bubbles within the emitted aerosol droplets breaks up the droplets into smaller droplets, thereby increasing the respirable fraction of drug. As another example, a nebulizer formulation can comprise a peptide product, a chelator or preservative (e.g., edetate disodium), an isotonicity agent (e.g., NaCl), pH buffering agents (e.g., citric acid/sodium citrate) and water, and optionally a surfactant (e.g., a Tween® such as polysorbate 80). The drug can be delivered by means of, e.g., a nebulizer or an MDI with or without a spacer, and the drug dose delivered can be controlled by a metering chamber (nebulizer) or a metering valve (MDI).

Table 2 shows exemplary MDI, nebulizer and DPI formulations. Metered-dose inhalers (also called pressurized metered-dose inhalers [pMDI]) are the most widely used inhalation devices. A metering valve delivers a precise amount of aerosol (e.g., about 20-100 pL) each time the device is actuated. MDIs typically generate aerosol faster than the user can inhale, which can result in deposition of much of the aerosol in the mouth and the throat. The problem of poor coordination between device actuation and inhalation can be addressed by using, e.g., a breath-actuated MDI or a coordination device. A breath-actuated MDI (e.g., Easi Breathe®) is activated when the device senses the user's inspiration and discharges a drug dose in response. The inhalation flow rate is coordinated through the actuator and the user has time to actuate the device reliably during inhalation. In a coordination device, a spacer (or valved holding chamber), which is a tube attached to the mouthpiece end of the inhaler, serves as a reservoir or chamber holding the drug that is sprayed by the inhaler and reduces the speed at which the aerosol enters the mouth, thereby allowing for the evaporation of the propellant from larger droplets. The spacer simplifies use of the inhaler and increases the amount of drug deposited in the lungs instead of in the upper airways. The spacer can be made of an anti-static polymer to minimize electrostatic adherence of the emitted drug particles to the inner walls of the spacer. Nebulizers generate aerosol droplets of about 1-5 microns. They do not require user coordination between device actuation and inhalation, which can significantly affect the amount of drug deposited in the lungs. Compared to MDIs and DPIs, nebulizers can deliver larger doses of drug, albeit over a longer administration time. Examples of nebulizers include without limitation human-powered nebulizers, jet nebulizers (e.g., AeroEclipse® II BAN [breath-actuated], CompAIR™ NE-C801 [virtual valve], PARI LC® Plus [breath-enhanced] and SideStream Plus [breath-enhanced]), ultrasonic wave nebulizers, and vibrating mesh nebulizers (e.g., Akita2® Apixneb, I-neb AAD System with metering chambers, MicroAir® NE-U22, Omron U22 and PARI eFlow® rapid). As an example, a pulsed ultrasonic nebulizer can aerosolize a fixed amount of the drug per pulse, and can comprise an opto-acoustical trigger that allows the user to synchronize each breath to each pulse. For oral or nasal inhalation using a dry powder inhaler (DPI), a peptide product can be provided in the form of a dry micronized powder, where the drug particles are of a certain small size (e.g., between about 0.5 micron and about 5 microns) to improve, e.g., aerodynamic properties of the dispersed powder and drug deposition in the lungs. Particles between about 0.5 micron and about 5 microns deposit by sedimentation in the terminal bronchioles and the alveolar regions. By contrast, the majority of larger particles (>5 microns) do not follow the stream of air into the many bifurcations of the airways, but rather deposit by impaction in the upper airways, including the oropharyngeal region of the throat. A DPI formulation can contain the drug particles alone or be blended with a powder of a suitable larger base/carrier, such as lactose, starch, a starch derivative (e.g., hydroxypropylmethyl cellulose) or polyvinylpyrrolidine. The carrier particles enhance flow, reduce aggregation, improve dose uniformity and aid in dispersion of the drug particles. A DPI formulation can optionally contain an excipient such as magnesium stearate or/and leucine that improves the performance of the formulation by interfering with inter-particle bonding (by anti-adherent action). The powder formulation can be provided in unit dose form, such as a capsule (e.g., a gelatin capsule) or a cartridge in a blister pack, which can be manually loaded or pre-loaded in an inhaler. The drug particles can be drawn into the lungs by placing the mouthpiece or nosepiece of the inhaler into the mouth or nose, taking a sharp, deep inhalation to create turbulent airflow, and holding the breath for a period of time (e.g., about 5-10 seconds) to allow the drug particles to settle down in the bronchioles and the alveolar regions. When the user actuates the DPI and inhales, airflow through the device creates shear and turbulence, inspired air is introduced into the powder bed, and the static powder blend is fluidized and enters the user's airways. There, the drug particles separate from the carrier particles due to turbulence and are carried deep into the lungs, while the larger carrier particles impact on the oropharyngeal surfaces and are cleared. Thus, the user's inspiratory airflow achieves powder de-agglomeration and aeroionisation, and determines drug deposition in the lungs. (While a passive DPI requires rapid inspiratory airflow to de agglomerate drug particles, rapid inspiration is not recommended with an MDI or nebulizer, since it creates turbulent airflow and fast velocity which increase drug deposition by impaction in the upper airways.) Compared to an MDI, a DPI (including a breath-activated DPI) may be able to deliver larger doses of drug, and larger-size drugs (e.g., macromolecules), to the lungs.

Lactose (e.g., alpha-lactose monohydrate) is the most commonly used carrier in DPI formulations. Examples of grades/types of lactose monohydrate for DPI formulations include without limitation DCL 11, Flowlac® 100, Inhalac® 230, Lactohale® 300, Lactopress® SD 250 (spray-dried lactose), Respitose® SV003 and Sorbolac® 400. A DPI formulation can contain a single lactose grade or a combination of different lactose grades. For example, a fine lactose grade like Lactohale® 300 or Sorbolac® 400 may not be a suitable DPI carrier and may need to be blended with a coarse lactose grade like DCL 11, Flowlac® 100, Inhalac® 230 or Respitose® SV003 (e.g., about a 1:9 ratio of fine lactose to coarse lactose) to improve flow.

Tables 3 and 4 show non-limiting examples of grades/types of lactose that can be used in DPI formulations. The distribution of the carrier particle sizes affects the fine particle fraction/dose (FPF or FPD) of the drug, with a high FPF being desired for drug delivery to the lungs. FPF/FPD is the respirable fraction/dose mass out of the DPI device with an aerodynamic particle size <5 microns in the inspiration air. High FPF, and hence good DPI performance, can be obtained from, e.g., DPI formulations having an approximately 1:9 ratio of fine lactose (e.g., Lactohale® 300) to coarse lactose (e.g., Respitose® SV003) and about 20% w/w overages to avoid deposition of the drug in the capsule shell or the DPI device and to deliver essentially all of the drug to the airways.

TABLE 3

| | | Range of Particle Sizes (μm) | | |
|---|---|---|---|---|
| Product | Type | 10% | 50% | 90% |
| Lactohale ® | LH200 | <9 | <69 | <141 |
| InhaLac ® | 230 | <35 | <93 | <138 |
| Respitose ® | ML001 | <4 | <43 | <146 |
| | ML003 | <4 | <35 | <106 |
| | SV003 | <30 | <59 | <90 |
| | SV004 | <32 | <61 | <93 |

TABLE 4

| | | Range of Particle Sizes | | | |
|---|---|---|---|---|---|
| Product | Type | <45 μm | <100 μm | <150 μm | <250 μm |
| Respitose ® | ML003 | 65% | 98% | 100% | NA |
| Respitose ® | ML002 | 65% | 98% | NA | 100% |

Other carriers for DPI formulations include without limitation glucose, mannitol (e.g., crystallized mannitol [Pearlitol 110 C] and spray-dried mannitol [Pearlitol 100 SD]), maltitol (e.g., crystallized maltitol [Maltisorb P90]), sorbitol and xylitol. Most DPIs are breath-activated ("passive"), relying on the user's inhalation for aerosol generation. Examples of passive DPIs include without limitation Airmax®, Novolizer® and Otsuka DPI (compact cake). The air classifier technology (ACT) is an efficient passive powder dispersion mechanism employed in DPIs. In ACT, multiple supply channels generate a tangential airflow that results in a cyclone within the device during inhalation. There are also power-assisted ("active") DPIs (based on, e.g., pneumatics, impact force or vibration) that use energy to aid, e.g., particle de-agglomeration. For example, the active mechanism of Exubera® inhalers utilizes mechanical energy stored in springs or compressed-air chambers. Examples of active DPIs include without limitation Actispire® (single-unit dose), Aspirair® (multi-dose), Exubera® (single-unit dose), MicroDose® (multi-unit dose and electronically activated), Omnihaler® (single-unit dose), Pfeiffer DPI (single-unit dose), and Spiros® (multi-unit dose). A peptide product can also be administered by other routes, such as orally. An oral formulation can contain a peptide product and conventional excipients known in the art, and optionally an absorption enhancer such as sodium V-[8-(2-hydroxybenzoyl) aminocaprylate] (SNAC). SNAC protects against enzymatic degradation via local buffering action and enhances GI absorption. An oral dosage form (e.g., a tablet, capsule or pill) can optionally have an enteric coating to protect its content from the strong acids and proteolytic enzymes of the stomach. In some embodiments, a peptide product is delivered from a sustained-release composition. As used herein, the term "sustained-release composition" encompasses sustained-release, prolonged-release, extended-release, delayed-release, slow-release and controlled-release compositions, systems and devices. In some embodiments, a sustained-release composition delivers a peptide product over a period of at least about 1 week, 2 weeks, 3 weeks, 1 month, 2 months, 3 months or longer. In some embodiments, a sustained-release composition is formulated as nanoparticles or microparticles composed of a biodegradable polymer and incorporating a peptide product. In certain embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. In further embodiments, a sustained-release composition is in the form of a depot that is generated when a mixture of a peptide product and a polymer is injected into a subject intramuscularly or subcutaneously. In certain embodiments, the polymer is or comprises PEG, polylactic acid (PLA) or polyglycolic acid (PGA), or a copolymer thereof (e.g., PLGA or PLA-PEG).

A pharmaceutical composition can be presented in unit dosage form as a single dose wherein all active and inactive ingredients are combined in a suitable system, and components do not need to be mixed to form the composition to be administered. A unit dosage form generally contains a therapeutically effective dose of the drug but can contain an appropriate fraction thereof so that taking multiple unit dosage forms achieves the therapeutically effective dose. Examples of a unit dosage form include a tablet, capsule or pill for oral uptake; a solution in a pre-filled syringe of a single-use pen or a pen with a dose counter for parenteral (e.g., intravenous, subcutaneous or intramuscular) injection; and a capsule, cartridge or blister pre-loaded in or manually loaded into an inhaler. Alternatively, a pharmaceutical composition can be presented as a kit in which the active ingredient, excipients and carriers (e.g., solvents) are provided in two or more separate containers (e.g., ampules, vials, tubes, bottles or syringes) and need to be combined to form the composition to be administered. The kit can contain instructions for storing, preparing and administering the composition (e.g., a solution to be injected parenterally). A kit can contain all active and inactive ingredients in unit dosage form or the active ingredient and inactive ingredients in two or more separate containers, and can contain instructions for administering or using the pharmaceutical composition to treat a medical condition disclosed herein. A kit can further contain a device for delivering the composition, such as an injection pen or an inhaler. In some embodiments, a kit contains a peptide product or a pharmaceutically acceptable salt thereof, or a pharmaceutical composition comprising the same, and instructions for administering or using the peptide product or the composition to treat a medical condition disclosed herein, such as insulin resistance, diabetes, metabolic syndrome, cardiovascular disease, obesity (including "chronic obesity" meaning obesity lasting more than one year or resulting in an obesity-related condition such as but not limited to insulin resistance, diabetes, metabolic syndrome, and/or cardiovascular disease), or a condition associated therewith (e.g., NASH or PCOS). In certain embodiments, the kit further contains a device for delivering the peptide product or the composition, such as an injection pen or an inhaler.

The disclosure further provides uses of the dual agonist peptide products described herein to prevent and/or treat conditions associated with GLP1R and/or GCGR, such as but not limited to insulin resistance, diabetes, obesity, metabolic syndrome and cardiovascular diseases, and conditions associated therewith, such as NASH and PCOS. In some embodiments, the dual agonist peptide products can be used to treat hyperglycemia, insulin resistance, hyperinsulinemia, prediabetes, diabetes (including types 1 and 2, gestational and juvenile diabetes), diabetic complications, diabetic neuropathy, diabetic nephropathy, diabetic retinopathy, hyperlipidemia, hypercholesterolemia, hypertriglyceridemia, elevated blood levels of free fatty acids, obesity, metabolic syndrome, syndrome X, cardiovascular diseases (including coronary artery disease), atherosclerosis, acute cardiovascular syndrome, ischemia (including myocardial ischemia and cerebral ischemia/stroke), ischemia-reperfusion injury (including myocardial and cerebral IRI), infarction (including myocardial and cerebral infarction), angina, heart failure (e.g., congestive heart failure), peripheral vascular disease, thrombosis (e.g., deep vein thrombosis), embolism (e.g., pulmonary embolism), systemic inflammation (e.g., one characterized by elevated C-reactive protein blood level), and hypertension. The dual agonist peptide products can achieve their therapeutic effects through various mechanisms, including stimulation of blood glucose-dependent insulin secretion, increase in insulin sensitivity, stimulation of fat burning and reduction of body weight. The dual agonist peptide products can also promote, e.g., pancreatic beta-cell protection, cardioprotection and wound healing.

The peptide products described herein can be used to treat other conditions associated with insulin resistance or/and obesity. Other conditions associated with insulin resistance or/and obesity include without limitation arthritis (e.g., osteoarthritis), low back pain, breathing disorders (e.g., asthma, obesity hypoventilation syndrome [Pickwickian syndrome] and obstructive sleep apnea), dermatological disorders (e.g., diabetic ulcers, acanthosis *nigricans*, cellulitis, hirsutism, intertrigo and lymphedema), gastroenterological disorders (e.g., cholelithiasis [gallstone], gastroesophageal reflux disease [GERD] and gastroparesis), gout, hypercortisolism (e.g., Cushing's syndrome), kidney disorders (e.g., chronic kidney disease), liver disorders (e.g., fatty liver disease [FLD] including alcoholic and non-alcoholic FLD), neurological disorders (e.g., carpal tunnel syndrome, dementias [e.g., Alzheimer's disease and vascular dementia], meralgia paresthetica, migraines and multiple sclerosis), urological disorders (e.g., erectile dysfunction, hypogonadism and urinary incontinence), polycystic ovary syndrome, infertility, menstrual disorders, mood disorders (e.g., depression), and cancers (e.g., cancers of the endometrium, esophagus, colorectum, gallbladder, kidney, liver [e.g., hepatocellular carcinoma], pancreas and skin [e.g., melanoma], and leukemia). In certain embodiments, a dual agonist peptide product described herein is used to treat polycystic ovary syndrome (PCOS). In other embodiments, a peptide product is used to treat chronic kidney disease (CKD), also known as chronic kidney/renal failure (CKF/CRF). The most common causes of CKD are diabetes and long-term, uncontrolled hypertension. In further embodiments, a dual agonist peptide product described herein is used to treat fatty liver disease (FLD). In some embodiments, the FLD is non-alcoholic fatty liver disease (NAFLD). In certain embodiments, the NAFLD is non-alcoholic steatohepatitis (NASH). FLD, also known as hepatic steatosis, is characterized by excessive fat accumulation in the liver. FLD includes alcoholic fatty liver disease (AFLD) and NAFLD. Chronic alcoholism causes fatty liver due to production of toxic metabolites such as aldehydes during metabolism of alcohol in the liver. NAFLD is described below. FLD is associated with diabetes, obesity and metabolic syndrome. Fatty liver can develop into cirrhosis or a liver cancer (e.g., hepatocellular carcinoma [HCC]). Less than about 10% of people with cirrhotic AFLD develop HCC, but up to about 45% of people with NASH without cirrhosis may develop HCC. HCC is the most common type of primary liver cancer in adults and occurs in the setting of chronic liver inflammation. NAFLD is characterized by fatty liver that occurs when fat, in particular free fatty acids and triglycerides, accumulates in liver cells (hepatic steatosis) due to causes other than excessive alcohol consumption, such as nutrient overload, high caloric intake and metabolic dysfunction (e.g., dyslipidemia and impaired glucose control). A liver can remain fatty without disturbing liver function, but a fatty liver can progress to become NASH, a condition in which steatosis is accompanied by inflammation, hepatocyte ballooning and cell injury with or without fibrosis of the liver. Fibrosis is the strongest predictor of mortality from NASH. NAFLD can be characterized by steatosis alone; steatosis with lobular or portal inflammation but without ballooning; steatosis with ballooning but without inflammation; or steatosis with inflammation and ballooning. NASH is the most extreme form of NAFLD. NASH is a progressive disease, with about 20% of patients developing cirrhosis of the liver and about 10% dying from a liver disease, such as cirrhosis or a liver cancer (e.g., HCC). NAFLD is the most common liver disorder in developed countries, and NASH is projected to supplant hepatitis C as the major cause of liver transplant in the U.S. by 2020. About 12-25% of people in the U.S. have NAFLD, with NASH affecting about 2-5% of people in the U.S. NAFLD, including NASH, is associated with insulin resistance, obesity and metabolic syndrome. For instance, insulin resistance contributes to progression of fatty liver to hepatic inflammation and fibrosis and thus NASH. Furthermore, obesity drives and exacerbates NASH, and weight loss can alleviate NASH. Therefore, the peptide products described herein, including GLP-1 receptor (GLP1R) agonists, glucagon receptor (GCGR) agonists and dual GLP1R/GCGR agonists, can be used to treat NAFLD, including NASH. In some embodiments, the dual agonist peptide products used to treat a condition associated with insulin resistance or/and obesity disclosed herein, such as NAFLD (e.g., NASH) or PCOS, are selected from the dual agonist peptide products of SEQ. ID. NOs. 1-10, and/or derivatives thereof, and pharmaceutically acceptable salts thereof.

In some embodiments, the present dual agonist peptide(s) can be used to control blood glucose with reduction of one or more adverse events (i.e., an unexpected event that negatively impacts patient and/or animal welfare) as compared to an agonist with unbalanced affinity for UP 1R and GCGR (e.g., semaglutide). Exemplary, non-limiting adverse events can include nausea, vomiting, diarrhea, abdominal pain and/or constipation. Adverse events may also include any known to those of ordinary skill in the art, such as those listed in industry resources and/or otherwise known to those of ordinary skill in the art (see, e.g., Medical Dictionary for Regulatory Activities (MedDRA) Med. Transl. Med. 2018) and/or Clark, M. J. Biomed. Inf., 54, April 2015, pp. 167-173). Such adverse events can be determined in humans using standard techniques as are typically used in clinical trials (e.g., doctor visit, surveys/questionnaires). As compared to the frequency and/or severity of such an adverse event that occurs upon administration of an agonist with unbalanced affinity for GLP-1R and GCGR (e.g., semaglutide) to a subject, the dual agonist peptides of this disclosure (e.g., any of SEQ ID NOS. 1-10, or derivatives thereof) can decrease such frequency and/or severity thereof by, e.g., 20%, 40%, 50%, 60%, 70%, 80%, 90% of higher (up to 100%). In some embodiments, the dual agonist peptides of this disclosure (e.g., any of SEQ ID NOS. 1-10, or derivatives thereof) do not cause any adverse events.

A present dual agonist peptide product can be administered by any suitable route for treatment of a condition disclosed herein. Potential routes of administration of a peptide product include without limitation oral, parenteral (including intradermal, subcutaneous, intramuscular, intravascular, intravenous, intra-arterial, intraperitoneal, intracavitary and topical), and topical (including transdermal, transmucosal, intranasal (e.g., by nasal spray or drop), ocular (e.g., by eye drop), pulmonary (e.g., by oral or nasal inhalation), buccal, sublingual, rectal (e.g., by suppository), and vaginal (e.g., by suppository)). In some embodiments, a peptide product is administered parenterally, such as subcutaneously, intravenously or intramuscularly. In other embodiments, a peptide product is administered by oral inhalation or nasal inhalation or insufflation. The therapeutically effective amount and the frequency of administration of, and the length of treatment with, a peptide product to treat a condition disclosed herein may depend on various factors, including the nature and severity of the condition, the potency of the compound, the route of administration, the age, body weight, general health, gender and diet of the subject, and the response of the subject to the treatment, and can be determined by the treating physician. In some embodiments, a peptide product is administered parenterally (e.g., subcutaneously (sc), intravenously (iv) or intramuscularly (im)) in a dose from about 0.01 mg to about 0.1, 1, 5 or 10 mg, or about 0.1-1 mg or 1-10 mg, over a period of about one week for treatment of a condition disclosed herein (e.g., one associated with insulin resistance or/and obesity, such as NASH or PCOS). In further embodiments, a peptide product is administered parenterally (e.g., sc, iv or im) in a dose of about 0.1-0.5 mg, 0.5-1 mg, 1-5 mg or 5-10 mg over a period of about one week. In certain embodiments, a peptide product is administered parenterally (e.g., subcutaneously (SC), intravenous (IV) or intramuscular (IM)) in a dose of about 0.1-1 mg, or about 0.1-0.5 mg or 0.5-1 mg, over a period of about one week. One of skill in the art understands that an effective dose in a mouse, or other pre-clinical animal model, may be scaled for a human. In that way, through allometric scaling (also referred to as biological scaling) a dose in a larger animal may be extrapolated from a dose in a mouse to obtain an equivalent dose based on body weight or body surface area of the animal.

A peptide product can be administered in any suitable frequency for treatment of a condition disclosed herein (e.g., one associated with insulin resistance or/and obesity, such as NASH or PCOS). In some embodiments, a dual agonist peptide product is administered, e.g., sc or iv once a day, once every two days, once every three days, twice a week, once a week or once every two weeks. In certain embodiments, a peptide product is administered, e.g., SC, IV, or IM once a week. A dual agonist peptide product can be administered at any time of day convenient to the patient. A dual agonist peptide product can be taken substantially with food (e.g., with a meal or within about 1 hour or 30 minutes before or after a meal) or substantially without food (e.g., at least about 1 or 2 hours before or after a meal). The length of treatment of a medical condition with a dual agonist peptide product can be based on, e.g., the nature and severity of the condition and the response of the subject to the treatment, and can be determined by the treating physician. In some embodiments, a dual agonist peptide product is administered chronically to treat a condition disclosed herein, such as at least about 2 months, 3 months, 6 months, 1 year, 1.5 years, 2 years, 3 years, 5 years, 10 years or longer. A dual agonist peptide product can also be taken pro re nata (as needed) until clinical manifestations of the condition disappear or clinical targets are achieved, such as blood glucose level, blood pressure, blood levels of lipids, body weight or body mass index, waist-to-hip ratio or percent body fat, or any combination thereof. If clinical manifestations of the condition re-appear or the clinical targets are not maintained, administration of the dual agonist peptide product can resume. The disclosure provides a method of treating a medical condition described herein, comprising administering to a subject in need of treatment a therapeutically effective amount of a peptide product described herein or a pharmaceutically acceptable salt thereof, or a pharmaceutical composition comprising the same. The disclosure further provides a peptide product described herein or a pharmaceutically acceptable salt thereof, or a composition comprising the same, for use as a medicament. In addition, the disclosure provides for the use of a peptide product described herein or a pharmaceutically acceptable salt thereof in the preparation of a medicament. The medicament containing the peptide product can be used to treat any medical condition described herein. The peptide product can optionally be used in combination with one or more additional therapeutic agents.

A dual agonist peptide product described herein can be administered as the sole active agent, or optionally be used in combination with one or more other dual agonist peptide products, and/or additional therapeutic agents to treat any disorder disclosed herein, such as insulin resistance, diabetes, obesity, metabolic syndrome or a cardiovascular disease, or any condition associated therewith, such as NASH or PCOS. In some embodiments, the one or more additional therapeutic agents are selected from antidiabetic agents, anti-obesity agents (including lipid-lowering agents and pro-satiety agents), anti-atherosclerotic agents, anti-inflammatory agents, antioxidants, antifibrotic agents, anti-hypertensive agents, and combinations thereof. Antidiabetic agents include without limitation: AMP-activated protein kinase (AMPK) agonists, including biguanides (e g., buformin and metformin); peroxisome proliferator-activated receptor gamma (PPAR-γ) agonists, including thiazolidinediones (e.g., balaglitazone, ciglitazone, darglitazone, englitazone, lobeglitazone, netoglitazone, pioglitazone, rivoglitazone, rosiglitazone and troglitazone), MSDC-0602K and saroglitazar (dual PPAR-α/γ agonist); glucagon-like peptide-1 (GLP-1) receptor agonists, including exendin-4, albiglutide, dulaglutide, exenatide, liraglutide, lixisenatide, semaglutide, taspoglutide, CNT0736, CNT03649, HM11260C (LAPS-Exendin), NN9926 (OG9S7GT), TT401 and ZYOG1; dipeptidyl peptidase 4 (DPP-4) inhibitors, including alogliptin, anagliptin, dutogliptin, evogliptin, gemigliptin, gosogliptin, linagliptin, omarigliptin, saxagliptin, septagliptin, sitagliptin, teneligliptin, trelagliptin and vildagliptin; sodium-glucose transport protein 2 (SGLT2) inhibitors, including canagliflozin (also inhibits SGLT1), dapagliflozin, empagliflozin, ertugliflozin, ipragliflozin, luseogliflozin, remogliflozin etabonate, sotagliflozin (also inhibits SGLT1) and tofogliflozin; blockers of ATP-dependent $K^+$ ($KA_{TP}$) channels on pancreatic beta cells, including rneglitinides (e.g., mitiglinide, nateglinide and repagiinide) and sulfonylureas {including first generation (e.g., acetohexamide, carbutamide, chlorpropamide, giycyclamide [tolhexamide], metahexamide, tolazamide and tolbutamide) and second generation (e.g., glibenclamide, glyburide, glibornuride, gliclazide, glimepiride, glipizide, gliquidone, glisoxepide and glyclopyramide); insulin and analogs thereof, including fast-acting insulin (e.g., insulin aspari insulin glulisine and insulin lispro), intermediate-acting insulin (e.g., NPH insulin), and long-acting insulin (e.g., insulin degludec, insulin detemir and insulin glargine); and/or, analogs, derivatives and salts thereof. In certain embodiments, the antidiabetic agent is or includes a biguanide (e.g., metformin), a thiazolidinedione (e.g., pioglitazone or rosiglitazone) or a SGLT2 inhibitor (e.g., empagliflozin or tofogliflozin), or any combination thereof. Anti-obesity agents include, but are not limited to: appetite suppressants (anorectics), including amphetamine, dexamphetamine, amfepramone, clobenzorex, mazindol, phentermine (with or without topiramate) and lorcaserin; pro-satiety agents, including ciliary neurotrophic factor (e.g., axokine) and longer-acting analogs of amylin, calcitonin, cholecystokinin (CCK), GLP-1, leptin, oxyntomodulin, pancreatic polypeptide (PP), peptide YY (PYY) and neuropeptide Y (NPY); lipase inhibitors, including caulerpenyne, cetilistat, ebelactone A and B, esterastin, lipstatin, orlistat, percyquinin, panclicin A-E, valilactone and vibralactone; antihyperlipidemic agents; and analogs, derivatives and salts thereof. Antihyperlipidemic agents include without limitation: HMG-CoA reductase inhibitors, including statins {e.g., atorvastatin, cerivastatin, fluvastatin, mevastatin, monacolins (e.g., monacolin K (lovastatin), pitavastatin, pravastatin, rosuvastatin and simvastatin} and flavanones (e.g., naringenin); squalene synthase inhibitors, including lapaquistat, zaragozic acid and RPR-107393; acetyl-CoA carboxylase (ACC) inhibitors, including anthocyanins, avenaciolides, chloroacetylated biotin, cyclodim, diclofop, haloxyfop, soraphens (e.g., soraphen $A_{1a}$), 5-(tetradecyloxy)-2-furancarboxylic acid (TOFA), CP-640186, GS-0976, NDI-010976; 7-(4-propyloxy-phenylethynyl)-3,3-dimethyl-3,4dihydro-2H-benzo[b][1,4]dioxepine; N-ethyl-N'-(3-{[4-(3,3-dimethyl-1-oxo-2-oxa-7-azaspiro[4.5]dec-7-yl)piperidin-1-yl]-carbonyl}-1-benzothien-2-yl)urea; 5-(3-acetamidobut-1-ynyl)-2-(4-propyloxyphenoxy)thiazole; and 1-(3-{[4-(3,3-dimethyl-1-oxo-2-oxa-7-azaspiro[4.5]dec-7-yl)piperidin-1-yl]-carbonyl}-5-(pyridin-2-yl)-2-thienyl)-3-ethylurea;

PPAR-α agonists, including fibrates (e.g., bezafibrate, ciprofibrate, clinofibrate, clofibric acid, clofibrate, aluminum clofibrate [alfibrate], clofibride, etofibrate, fenofibric acid, fenofibrate, gemfibrozil, ronifibrate and simfibrate), isoflavones (e.g., daidzein and genistein), and perfluoroalkanoic acids (e.g., perfluorooctanoic acid and perfluorononanoic acid); PPAR-δ agonists, including elafibranor (dual PPAR-α/γ agonist), GFT505 (dual PPAR-α/γ agonist), GW0742, GW501516 (dual PPAR-β/δ agonist), sodelglitazar (GW677954), MBX-8025, and isoflavones (e.g., daidzein and genistein); PPAR-γ agonists, including thiazolidinediones {supra), saroglitazar (dual PPAR-α/γ agonist), 4-oxo-2-thioxothiazolines (e.g., rhodanine), berberine, honokiol, perfluorononanoic acid, cyclopentenone prostaglandins (e.g., cyclopentenone 15-deoxy-A-prostaglandin $J_2$ [15d-PGD2]), and isoflavones (e.g., daidzein and genistein); liver X receptor (LXR) agonists, including endogenous ligands (e.g., oxysterols such as 22(i?)-hydroxycholesterol, 24(A)-hydroxy cholesterol, 27-hydroxycholesterol and cholestenoic acid) and synthetic agonists (e.g., acetyl-podocarpic dimer, hypocholamide, A(X-di methyl-3 b-hydroxycholenamide [DMHCA], GW3965 and T0901317); retinoid X receptor (RXR) agonists, including endogenous ligands (e.g., 9-cis-retinoic acid) and synthetic agonists (e.g., bexarotene, AGN 191659, AGN 191701, AGN 192849, BMS649, LG100268, LG100754 and LGD346); inhibitors of acyl-CoA cholesterol acyltransferase (ACAT, aka sterol G-acyl transferase [SOAT], including ACAT1 [SOAT1] and ACAT2 [SOAT2]), including avasimibe, pactimibe, pellitorine, terpendole C and flavanones (e.g., naringenin); inhibitors of stearoyl-CoA desaturase-1 (SCD-1, aka stearoyl-CoA delta-9 desaturase) activity or expression, including aramchol, CAY-10566, CVT-11127, SAR-224, SAR-707, XEN-103; 3-(2-hydroxyethoxy)-4-methoxy-N-[5-(3-trifluoromethylbenzyl)thiazol-2-yl]benzamide and 4-ethylamino-3-(2-hydroxyethoxy)-N-[5-(3-trifluoromethylbenzyl)thiazol-2-yl]benzamide; 1'-{6-[5-(pyridin-3-ylmethyl)-1,3,4-oxadiazol yl]pyridazin-3-yl}-5-(trifluoromethyl)-3,4-dihydrospiro[chromene-2,4'-piperidine]; 5-fluoro-1'-{6-[5-(pyridin-3-ylmethyl)-1,3,4-oxadiazol-2-yl]pyridazin-3-yl}-3,4-dihydrospiro[chromene-2,4'-piperidine]; 6-[5-(cyclopropylmethyl)-4,5-dihydro-1'H,3H-spiro[1,5-benzoxazepine-2,4'-piperidin]-1'-yl]-N-(2-hydroxy-2-pyridin-3-ylethyl)pyridazine-3-carboxamide; 6-[4-(2-methylbenzoyl)piperidin-1-yl]pyridazine-3-carboxylic acid (2-hydroxy-2-pyridin-3-ylethyl)amide; 4-(2-chlorophenoxy)-N-[3-(methylcarbamoyl)phenyl]piperidine-1-carboxamide; the cis-9,trans-11 isomer and the trans-10,cis-12 isomer of conjugated linoleic acid, substituted heteroaromatic compounds disclosed in WO 2009/129625 A1, anti-sense polynucleotides and peptide-nucleic acids (PNAs) that target mRNA for SCD-1, and SCD-1-targeting siRNAs; cholesterylester transfer protein (CETP) inhibitors, including anacetrapib, dalcetrapib, evacetrapib, torcetrapib and AMG 899 (TA-8995); inhibitors of microsomal triglyceride transfer protein (MTTP) activity or expression, including implitapide, lomitapide, dirlotapide, mitratapide, CP-346086, JTT-130, SLx-4090, anti-sense polynucleotides and PNAs that target mRNA for MTTP, MTTP-targeting microRNAs (e.g., miRNA-30c), and MTTP-targeting siRNAs; GLP-1 receptor agonists; fibroblast growth factor 21 (FGF21) and analogs and derivatives thereof, including BMS-986036 (pegylated FGF21); inhibitors of pro-protein eonvertase subtilisin/kexin type 9 (PCSK9) activity or expression, including berberine (reduces PC8K9 level), annexin A2 (inhibits PCSK9 activity), anti-PCSK9 antibodies (e.g., alirocumab, bococizumab, evolocumab, LGT-209, LY3015014 and RG7652), peptides that mimic the epidermal growth factor-A (EGF-A) domain of the LDL receptor which binds to PCSK9, PCSK9-binding adnectins (e.g., BMS-962476), anti-sense polynucleotides and PNAs that target mRNA for PCSK9, and PCSK9-targeting siRNAs (e.g, inclisiran [ALN-PCS] and ALN-PCS02); apolipoprotein mimetic peptides, including apoA-I mimetics (e.g., 2F, 3F, 3F-1, 3F-2, 3F-14, 4F, 4F-P-4F, 4F-IHS-4F, 4F2, 5F, 6F, 7F, 18F, 5A, SA-C1, 5A-CH1, 5A-CH2, 5A-H1, 18 A, 37 pA [18A-P-18A], ELK, ELK-1A, ELK-1F, ELK-1K1A1E, ELK-1L1K, ELK-1W, ELK-2A, ELK-2A2K2E, ELK-2E2K, ELK-2F, ELK-3 E3EK, ELK-3E3K3A, ELK-3E3LK, ELK-PA, ELK-P2A, ELKA, ELKA-CH2, ATI-5261, CS-6253, ETC-642, FAMP, FREL and KRES and apoE mimetics (e.g., Ac-hEl8A-NH$_2$, AEM-28, Ac-[R]hEl 8 A-NH$_2$, AEM-28-14, EpK, hEp, mR18L, COG-112, COG-133 and COG-1410); omega-3 fatty acids, including docosahexaenoic acid (DHA), docosapentaenoic acid (DPA), eicosapentaenoic acid (EPA), a-linolenic acid (ALA), fish oils (which contain, e.g., DHA and EPA), and esters (e.g., glyceryl and ethyl esters) thereof; and analogs, derivatives and salts thereof. In certain embodiments, the anti-obesity agent is or includes a lipase inhibitor (e.g., orlistat) or/and an antihyperlipidemic agent (e.g., a statin such as atorvastatin, or/and a fibrate such as fenofibrate). Antihypertensive agents include without limitation: antagonists of the renin-angiotensin-aldosterone system (RAAS), including renin inhibitors (e.g., aliskiren), angiotensin-converting enzyme (ACE) inhibitors (e.g., benazepril, captopril, enalapril, fosinopril, lisinopril, moexipril, perindopril, quinapril, ramipril and trandolapril), angiotensin II receptor type 1 (ATII1) antagonists (e.g., azilsartan, candesartan, eprosartan, fimasartan, irbesartan, losartan, olmesartan medoxomil, olmesartan, telmisartan and valsartan), and aldosterone receptor antagonists (e.g., eplerenone and spironolactone); diuretics, including loop diuretics (e.g., bumetanide, ethacrynic acid, furosemide and torsemide), thiazide diuretics (e.g., bendroflumethiazide, chlorothiazide, hydrochlorothiazide, epitizide, methyclothi azide and polythiazide), thiazide-like diuretics (e.g., chlorthalidone, indapamide and metolazone), cicletanine (an early distal tubular diuretic), potassium-sparing diuretics (e.g., amiloride, eplerenone, spironolactone and triamterene), and theobromine; calcium channel blockers, including dihydropyridines (e.g., amlodipine, levamlodipine, cilnidipine, clevidipine, felodipine, isradipine, lercanidipine, nicardipine, nifedipine, nimodipine, nisoldipine and nitrendipine) and non-dihydropyridines (e.g., diltiazem and verapamil); α$_2$-adrenoreceptor agonists, including clonidine, guanabenz, guanfacine, methyldopa and moxonidine; α1-adrenoreceptor antagonists (alpha blockers), including doxazosin, indoramin, nicergoline, phenoxybenzamine, phentolamine, prazosin, terazosin and tolazoline; β-adrenoreceptor (β1 or/and β2) antagonists (beta blockers), including atenolol, betaxolol, bisoprolol, carteolol, carvedilol, labetalol, metoprolol, nadolol, nebivolol, oxprenolol, penbutolol, pindolol, propranolol and timolol; mixed alpha/beta blockers, including bucindolol, carvedilol and labetalol; endothelin receptor antagonists, including selective ETA receptor antagonists (e.g., ambrisentan, atrasentan, edonentan, sitaxentan, zibotentan and BQ-123) and dual ETA/ET$_B$ antagonists (e.g., bosentan, macitentan and tezosentan); other vasodilators, including hydralazine, minoxidil, theobromine, sodium nitroprusside, organic nitrates (e.g., isosorbide mononitrate, isosorbide dinitrate and nitroglycerin, which are converted to nitric oxide in the body), endothelial nitric oxide synthase (eNOS) stimulators (e.g., cicletanine), activators of soluble guanylate cyclase (e.g., cinaciguat and riociguat), phosphodiesterase type 5 (PDE5) inhibitors (e.g., avanafil, benzamidenafil, dasantafil, dynafil, lodenafil, mirodenafil, sildenafil, tadalafil, udenafil, vardenafil, dipyridamole, papaverine, propentofylline, zaprinast and T-1032), prostaglandin Ei (alprostadil) and analogs thereof (e.g., limaprost amd misoprostol), prostacyclin and analogs thereof (e.g., ataprost, beraprost [e.g., esuberaprost], 5,6,7-trinor-4,8-inter-w-phenylene-9-fluoro-PGl$_2$, carbacyclin, isocarbacyclin, clinprost, ciprostene, eptaloprost, cicaprost, iloprost, pimilprost, SM-10906 (des-methyl pimilprost), naxaprostene, taprostene, treprostinil, CS-570, OP-2507 and TY-11223), non prostanoid prostacyclin receptor agonists (e.g., 1-phthalazinol, ralinepag, selexipag, ACT-333679 [MRE-269, active metabolite of selexipag], and TRA-418), phospholipase C (PLC) inhibitors, and protein kinase C (PKC) inhibitors (e.g., BIM-1, BIM-2, BIM-3, BIM-8, chelerythrine, cicletanine, gossypol, miyabenol C, myricitrin, ruboxistaurin and verbascoside; minerals, including magnesium and magnesium sulfate; and analogs, derivatives and salts thereof. In certain embodiments, the antihypertensive agent is or includes a thiazide or thiazide like diuretic (e.g., hydrochlorothiazide or chlorthalidone), a calcium channel blocker (e.g., amlodipine or nifedipine), an ACE inhibitor (e.g., benazepril, captopril or perindopril) or an angiotensin II receptor antagonist (e.g., olmesartan medoxomil, olmesartan, telmisartan or valsartan), or any combination thereof. In some embodiments, a peptide product described herein is used in combination with one or more additional therapeutic agents to treat NAFLD, such as NASH. In some embodiments, the one or more additional therapeutic agents are selected from antidiabetic agents, anti-obesity agents, anti-inflammatory agents, antifibrotic agents, antioxidants, anti hypertensive agents, and combinations thereof. Therapeutic agents that can be used to treat NAFLD (e.g., NASH) include without limitation: PPAR agonists, including PPAR-δ agonists (e.g., MBX-8025, elafibranor [dual PPAR-α/δ agonist] and GW501516 [dual PPAR-β/δ agonist]) and PPAR-γ agonists (e.g., thiazolidinediones such as pioglitazone, and saroglitazar [dual PPAR-α/γ agonist])—PPAR-δ and -γ agonism increases insulin sensitivity, PPAR-α agonism reduces liver steatosis and PPAR-δ agonism inhibits activation of macrophages and Kupffer cells; farnesoid X receptor (FXR) agonists, such as obeticholic acid and nonsteroidal FXR agonists like GS-9674 reduce liver gluconeogenesis, lipogenesis, steatosis and fibrosis; fibroblast growth factor 19 (FGF19) and analogs and derivatives thereof, such as NGM-282-FGF19 analogs reduce liver gluconeogenesis and steatosis; fibroblast growth factor 21 (FGF21) and analogs and derivatives thereof, such as BMS-986036 (pegylated FGF21)—FGF21 analogs reduce liver steatosis, cell injury and fibrosis; HMG-CoA reductase inhibitors, including statins (e.g., rosuvastatin)—statins reduce steatohepatitis and fibrosis; ACC inhibitors, such as NDI-010976 (liver-targeted) and GS-0976—ACC inhibitors reduce de novo lipogenesis and liver steatosis; SCD-1 inhibitors, such as aramchol—SCD-1 inhibitors reduce liver steatosis and increase insulin sensitivity; SGLT2 inhibitors, such as canagliflozin, ipragliflozin and luseogliflozin—SGLT2 inhibitors reduce body weight, liver ALT level and fibrosis; antagonists of CCR2 or/and CCR5, such as cenicriviroc—antagonists of CCR2 (binds to CCL2 [MCP1]) and CCR5 (binds to CCL5 [RANTES]) inhibit activation and migration of inflammatory cells (e.g., macrophages) to the liver and reduce liver fibrosis; apoptosis inhibitors, including apoptosis signal-regulating kinase 1 (ASK1) inhibitors (e.g., selonsertib) and caspase inhibitors (e.g., emricasan [pan-caspase inhibitor])—apoptosis inhibitors reduce liver steatosis and fibrosis; lysyl oxidase-like 2 (LOXL2) inhibitors, such as simtuzumab—LOXL2 is a key matrix enzyme in collagen formation and is highly expressed in the liver; galectin-3 inhibitors, such as GR-MD-02 and TD139—galectin-3 is critical for development of liver fibrosis; antioxidants, including vitamin E (e.g., a-tocopherol) and scavengers of reactive oxygen species (ROS) and free radicals (e.g., cysteamine, glutathione, melatonin and pentoxifylline [also anti-inflammatory via inhibition of TNF-a and phosphodiesterases])—vitamin E reduces liver steatosis, hepatocyte ballooning and lobular inflammation; and, analogs, derivatives and salts thereof. In some embodiments, a peptide product described herein is used in conjunction with a PPAR agonist (e.g., a PPAR-δ agonist such as elafibranor or/and a PPAR-γ agonist such as pioglitazone), a HMG-CoA reductase inhibitor (e.g., a statin such as rosuvastatin), an FXR agonist (e.g., obeticholic acid) or an antioxidant (e.g., vitamin E), or any combination thereof, to treat NAFLD (e.g., NASH). In certain embodiments, the one or more additional therapeutic agents for treatment of NAFLD (e.g., NASH) are or include vitamin E or/and pioglitazone. Other combinations may also be used as would be understood by those of ordinary skill in the art.

Pharmacokinetic ("PK") parameters can be estimated using Phoenix® WinNonlin® version 8.1 or higher (Certara USA, Inc., Princeton, New Jersey). A non-compartmental approach consistent with the extravascular route of administration can be used for parameter estimation. The individual plasma concentration-time data can be used for pharmacokinetic calculations. In addition to parameter estimates for individual animals, descriptive statistics (e.g. mean, standard deviation, coefficient of variation, median, min, max) can be determined, as appropriate. Concentration values that are below the limit of quantitation can be treated as zero for determination of descriptive statistics and pharmacokinetic analysis. Embedded concentration values that are below the limit of quantitation can be excluded from pharmacokinetic analysis. All parameters can be generated from individual dual agonist peptide (or derivatives and/or metabolites thereof) concentrations in plasma from test article-treated groups on the day of dosing (Day 1). Parameters can be estimated using nominal dose levels, unless out of specification dose formulation analysis results are obtained, in which case actual dose levels can be used. Parameters can be estimated using nominal sampling times; if bioanalytical sample collection deviations are documented, actual sampling times can be used at the affected time points. Bioanalytical data can be used as received for the pharmacokinetic analysis and can be presented in tables and figures in the units provided. Pharmacokinetic parameters can be calculated and presented in the units provided by the analytical laboratory (the order of magnitude can be adjusted appropriately for presentation in the report, e.g. h*ng/mL converted to h*μg/mL). Descriptive statistics (e.g., mean, standard deviation, coefficient of variation, median, min, max) and pharmacokinetic parameters can be determined to three significant figures, as appropriate. Additional data handling items can be documented as needed. PK parameters to be determined, as data permit, can include but are not limited to the following: $C_{max}$: Maximum observed concentration; DN $C_{max}$: dose normalized maximum concentration, calculated as $C_{max}$/dose; $T_{max}$: time of maximum observed concentration; $AUC_{0-t}$: area under the curve from time 0 to the time of the last measurable concentration, calculated using the linear trapezoidal rule; $AUC_{0-96}$: area under the curve from time 0 to hour 96, calculated using the linear trapezoidal rule; DN $AUC_{0-96}$: dose normalized $AUC_{0-96}$, calculated as $AUC_{0-96}$/dose; $AUC_{0-inf}$: area under the curve from time 0 to infinity (Day 1 only), calculated as $AUC_{0-inf}=AUC_{0-t}+C_t/\lambda_z$, where $C_t$ is the last observed quantifiable concentration and $\lambda_z$ is the elimination rate constant; $t_{1/2}$: elimination half-life, calculated as $\ln(2)/\lambda_z$. Additional parameters and comparisons (e.g., sex ratios, dose proportionality ratios, etc.) can also be determined, as would be understood by those of ordinary skill in the art.

In some embodiments, this disclosure provides pharmaceutical dosage formulation(s) comprising at least one dual agonist peptide with affinity for glucagon-like peptide 1 receptor (GLP-1R) and glucagon receptor (GCGR) wherein: the peptide is modified with a hydrophobic surfactant; the dosage is configured to control blood glucose and/or induce weight loss, with reduction of one or more adverse events as compared to an agonist with unbalanced affinity for GLP-1R and GCGR, the adverse events being selected from nausea, vomiting, diarrhea, abdominal pain and constipation, upon administration to a mammal. In some embodiments, the dual agonist peptide is any one of SEQ ID NOS: 1-10, or a derivative thereof, or a combination thereof. In some embodiments, the dual agonist peptide has about equal affinity for GLP-1R and GCGR, and in even more preferred embodiments is SEQ ID NO: 1. In some embodiments, administration of the dual agonist peptide to a mammal, as compared to administration of an approximate equimolar dosage of semaglutide, results in: lower blood glucose at about 48 or 96 hours following administration (optionally at least about any of 10, 20, 30, 40, or 50% lower, preferably at least about 50% lower); lower blood glucose at about 72 hours following administration (optionally at least about any of 10, 20, 30, 40, 50, 60, 70, 80, 90, or 100% lower, preferably at least about 100% lower); and/or, lower blood glucose at about 120 hours following administration. In some embodiments, administration of the dual agonist peptide to a mammal, as compared to administration of an approximate equimolar dosage of semaglutide, induces whole-body weight loss; and/or, induces liver weight loss. In some embodiments, administration of the dual agonist peptide to a mammal, as compared to administration of an approximate equimolar dosage of semaglutide, exhibits a lower Cmax (optionally at least about any of 10, 20, 30, 40, 50% lower, preferably at least about 50% lower); exhibits approximately equal or greater $T_{max}$ (optionally at least about any of 10, 20, 30, 40, 50, 60, 70, 80, 90, or 100% greater, preferably at least about 100% greater); exhibits a similar $AUC_{(0-inf)}$ (optionally at least about any of 50, 60, 70, 80, 90, 95, 100% thereof, preferably at least about 80-90% thereof, such as about 85-93% thereof); exhibits about an equal or higher $T_{1/2\ (hr)}$ (optionally at least about any of 10, 20, 30, 40, 50, 60, 70, 80, 90, or 100% thereof, preferably at least about 50 or 75% thereof, such as about 50-75% thereof); exhibits a prolonged MRT (hr) (optionally at least about any of 10, 20, 30, 40, or 50% higher, preferably at least about 25% higher); exhibits a protracted PK/PD profile; exhibits equal or greater glucoregulatory effects; induces greater whole-body weight loss, optionally about twice thereof; induces lower body fat mass, optionally about any of 10, 20, 30, 40, 50, 60, 70, 80, 90, or 100% lower, preferably at least about 100% lower); and/or, when administered to treat NASH induces increased whole-body weight reduction, liver weight loss, improved NAS score, improved hepatosteatosis, improved ballooning, improved col1A1 staining, improved ALT, improved liver TG/TC, and improved plasma TG/TC. In some embodiments, administration of the dual agonist peptide to a mammal, as compared to administration of an approximate equimolar dosage of semaglutide, results in greater loss in body weight by approximately 14 days following administration of the dosage formulation (optionally at least about 10, 20, 30, 40 or 50% greater, preferably at least about 15% greater); and/or, greater loss in body weight by approximately 20-28 days following administration of the dosage formulation (optionally at least about any of 10, 20, 30, 40, or 50% greater, preferably at least about 25% greater). In some embodiments, administration of the dual agonist peptide to a mammal, as compared to administration of an approximate equimolar dosage of semaglutide, results in weight loss in an obese mammal sufficient to return the mammal the normal weight range of a lean normal mammal.

"Reducing," or "reduction of" adverse effects or events refers to a reduction in the degree, duration, and/or frequency of adverse effects experienced by a subject and incidence in a group of subjects following administration of an agonist with about balanced affinity to GLP1R and GCGR compared to an agonist with unbalanced affinity for GLP1R and GCGR. Such reduction encompasses the prevention of some adverse effects that a subject would otherwise experience in response to an agonist with unbalanced affinity to GLP1R and GCGR. Such reduction also encompasses the elimination of adverse effects previously experienced by a subject following administration of an agonist with unbalanced affinity to GLP1R and GCGR. In some embodiments, "reducing," or "reduction of" adverse effects encompass a reduction of gastrointestinal side effects wherein the adverse events are reduced to zero or undetectable levels. In other embodiments, adverse effect is reduced to level equivalent to untreated subjects but not completely eliminated. Moreover, administration of analogs with unbalanced affinity toward GLP-1R or GCGR to a mammal may lead to the need for an excessively high dose to maximally activate the receptor with weaker sensitivity toward the ligand, thus leading to a potential for exceeding the biologically effective dose level for the other ligand and causing dose-related, undesired side effects.

This disclosure also provides methods for lowering and/or stabilizing the blood glucose of a mammal, the method comprising administering a pharmaceutical dosage formulation comprising a dual agonist peptide of SEQ ID NOS. 1-10 (or a derivative thereof), preferably a dual agonist peptide with about equal affinity for GLP-1R and GCGR (preferably SEQ ID NO: 1), to a mammal, wherein the method reduces the incidence of, or the severity of, one of more adverse events as compared to an agonist with unbalanced affinity for GLP-1R and GCGR (e.g., semaglutide), the adverse events being selected from nausea, vomiting, diarrhea, abdominal pain and constipation, upon administration to a mammal. In some embodiments, such methods, as compared to a method in which an approximate equimolar dosage of semaglutide is administered, result in lower blood glucose (10, 20, 30, 40, 50, 60, 70, 80, 90, or 100% lower, preferably at least about 50% lower) at approximately 48 or 96 hours following administration, lower blood glucose at approximately 72 hours following administration (optionally at least about any of 10, 20, 30, 40, 50, 60, 70, 80, 90, or 100% lower, preferably at least about 100% lower), and/or, lower blood glucose at approximately 120 hours following administration (optionally at least about any of 10, 20, 30, 40, 50, 60, 70, 80, 90, or 100% lower, preferably at least about 100% lower); induces whole-body weight loss and/or induces liver weight loss; a lower Cmax (optionally about 10, 20, 30, 40, 50, 60, 70, 80, 90, or 100% lower, preferably at least about 50% lower), approximately equal or greater $T_{max}$ (optionally about 10, 20, 30, 40, 50, 60, 70, 80, 90, or 100% lower, preferably at least about 100% greater $T_{max}$), a similar $AUC_{(0-inf)}$ (optionally at least about any of 50, 60, 70, 80, 90, 95, 100% thereof, preferably at least about 80-90% thereof, such as about 85-93% thereof), approximately equal or greater $T_{1/2\ (hr)}$ (optionally at least about any of 10, 20, 30, 40, 50, 60, 70, 80, 90, or 100% lower, preferably at least about 50 or 75% thereof, or about 50-75% thereof); a prolonged MRT (hr) (optionally prolonged by at least about any of 10, 20, 30, 40, 50, 60, 70, 80, 90, or 100%, preferably at least about 25%); a protracted PK/PD profile; equal or greater glucoregulatory effects; greater whole-body weight loss (optionally about twice the whole-body weight loss); lower body fat mass (optionally at least about any of 10, 20, 30, 40, 50, 60, 70, 80, 90, or 100% lower, preferably at least about 100% lower); greater loss in body weight by approximately 14 days following administration of the dosage formulation (optionally at least about any of 10, 20, 30, 40, 50, 60, 70, 80, 90, or 100% greater, preferably at least about 15% greater); greater loss in body weight by approximately 20-28 days following administration of the dosage formulation (optionally at least about any of 10, 20, 30, 40, 50, 60, 70, 80, 90, or 100% greater, preferably at least about 25% greater); and/or, weight loss in an obese mammal sufficient to return the weight of the mammal to the normal weight range of a lean normal mammal; and/or, when the method is for treating NASH, increased whole-body weight reduction, liver weight loss, improved NAS score, improved hepatosteatosis, improved ballooning, improved col1A1 staining, improved ALT, improved liver TG/TC, and improved plasma triglycerides (TG)/total cholesterol (TC).

In some embodiments, this disclosure provides pharmaceutical dosage formulations comprising an agonist peptide product (e.g., SEQ ID NO: 1) and about 0.025-0.075% (w/w) polysorbate 20, about 0.2-0.5% (w/w) arginine, about 3-6% (w/w) mannitol in deionized water (pH 7.7±0.1). In preferred embodiments, the pharmaceutical dosage formulation is ALT-801 comprising SEQ ID NO: 1, about 0.050% (w/w) polysorbate 20, about 0.348% (w/w) arginine, and about 4.260% (w/w) mannitol in deionized water (pH 7.7±0.1).

In some embodiments, this disclosure provides pharmaceutical dosage formulations configured for administering to the mammal the agonist peptide product (e.g., SEQ ID NO: 1) at less than about 0.15 mg/kg/dose, optionally from about 0.03 to 0.10 mg/kg/dose. In some embodiments, the pharmaceutical dosage formulation is configured to administer less than 0.15 mg/kg/dose of the agonist peptide product to the mammal. In some embodiments, the pharmaceutical dosage formulation configured to administer between 0.03-0.15 mg/kg/dose. In some embodiments, the pharmaceutical dosage formulation can be configured to administer between about 0.5 to about 10 mg per week; optionally about 1 to about 7 mg per week; or optionally about 1 to 5 mg per week. In some embodiments, the pharmaceutical dosage formulation is configured to be administered to the mammal once weekly for up to six weeks. In some embodiments, this disclosure provides pharmaceutical dosage formulations configured such that the time to reach a therapeutic dose is about four weeks or less. In some embodiments, the therapeutic dose exhibits a $C_{max}$ of from about 400 to about 1300 ng/ml; a $T_{max}$ of from about 10 to about 36 hours; and/or, an $AUC_{0-48}$ of from about 15,000 to 45,000 h*ng/mL.

In some embodiments, this disclosure provides methods for lowering the blood glucose and/or lowering the body weight of a human being, the method comprising administering to the human being a pharmaceutical dosage formulation comprising SEQ ID NO: 1, wherein the occurrence of one or more adverse events is decreased as compared to an agonist with unbalanced affinity for GLP-1R and GCGR, the adverse events being selected from nausea, vomiting, diarrhea, abdominal pain and constipation, upon administration to a mammal. In some embodiments, the methods: a) reduces the incidence of one of more adverse events as compared to an agonist with unbalanced affinity for GLP-1R and GCGR, the adverse events being selected from nausea, vomiting, diarrhea, abdominal pain and constipation, upon administration to a mammal; b) as compared to a method in which an approximate equimolar dosage of semaglutide is administered, results in: approximately 50% lower blood glucose at approximately 48 or 96 hours following administration, approximately 100% lower blood glucose at approximately 72 hours following administration, and/or, lower blood glucose at approximately 120 hours following administration; c) induces whole-body weight loss and/or induces liver weight loss; d) as compared to a method in which an approximate equimolar dosage of semaglutide is administered, results in: a lower Cmax or optionally about 50% lower Cmax; approximately equal or greater $T_{max}$ or optionally about 100% greater $T_{max}$; a similar AUC(0-inf) or optionally approximately 85-93% $AUC_{(0-inf)}$; approximately equal or lesser T½(hr) or optionally approximately 50-75% $T_{1/2}$ (hr); a prolonged MRT (hr) or optionally at least approximately 25% higher MRT (hr); a protracted PK/PD profile, exhibits equal or greater glucoregulatory effects; greater whole-body weight loss or optionally approximately twice the whole-body weight loss; lower body fat mass, optionally about 100% lower the body fat mass; and/or, increased whole-body weight reduction, liver weight loss, improved NAS score, improved hepatosteatosis, improved ballooning, improved col1A1 staining, improved ALT, improved liver TG/TC, and improved plasma TG/TC, when the method is treats NASH; e) as compared to semaglutide administered at an approximately equimolar dose: results in greater loss in body weight by approximately 14 days following administration of the dosage formulation, optionally about 15% greater; and/or, results in greater loss in body weight by approximately 20-28 days following administration of the dosage formulation, optionally about 25% greater; and/or, f) weight loss in an obese mammal sufficient to return the weight of the mammal to the normal weight range of a lean normal mammal. In preferred embodiments, the methods are for inducing weight loss.

In some embodiments, the methods disclosed herein do not comprise a treatment initiation phase. In other words, the first administered dose is therapeutic without the need to titrate to avoid adverse gastrointestinal side effects. For instance, in some embodiments, the method can comprise administering a first one or more doses (the treatment initiation phase) of a peptide of this disclosure, such as SEQ ID NO: 1, followed by subsequent second one or more and higher doses of the peptide, each of the first and second doses being administered for one or more weeks. In some embodiments, the first dose(s) and the second dose(s) can be followed by one or more third doses that can be higher than the second dose(s). The switch from the first dose, the second dose, and the third dose can be made on a weekly basis. For instance, if it appears the first dose has not induced lower blood glucose and/or weight loss after one or more weeks, the second higher dose can then be administered for one or more weeks followed by an analysis of the effects of the second dose(s). If the beneficial effects are observed (e.g., lower blood glucose and/or body weight), the second dose can continue to be administered. If the beneficial effects are not observed, the third dose may be administered for one or more weeks, followed by a determination of beneficial effects. This cycle of dosing and analysis can be repeated as appropriate, provided adverse events are not observed with each dose. In some embodiments, the subsequent second one or more and higher doses of the peptide can be administered because glycemic control (e.g., decreased blood glucose) was not achieved after about four weeks of administration of the first one or more doses. In some embodiments, the first one or more doses can be administered without the intention to produce a therapeutic effect (e.g., decreased blood glucose and/or weight loss). In some embodiments, however, the methods can be carried out without including the treatment initiation phase.

In some embodiments, the methods can be a first line indication for blood glucose control and/or weight loss in a human being, meaning that it is the first and sole active agent administered to the patient for the purpose of controlling blood glucose and/or inducing weight loss in the human being. In some embodiments, the methods disclosed herein can include an adjunct treatment of diet and/or exercise. In such embodiments, the human being can be administered the pharmaceutical dosage and provided with instructions regarding diet and/or exercise that can enhance the beneficial effects of the pharmaceutical dosage. In some embodiments, the human being to whom the pharmaceutical dosage is administered has type 2 diabetes mellitus. In some embodiments, the human being can exhibit established cardiovascular disease, with or without type 2 diabetes mellitus.

In some embodiments, the pharmaceutical dosage is administered about weekly. In some embodiments, the pharmaceutical dosage is administered to the human being about weekly from about 2 weeks to about 8 weeks, or longer. In some embodiments, the pharmaceutical dosage administered to the human being as a weekly dose for about 4 to about 8 weeks, optionally about 6 weeks, as compared to administration of an approximate equimolar dosage of semaglutide results in greater whole-body weight loss at about 1 week, about 2 weeks, about 3 weeks, about 4 weeks, about 5 weeks, about 6 weeks, or about 7 weeks following administration to the human being. In some embodiments, the pharmaceutical dosage is administered on about days 1, 8, 15, 22, 29, and 36. In some embodiments, the methods can include administration to the human being of a single dose, as compared to administration of an approximate equimolar dosage of semaglutide, results in lower blood glucose at about 1 day, about 2 days, about 3 days, about 4 days, about 5 days, about 6 days or about 7 days following administration. In some embodiments, the methods can include administration to human being of a weekly dose for about 4 to about 8 weeks, optionally about 6 weeks, as compared to administration of an approximate equimolar dosage of semaglutide, results in greater whole-body weight loss at about 1 week, about 2 weeks, about 3 weeks, about 4 weeks, about 5 weeks, about 6 weeks or about 7 weeks following administration. In some embodiments, the methods can include administration to the human being of a single dose, as compared to administration of an approximate equimolar dosage of semaglutide, exhibits a lower $C_{max}$ at about 1 day, about 2 days, about 3 days, about 4 days, about 5 days, about 6 days or about 7 days following administration. In some embodiments, the methods can include administering the pharmaceutical dosage to an adult human at from about 0.5 mg/dose, about 1.0 mg/dose, about 1.5 mg/dose, about 2.0 mg/dose, about 2.5 mg/dose, about 3.0 mg/dose, about 3.5 mg/dose, about 4.0 mg/dose, about 4.5 mg/dose, about 5.0 mg/dose, or about 5.5 mg/dose. In some embodiments, the pharmaceutical dosage can be administered about once per week or once every two weeks, optionally for at least one month; optionally wherein each dose comprises about the same amount of agonist peptide product. In some embodiments, the pharmaceutical dosage can be administered subcutaneously. In some embodiments, one or more of the doses can be administered via a first route (e.g., subcutaneously) and subsequently administered by a different route (e.g., orally). In some embodiments, the time to reach a therapeutic dose is about four weeks or less. In some embodiments, administration of the pharmaceutical dosage formulation exhibits a $C_{max}$ of from about 400 to about 1300 ng/ml; a $T_{max}$ of from about 10 to about 36 hours; and/or, an $AUC_{0-48}$ of from about 15,000 to 45,000 h*ng/mL. In preferred embodiments, the weight loss in the human being is at least 5%, at least 10%; or from about 1% to about 20%; or from about 5% to about 10% (w/w). In some embodiments, administration of a pharmaceutical dosage formulation comprising about 1.8 mg SEQ ID NO: 1 is administered (preferably subcutaneously) once per week for at least six weeks results in greater than about 3-5% whole-body weight loss, preferably greater than about 5% over a population to whom the formulation was administered ("mean weight loss"), and/or a net change from placebo of about 6%, preferably about 6.3%. In some embodiments, administration of a pharmaceutical dosage formulation comprising about 1.2 mg SEQ ID NO: 1 is administered (preferably subcutaneously) once per week for at least six weeks results in about 2% whole-body weight loss, preferably about 1.8% over a population to whom the formulation was administered ("mean weight loss"), and/or a net change from placebo of about 3%, preferably about 2.7%. This disclosure also provides the additional results shown in Table 7 (weight loss) and/or Table 8 (adverse events), which are also preferred embodiments. In some embodiments, administration thereof to a mammal results weight loss in an obese mammal sufficient to return the human being the normal weight range of a lean normal human being. In some embodiments, the pharmaceutical dosage form is an aqueous formulation comprising one or more of polysorbate 20, Arginine, or Mannitol.

Other aspects of this disclosure are also contemplated as will be understood by those of ordinary skill in the art.

Unless defined otherwise or clearly indicated otherwise by their use herein, all technical and scientific terms used herein have the same meaning as commonly understood by those of ordinary skill in the art to which this application belongs. As used in the specification and the appended claims, the word "a" or "an" means one or more. As used herein, the word "another" means a second or more. The acronym "aka" means also known as. The term "exemplary" as used herein means "serving as an example, instance or illustration". Any embodiment or feature characterized herein as "exemplary" is not necessarily to be construed as preferred or advantageous over other embodiments or features. In some embodiments, the term "about" or "approximately" means within ±10% or 5% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values. Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed. Optional or optionally means that the subsequently described event or circumstance can or cannot occur, and that the description includes instances where the event or circumstance occurs and instances where it does not. All publications, patents, and patent applications mentioned in this specification are herein incorporated by reference in their entireties to the same extent as if each individual publication, patent, or patent application was specifically and individually indicated to be incorporated by reference.

Certain embodiments are further described in the following examples. These embodiments are provided as examples only and are not intended to limit the scope of the claims in any way.

EXAMPLES

Example 1. Peptide Synthesis

There are many standard protecting groups and coupling agents that can be successfully used for typical N-alpha-Fmoc based peptide synthesis. Typical examples are listed in U.S. Pat. No. 9,856,306 B2, which is incorporated by reference in its entirety into this disclosure. Further examples can be found in many reviews and protocols, for example those published and routinely updated online by Novabiochem and more specialist reviews (for example Behrendt, R., et al. (2015) J Peptide Sci 22: 4-27 and references therein). Typical commercial protocols used by many contract peptide synthesis houses were used for the synthesis herein. More specialized protocols are given below.

Preparation of C-Terminal Amide Analogs—SEQ. ID. NO. 1.

A sample of Boc-His(Trt)-Aib-Gln(Trt)-Gly-Thr(tBu)-Phe-Thr(tBu)-Ser(tBu)-Asp(tBu)-Tyr(tBu)-Ser(tBu)-Lys (Boc)-Tyr(tBu)-Leu-Asp(tBu)-Glu*-Lys(ivDDE)-Ala-Ala-Lys*-Glu(tBu)  Phe-Ile-Gln(Trt)-Trp(Boc)-Leu-Leu-Gln(Trt)-Thr(tBu)-Rink amide resin (SEQ ID NO:1) was prepared by sequential addition of N-alpha-Fmoc protected amino acids using standard coupling protocols, e.g. diisopropylcarbodiimide (DIC)/hydroxybenztriazole (HBT) couplings, followed by standard deprotection with piperazine, next step coupling, etc. (Glu* and Lys* indicate a side chain cyclic lactam linkage, achieved through deprotection of the allyl-based side chain protection using Pd(PPh$_3$)$_4$/1,3-dimethylbarbituric acid catalysis, washing with DIPEA in NMP and with 0.5% sodium diethyldithiocarbamate trihydrate and DIPEA, then coupling with DIC/Oxyma). Deprotection of the ivDDE group on Lys-N-epsilon position at residue 17 by incubation with 2% or more hydrazine hydrate in DMF, followed by washing by DMF/CH$_2$Cl$_2$, the Lys side chain was acylated with tert-butyl 18-([beta-D-glucuron-1-yl]oxy) octadecanoate in DMF/CH$_2$Cl$_2$ through the use of DIC/HBt or other coupling agents. Completion of the coupling was checked by ninhydrin and the product was washed extensively with CH$_2$Cl$_2$.

The product resin is submitted to final deprotection and cleavage from the resin by treatment with the cleavage cocktail (94% TFA; 2% EDT; 2% H$_2$O; 2% TIS) for a period of 240 min at room temperature. The mixture was treated with Et$_2$O, to precipitate the product and washed extensively with Et$_2$O to yield the crude title peptide product after drying in vacuo.

Purification is carried out in batches by reversed phase (C18) hplc. The crude peptide was loaded on a 4.1×25 cm hplc column at a flow rate of about 15 mL/min (CH$_3$CN organic modifier in aqueous trifluoroacetic acid 0.1%, buffer A; CH$_3$CN with 0.1% TFA, Buffer B) and eluted with a gradient from 40-70% buffer B. The product fraction is lyophilized to yield the title product peptide (SEQ. ID NO: 1) with a purity >94% by analytical hplc (10.5 min; 40-70% CH$_3$CN in 0.1% TFA)/mass spectrometry (M+1 peak=1937.44; molecular weight found 3872.88). In a similar manner, using the glucuronic or melibiouronic acids prepared as indicated in the examples, were prepared the other analogs of the invention.

Analytical data is shown in Table A:

TABLE A

| SEQ ID NO: | Expected MW | Found (M$^+$2) | k' value; hplc gradient | Column |
|---|---|---|---|---|
| 1. | 3873.34 | 3872.94 | 3.0; 40-70% B in 20 min | Luna C-18 5 μ |
| 2. | 3977.47 | 3977.67 | 3.8; 45-75% B in 20 min | Luna C-18 5 μ |
| 3. | 3845.28 | 3845.16 | 3.1; 40-70% B in 20 min | Luna C-18 5 μ |
| 4. | 3873.34 | 3873.46 | 6.5; 40-70% B in 20 min | PLRP-S 8 μ |

Compounds are analyzed by HPLC/MS to provide purity data and identity data (molecular ion detection). The HPLC technique utilizes analytical columns packed with the materials listed, of particle size listed and the data is reported here as k' values (k'=(Tr-T$_0$)/T$_0$) which are expected to be largely independent of system configuration and dead volume, but dependent on gradient and packing material. All compounds were reported to be circa 95% pure.

The corresponding 1-methyl and 1-octyl analogs of the title compound are prepared in a similar manner, but using the reagents 1'-methyl β-D-glucuronic acid and 1'-octyl β-D-glucuronic acid (Carbosynth). The corresponding 1-decyl, 1-dodecyl, 1-tetradecyl, 1-hexadecyl, 1-octadecyl and 1-eicosyl and higher analogs are prepared using the corresponding monosaccharide and disaccharide uronic acids, prepared as described above. Alternatively, the 1-alkyl glucuronyl, or other uronic acylated analogs, may be prepared by initial purification of the deprotected or partially deprotected peptide followed by acylation by the desired uronic acid reagent. Alternatively, the 1-alkyl glucuronyl, or other uronic acylated analogs, may be prepared by initial purification of the recombinantly prepared peptide followed by selective acylation of the side chain amino function by the desired uronic acid reagent.

A. 1-Alkyl β-d-Glucuronic Acids. General Oxidation Method.

To a solution of 1-dodecyl β-d-glucopyranoside [2.0 g, 5.74 mmol] in 20 mL of acetonitrile and 20 mL of deionized water is added (diacetoxyiodo)benzene [4.4 g, 13.7 mmol] and TEMPO [0.18 g, 1.15 mmol]. The resulting mixture was stirred at room temperature until reaction completion (by 20 h). The reaction mixture was diluted with water and lyophilized to dryness to give crude product as a white powder of sufficient purity for direct use in coupling to the peptide Lys side chain (1.52 g, 73%). In a like manner were prepared the other 1-alkyl 3-d-glucuronic or melibiouronic acids used to acylate the other peptide products described herein. The corresponding 1-substituted glucosides or melibosides were prepared using the procedures in these examples but substituting the appropriate chain length dicarboxylic starting materials to yield the desired chain length from the synthetic procedures of the examples, for example hexadecanedioic acid, dodecanedioic acid and the like in place of octadecanedioic acid.

B. 18-(Tertbutoxy)-18-Oxooctadecanoic Acid

A suspension of octadecanedioic acid (40 g, 127 mmol) in toluene (500 ml) was heated at 95° C. under nitrogen. To the resulting solution, was added N,N-dimethylformamide di-tert-butylacetal (98 g, 434 mmol), dropwise over 3-4 hr. The reaction was stirred overnight at the same temperature, concentrated to dryness in vacuo and placed under high vacuum overnight. The resulting solid was suspended in CH$_2$Cl$_2$ (200 ml) with heat and sonication, and filtered at RT, washing with CH$_2$Cl$_2$. The filtrate (2) was concentrated to give the product as a solid (45 g, 86%) which was used without further purification.

C. Tert-Butyl 18-Hydroxyoctadecanoate

A solution of 18-(tertbutoxy)-18-oxooctadecanoic acid (45 g, 121 mmol) in THF was cooled over an ice bath, under nitrogen and treated dropwise with borane dimethylsulfide complex (16 ml, 158 mmol). Vigorous gas evolution occurred over the first few milliliters of addition. After the addition, the mixture was slowly allowed to warm to RT and was stirred overnight. The reaction was chilled over an ice bath, quenched with saturated sodium carbonate solution, diluted with ethyl acetate and washed with saturated sodium carbonate solution. The organic layer was concentrated in vacuo and placed under high vacuum overnight. The residue was dissolved in warm toluene (200 ml) and let stand for several hours at room temperature. The precipitated diol was removed by filtration through Celite, cake washed with toluene. The toluene solution was applied directly to a silica gel column and eluted with 10% ethyl acetate/hexane then 20% ethyl acetate/hexane, then 30% ethyl acetate/hexane and concentrated to give the product (24 g, 51%) as an oil which solidifies on standing. $^1$H NMR (500 MHz, $d_4$-MeOH): δ=3.64 (m, 2H), 2.21 (t, 2H, J=9), 1.44 (s, 9H) 1.50-1.62 (m, 4H), 1.20-1.40 (m, 27H)

D. Tert-Butyl 18-([1-Beta-D-Glucos-1-Yl]Oxy)Octadecanoate

Tert-butyl 18-hydroxyoctadecanoate (46 g, 129 mmol) was dissolved in toluene (400 ml), concentrated in vacuo to circa 250 ml, and allowed to come to room temperature under nitrogen. To this solution was added HgO (yellow) (22.3 g, 103 mmol), $HgBr_2$ (37 g, 103 mmol), and acetobrom glucose with vigorous stirring. Stirring was continued overnight until alcohol was consumed and the mixture was filtered through Celite. The filtrate was treated with copper (II)triflate (1 g) and stirred for 1 hour until the orthoester (spot above product on TLC) was degraded. The reaction was then washed with water and the organic layer was concentrated in vacuo. The residue was dissolved in methanol (500 ml) and treated with sodium methoxide (5.4 M in methanol) in 0.5 ml portions to bring the pH to 9 (spotting directly onto pH paper). The pH was checked every 0.5 hour and more sodium methoxide was added as necessary to maintain the pH at 9. The reaction was complete in 4 hr. Acetic acid was added dropwise to bring the pH to 7, and the mixture was concentrated in vacuo. The residue was loaded onto silica gel and purified by silica gel chromatography eluting with 5% methanol/$CH_2Cl_2$ then 10% methanol/$CH_2Cl_2$ to yield the product as a white solid (55 g, 82%). $^1$H NMR (400 MHz, $d_4$-MeOH): δ=4.30 (d, 1H, J=7.6), 3.84 (m, 1H), 3.77 (d, 1H, J=9.6), 3.45-3.60 (m, 2H), 3.36 (t, 1H, J=9.2), 3.21 (t, 1H, J=8.4), 2.20 (t, 2H, J=7.2), 1.50-1.67 (m, 4H), 1.43 (s, 9H), 1.43-1.33 (m, 2H), 1.28 (br s, 24H)

E. Tert-Butyl 18-([Beta-D-Glucuron-1-Yl]Oxy)Octadecanoate

Tert-butyl 18-([1-beta-D-glucos-1-yl]oxy)octadecanoate (50 g, 96 mmol) was dissolved in dioxane (800 ml) in a 2000 ml 3-neck flask with mechanical stirring and cooled to 10° C. To the solution was added 2,2,6,6-tetramethyl-1-piperidinyloxy (TEMPO) (150 mg, 0.96 mmol) and KBr (1.14 g, 9.6 mmol). Dropping funnels containing saturated $Na_2CO_3$ solution (300 ml) and 13% NaOCl solution (120 ml) were fixed to the flask. The carbonate solution was started on a rapid drip and the NaOCl was added at a slow drip (ca. 1 drop/second). After 100 ml of carbonate had been added, the pH was checked and more was added as necessary to maintain ca. pH 10. The temperature was maintained at 10° C. to 15° C. throughout. After 3 hr. starting material remained so more NaOCl (10 ml) was added rapidly. After 0.5 hr. the reaction was quenched with methanol (10 ml).

The mixture was poured into a 4000 ml Erlenmeyer flask, submerged in an ice bath and adjusted to pH 3 with 6N HCl. The mixture was diluted with ethyl acetate and washed with 1 N HCl and 2× with distilled water allowing the layers to separate on the final wash. The organic layer was concentrated in vacuo to give the product as a white foam (38 g, 74%).

Quantitative $^1$H NMR (500 MHz, $d_4$-MeOH) using 2,3,4,5-tetrachloronitrobenzene (TCNB) internal standard relative to anomeric CH gives 94.8% of expected weight. Purity by TLC>95% (20% MeOH/DCM/2 drops HOAc, stain using 20% $H_2SO_4$/EtOH+heat)$^1$H NMR (500 MHz, $d_4$-MeOH): δ=4.30 (d, 1H, J=9.5), 3.85 (m, 1H), 3.77 (d, 1H, J=7.5), 3.48-3.56 (m, 2H), 3.37 (t, 1H, J=11.5), 3.21 (t, 1H, J=9.5), 2.20 (t, 2H, J=9.5), 1.52-1.66 (m, 4H), 1.44 (s, 9H), 1.34-1.42 (br, 2H), 1.28 (s, 25H).

Example 2. Dual Agonist Peptides—In Vitro Assays

Cellular assays were carried out using standard cellular assays (DiscoveRx, LeadHunter assays) using readout of cAMP stimulation or arrestin activation. Compounds were weighed precisely in an amount of approximately 1 mg and shipped to DiscoverX (Fremont, CA) for dilution and assay. The assay used were for the glucagon (human, cloned into CHO cells) and GLP-1 (human, cloned into CHO cells) receptors in cellular assays. Assays were carried out in the presence of 0.1% ovalbumin. Historically such assays have been carried out in the presence of 0.1% BSA, but for these compounds which bind very tightly to serum albumin (>99%) it can distort the results and make the compounds seem much less potent. Use of 0.1% ovalbumin can avoid this problem. The improvement seen upon use of ovalbumin can be seen as an indicator of relative tightness of serum albumin binding for the peptide,

TABLE 5

| Compound | $EC_{50}$ cAMP GLP-1 R (pM) 0.1% Ovalb | $EC_{50}$ cAMP glucagon R (pM) 0.1% Ovalb | $EC_{50}$ cAMP GLP-1 R (pM) 0.1% BSA | $EC_{50}$ cAMP glucagon R (pM) 0.1% BSA |
|---|---|---|---|---|
| EU-A1588 | 124 | 250 | 23 | 43 |
| EU-A1871 | 39 | 66 | 162 | 461 |
| EU-A1872 | 43 | 86 | 1266 | 2624 |
| EU-A1873 | 39 | 44 | 1,116 | 1,680 |
| semaglutide | 14.9 | >0.01 | 181 | N/A |

EU-A1588=SEQ ID NO: 2; EU-A1871=SEQ ID NO: 3; EU-A1872=SEQ ID NO: 4; EU-A1873=SEQ ID NO: 1; semaglutide=SEQ ID NO: 11.

Assays were carried out in the presence of 0.1% ovalbumin. Historically such assays have been carried out in the presence of 0.1% BSA, but for these compounds which bind very tightly to serum albumin (>99%) it can distort the results and make the compounds seem much less potent. Use of 0.1% ovalbumin can avoid this problem. The improvement seen upon use of ovalbumin can be seen as an indicator of relative tightness of serum albumin binding for the peptide, see table below.

TABLE 6

Effect of replacement of BSA with ovalbumin in cellular assay for tight BSA binders

| Compound | Side chain | EC50 cAMP GLP-1 R (pM) 0.1% Ovalb | EC50 cAMP glucagon R (pM) 0.1% Ovalb | EC50 cAMP GLP-1 R (pM) 0.1% BSA | EC50 cAMP glucagon R (pM) 0.1% BSA | Ovalbumin vs. BSA-fold improv/*worsen* GLP-1 R | GCG R |
|---|---|---|---|---|---|---|---|
| EU-A1588 | melibiouronyl C16 | 124 | 250 | 23 | 43 | *5* | *6* |
| EU-A1871 | glucuronyl 15CO2H | 38.8 | 65.6 | 162 | 461 | 4 | 7 |
| EU-A1872 | glucuronyl 17CO2H | 42.5 | 86.4 | 1266 | 2624 | 30 | 30 |
| EU-A1873 | glucuronyl 17CO2H | 38.7 | 43.5 | 1,116 | 1,630 | 29 | 39 |
| semaglutide | (PEG)2-17CO2H | 14.9 | >0.01 | 181 | N/A | 12 | |

Here one can see that the very tight serum albumin binders (with $CO_2H$ containing substituents, mimicking a fatty acid head group) show a substantial fold improvement upon replacement of BSA by ovalbumin, which does not bind fatty acid mimics appreciably. The degree of fold improvement can give a reading on tightness of binding to the fatty acid binding sites on BSA. Thus, semaglutide improves 12-fold (tight binding) while EU-A1873 improves from 30 to 40×, implying substantially increased serum albumin binding. This degree of serum albumin binding can be expected to result in a suppressed Cmax and prolonged duration of action, as is seen in the bioassays for SEQ ID NO: 1.

The data presented in Tables 5 and 6 above demonstrate that the tested compounds are agonists of both GLP-1R and GCGR ("dual agonists"), unlike semaglutide which shows high affinity biased towards GLP-1. This data also shows that SEQ ID NO: 1 is a dual agonist peptide with about equal affinity for GLIA-1R and GCGR.

Example 3. Clinical Trial to Determine the Safety and Tolerability of Single and Repeated SC Doses of ALT-801 in Healthy Overweight and Obese Subjects, and to Characterize the Effective Dose Range Based on PK-PD Relationships This study is designed to assess the safety and tolerability of single and repeated SC doses of ALT-801 in healthy overweight and obese subjects (BMI 25.0-40.0 kg/m$^2$) and to characterize the effective dose range based on pharmacokinetic-pharmacodynamic (PK-PD) relationships. Overweight and obese healthy volunteers are studied as the PK in such subjects may be different from that in normal weight individuals. In addition, these subjects are able to better tolerate the predicted PD effect of weight loss and could even benefit from treatment. Appropriate contraceptive measures have been put in place to minimize the chances of pregnancy, and precautions have been taken to exclude pre-existing conditions that would make subjects at risk for treatment with GLP-1 or glucagon analogues. Diabetic subjects have been excluded until the effects of ALT-801 on glucose homeostasis are better characterized in a non-diabetic population. As overweight and obese subjects are expected to have varying levels of insulin resistance, the observations made in these studies, taken together with data from other compounds in this class, should be predictive of the effects observed when diabetic subjects are studied. Exclusions have been instituted that might otherwise affect an accurate assessment of the effects of ALT-801 on safety, PK, or PD. Analyses is conducted to evaluate the effects of the range of BMIs employed in this study on PK and PD parameters. The study will show the effects of ALT-801 on body weight, providing support for its use as a primary treatment for obesity.

The primary objective of the study is to assess the safety and tolerability of ALT-801 in healthy overweight and obese subjects after single and multiple ascending subcutaneous (SC) dose administration, by assessing adverse events (AEs), vital signs, clinical safety labs, urinalysis, physical examination, and injection site reactions; glucose homeostasis; blood pressure; electrocardiogram (ECK), Holter monitoring; and the like. The secondary objectives of the study are to evaluate: 1) the PK of ALT-801 after single and multiple ascending SC dose administration; and, 2) the PD effects of ALT-801 after single and multiple dose administration. Exploratory objectives of the study include evaluation of: 1) the expanded PD effects of ALT-801 after multiple dose administration; and, 2) the effects of ALT-801 on heart rate-corrected QT interval (QTc) prolongation. The study assessments, including liver fat content by MRI-PDFF, body weight, body composition by whole body MRI, insulin resistance, systemic inflammation, and GLP-1 and glucagon target engagement are based on the expected PD properties of ALT-801, which include weight loss and change in body composition. Measurements of glucose homeostasis are based on the potential effects of GLP-1 and glucagon analogues on glucose control. Ambulatory blood pressure monitoring (ABPM) and Holter monitoring have been included since GLP-1 and glucagon agonists have been associated with clinically insignificant changes in blood pressure and heart rate. Holter monitoring has also been included to provide information on any potential effects of ALT-801 on QT interval prolongation. Based on the pharmacology and safety experience with GLP-1 and GLP-1/glucagon dual agonists, a dose-related incidence of GI AEs, including nausea and vomiting, may occur. Glucose homeostasis will also be evaluated, including the incidence and severity of hyperglycemia and hypoglycemia. As weight loss is a desired property of this compound, it is monitored for efficacy rather than safety. However, if weight loss is deemed to be excessive, the dose in subsequent cohorts may be adjusted. Study medication may be paused or discontinued in individual subjects if the level of weight loss is considered unsafe or excessive. Subjects will also be monitored for drug-induced liver injury. A blood sample is collected predose and after the final dose of study drug for biobanking in subjects that provide separate consent. These samples are used to discover and/or validate biomarkers in NASH and related diseases, including potential genetic analyses.

This study described herein is a first-in-huma (FIH), Phase 1, randomized, double-blind, placebo-controlled, 2-part study of single ascending doses (SAD) and multiple ascending doses (MAD) of ALT-801 in healthy overweight and obese subjects. Overweight to obese subjects (body mass index [BMI] 25.0-40.0 kg/m2) will be enrolled. In Part 1, the single ascending dose (SAD) Phase, subjects undergo a screening period of up to 28 days. Overweight to obese subjects who meet inclusion and do not meet exclusion criteria will be randomized in a 3:1 ratio in cohorts of 8 subjects, with 6 subjects to receive ALT-801 and 2 subjects to receive placebo. Study medication (SEQ ID NO: 1 formulated as ALT-801 for SC administration) is administered subcutaneously (SC) at abdominal sites in all SAD cohorts. Subjects are admitted to the research unit approximately 1 day prior to study medication administration (Day −1) and will be discharged on Day 8. Subjects will receive 1 SC dose of ALT-801 or placebo on Day 1. Six cohorts are planned, with 2 additional optional cohorts, for Part 1. The following dose levels are planned: 0.4, 1.2, 2.4, 4.8, 7.2, and 9.4 mg as a weekly dose administered once a week (QW) based on a 60 kg human. These doses may be modified on the basis of clinical observations, or, when available, PK data. The first 2 subjects (1 ALT-801 and 1 placebo) in each SAD cohort are dosed in sentinel manner at least 48 hours before the remaining subjects. Subjects undergo overnight fasting for at least 10 hours prior to assessments on Days −1 through 5 and prior to assessments on Day 8, and meals will be standardized. Subjects undergo study assessments to evaluate safety, including ECGs, CGM, and ABPM, and will have blood samples collected for PK as described in the schedule of assessments as described below. Following discharge from the research unit, subjects will return for outpatient visits for PK and safety assessments every 3 days through Day 26 and for a follow-up visit on Day 35 or at least 5 half-lives, as determined over the course of dosing. If predicted efficacious doses and exposures based on pharmacometric modeling are not achieved and/or if the maximum tolerated dose (MTD) for a single dose is not identified after completing the 6 planned cohorts, up to 2 additional single-dose cohorts are enrolled in Part 1. Part 2, the multiple ascending dose (MAD) phase commences once Day 8 of SAD Cohort 3 is completed and the safety of that cohort is assessed. The starting dose in Part 2 is generally one-half the dose for SAD Cohort 3.

After providing informed consent, overweight to obese subjects undergo a screening period of up to 28 days. Subjects are instructed to maintain their normal diet and activities during screening and not to start any new diets, supplements, or exercise programs at any time while participating in the study. Subjects are admitted to the research unit approximately 4 days prior to study medication administration (Day −4) for a diet and exercise run-in acclimation period during which they will receive standardized meals. A standardized diet is provided with daily calories individualized using a predictive BMR×1.5 to account for inter-subject differences based on body weight, height, age, and sex. The activity level of study participants is also standardized. Subjects who meet inclusion and do not meet exclusion criteria are randomized on Day −1 in a 5:1 ratio in cohorts of 12 subjects, with 10 subjects to receive ALT-801 QW and 2 subjects to receive placebo QW for 6 weeks. Study medication is administered subcutaneously (SC) at abdominal sites in all MAD cohorts.

Subjects receive the first dose of study medication on Day 1 and remain in the research unit until after they receive the second dose on Day 8. Subjects then return for 3 outpatient dosing visits at weekly intervals (Days 15, 22, and 29) and are re-admitted from Day 32 to Day 43. Subjects will receive the last dose of study medication on Day 36. Following discharge on Day 43, subjects return for a follow-up visit on Day 70 or 5 half-lives after dosing, whichever is sooner. Subjects undergo several study assessments to evaluate the safety, PD, and PK of ALT-801 as described herein. Safety evaluations will include ECGs, CGM, and ABPM. PD assessments include anthropomorphic measures, dietary assessments, imaging, and blood collection for biomarkers. The Patient Assessment of Gastrointestinal Disorders Symptom Severity Index (PAGI-SYM) is administered to assess the effects of treatment on GI symptoms. Blood samples are collected for PK and immunogenicity. Subjects undergo overnight fasting for at least 10 hours prior to Day −1 through Day 5 and prior to Days 7, 8, 36, 37, 42, and 43. In addition, subjects will receive a standard breakfast meal for the mixed meal tolerance tests on Days −1, 7, and 42.

The doses for the MAD will be selected on the basis of clinical data and, when available, PK data from previously completed SAD and MAD cohorts. Three MAD cohorts are planned with up to 2 optional additional cohorts, if needed, to achieve predicted efficacious doses and exposures based on pharmacometric modeling, to expand a previously studied dose level, to continue dose escalation if an MTD for this phase is not identified, or explore dose titration schemes if GI intolerance is observed before the maximally effective dose based on pharmacometric modeling is reached.

The maximal recommended starting dose (MRSD) in Part 1 is based on one tenth the human equivalent dose (HED) at the NOAEL determined in animals (rats and monkeys) in the pivotal Good Laboratory Practice toxicology study. Both rats and monkeys were deemed to have a similar clinical response to ALT-801, but the exposures at the NOAEL were slightly lower in rats, resulting in a more conservative human starting dose. The rat NOAEL was the high dose, 0.45 mg/kg/week, which is equivalent to 0.44 mg/wk in a 60 kg human based on body surface area scaling. Notably, the NOAEL in monkeys was also the high dose, 0.25 mg/kg, which is equivalent to 0.49 mg/wk in a 60 kg human based on body surface area scaling. Using a 10-fold scaling factor for safety, the human starting dose of 0.40 mg/wk for a 60 kg human was selected. Furthermore, extrapolated human exposures at the maximum recommended starting dose (MRSD) are well below the exposures at the monkey NOAEL, which notably, are comparable to exposures at the rat NOAEL. This is particularly relevant because the monkey, although not the most sensitive species, is biologically the more relevant species for the most clinically relevant toxicities (i.e., reduced food intake and vomiting). Clinical observations and PK in Part 1 will ultimately guide dosing considerations in Part 2.

The primary findings of ALT-801 in studies in rats and monkeys was weight loss (see, e.g., Example 4). Modifying the schedule in rats, which were dosed daily, to 3 days a week, improved tolerability by reducing the impact of ALT-801 on food consumption and body weight loss, consistent with the mechanism of action. The toxicity of GLP-1 and glucagon agonists have also been well characterized in human studies. The pre-clinical safety findings support a 3-fold dose escalation increment to SAD Cohort 2. Subsequent escalations will not exceed 2-fold in either part of the study. Dose titration schemes may be explored if needed to improve tolerability. Adding to the confidence around these predictions, the dose-exposure relationship in humans is predicted to be linear based on a population PK model of several preclinical species (mice, rats, mini-pigs, and monkeys). The model is updated with human data as the study is ongoing. The predicted $t_{1/2}$ of ALT-801 in humans is in the range of 100 hours, an assumption that will also be confirmed in Part 1. Based on once-weekly (QW) dosing, the estimated accumulation with repeated dosing at steady state is not greater than 2-fold. To ensure that multiple dose exposures will remain within single dose exposures, the starting dose in Part 2 is planned to be one-half the dose for Part 1 Cohort 3. However, subsequent Part 2 cohorts may be adjusted based on safety and PK data. The decision to escalate to each successive dose level is based on assessment of safety and tolerability through Day 8 (7 days following the single dose) in Part 1 and Day 15 (7 days following the second dose) in Part 2. The decision to dose-escalate after the second week is completed is based on the observation from earlier GLP-1 and GLP-1/glucagon dual agonist studies that AEs, which are expected to be predominately nausea or vomiting, will occur in the first 2 weeks of dosing. Further, the expectation is the $C_{max}$ and $AUC_{tau}$ of the final week of dosing will not exceed the Cmax or $AUC_{inf}$ of a dose in a previously completed and safety-assessed SAD cohort. The target dose for maximal efficacy, corresponding to ED80 to ED90, in an adult human is estimated to be between 1 and 5 mg, and the target plasma concentrations between 50 and 100 ng/ml, based on exposures in animals at efficacious doses and pharmacometric modelling of animal PK parameters to predict human PK. Thus, the estimated starting dose is approximately 2.5-fold lower than the lowest predicted efficacious dose and is expected to be inactive.

To maximize safety, single ascending dose (SAD) and multiple ascending dose (MAD) escalation is planned to not exceed exposures at the NOAEL in rats. However, if PD and tolerability suggest that overweight and obese subjects would benefit from doses that are expected to exceed exposures at the rat NOAEL, supportive safety and efficacy data is presented to the IEC and agreement is obtained prior to continuing SAD and MAD escalation.

A minimum of 6 subjects is required to dose escalate in Part 1, and 8 subjects in Part 2, with at least 1 subject in each cohort receiving placebo. The suggested next dose levels may be adjusted downward based on evaluation of safety and tolerability data observed in previous treatment cohorts if observations suggest that dose escalation is exceeding MTD. Dosing may proceed until the MTD is identified, which is determined separately for each part of the study. Available PK data may be used to guide decision making and is explicitly considered if exposures are expected to exceed the NOAEL in rats. To maximize safety, the planned SAD and MAD escalation will not exceed exposures at the NOAEL in rats.

Following completion of the screening activities, subjects who meet the all the inclusion and none of the exclusion criteria are randomized by an interactive web response system (IWRS). In Part 1, 2 subjects in each cohort are randomly assigned 1:1 to ALT-801 or placebo treatment groups for sentinel dosing. The remaining 6 subjects in each cohort of 8 subjects are randomly assigned to ALT-801 or placebo treatment groups, with 5 assigned to the ALT-801 group and 1 assigned to the placebo group for an overall 3:1 ratio of ALT-801 and placebo in each cohort. In Part 2, cohorts of 12 subjects are randomly assigned in a 5:1 ratio to ALT-801 or placebo treatment groups, with 10 assigned to the ALT-801 group and 2 assigned to the placebo group.

SEQ ID NO: 1 is formulated as ALT-801, in glass vials in a sterile, buffered aqueous solution (e.g., about 0.050% (w/w) polysorbate 20, about 0.348% (w/w) arginine, about 4.260% (w/w) mannitol in deionized water (pH 7.7±0.1)) and comprising SEQ ID NO: 1 at a final concentration of 2.5 mg/mL and total fill volume of 1.2 mL, and administered as a subcutaneous (SC) injection. In Part 1, a single dose of study medication is administered on Day 1. The first 2 subjects (1 ALT-801 and 1 placebo) in each SAD cohort are dosed in sentinel manner at least 48 hours before the remaining subjects. In Part 2, study medication is administered QW for 6 weeks. Doses are administered on Days 1, 8, 15, 22, 29, and 36. The starting dose in Part 1 is 0.40 mg, which corresponds to one-tenth the human equivalent dose at the no observed adverse effect level (NOAEL) in rats (rounded down from 0.44 mg/wk for safety), and the dose escalation will follow a modified Fibonacci scheme and is 3-fold or less with planned dose levels of 0.40, 1.2, 2.4, 4.8, 7.2, and 9.4 mg (equivalent to a weekly dose administered once every 7 days). The starting dose in Part 2 is planned to be one-half the dose for Part 1 Cohort 3. However, subsequent Part 2 cohorts may be adjusted based on safety and PK data. The decision to escalate to each successive dose level is based on assessment of safety and tolerability through Day 8 in Part 1 (7 days following the single dose) and Day 15 (7 days following the second dose) in Part 2. Dose escalation may be modified, and dose titration schemes as appropriate, or as described herein. Each dose of ALT-801 or placebo is administered as a SC injection in the abdominal region by appropriately trained clinical staff members. The volume of administration is based on the selected dose and a concentration of 2.5 mg/mL for the final drug product. The saline placebo is matched for volume based on the dose and volume of ALT-801 administered in that cohort. As weight loss is a desired property of this compound, it is monitored for efficacy rather than safety. However, if weight loss is deemed to be excessive, the dose in subsequent cohorts may be adjusted. Study medication may be paused or discontinued in individual subjects if the level of weight loss is considered excessive. Study medication may be paused or discontinued in individual subjects if the level of GI adverse events is considered excessive and intolerable despite antiemetic treatment (eg, severe GI AEs continue >24 hours). If there is persistent vomiting a subject may be given an antiemetic. A 5HT3 receptor antagonist (e.g., ondansetron) is preferable in this situation. The suggested dose levels may be adjusted downward based on evaluation of safety and tolerability data observed in previous treatment cohorts if observations suggest that dose escalation is exceeding the MTD. Dosing may proceed until the MTD is identified, which is determined separately for each part of the study. Available PK data may be used to guide decision making.

Blood samples are collected for PK assessment at hour zero, 1, 4, 6, 8, 12, and 16 on days −1, 1, 2, 3, 4, 5, 8, 11, 14, 17, 20, 23 and 26 for Part 1 and hour zero, 1, 4, 6, 8, 12, and 16 on days −1, 1, 2, 3, 4, 5, 8, 15, 22, 29 and 36-38 for Part 2. Remaining plasma from PK samples may be stored frozen with no time limitation and may be used for ALT-801 bioanalytical method development or to explore ALT-801 metabolites. ECG readings are time-matched to the PK sample times. When multiple activities occur at the same timepoint, ECGs should be collected first, and PK blood draws should occur at the nominal time. PD assessments are done in Part 2 only.

Height is measured in centimeters using a wall-mounted stadiometer or one mounted on a balance beam scale, whichever is available. Subjects should be wearing socks or be barefoot. With the exception of screening visits, weight is measured in kilograms using a calibrated scale at approximately the same time of day at each nominal timepoint. Measurements should be taken with subjects wearing a gown (or other standard clothing provided by the clinical research unit), undergarments, and socks (no shoes), while fasting and after the subject has been asked to void (ie, empty bladder). Waist circumference should be taken with the subject wearing a gown. The measurement is performed at a level midway between the superior aspect of the iliac crests and the lower lateral margin of the ribs. The measurement need not be at the level of the umbilicus. The measuring tape is kept horizontal. Height, weight, and waist circumference is measured, and BMI calculated and recorded according to the schedules in Part 1 and Part 2. Measurement of height is required at screening only. Waist circumference is measured for subjects in Part 2 only.

FibroScan® is an ultrasound-like instrument able to simultaneously measure liver stiffness and steatosis through Vibration-Controlled Transient Elastography (VCTE) and CAP, respectively. For subjects in Part 2, FibroScan® CAP is measured during screening following an overnight fast of at least 10 hours. FibroScan® CAP is measured before MRI-PDFF. MRI-PDFF is a quantitative imaging biomarker that enables accurate, repeatable and reproducible quantitative assessment of liver fat over the entire liver. For subjects in Part 2, MRI-PDFF is measured during screening (only occurs if CAP is ≥300 dB/m) and at the EOS visit following a minimum 10 hour fast. The percent liver fat is corrected for total liver volume, which is measured simultaneously with liver fat content. Whole body MRI is an established imaging technique that is used to measure body composition, including lean body mass. For subjects in Part 2, whole body MRI is performed during screening and the EOS visit in conjunction with MRI-PDFF.

In Parts 1 and 2, subjects are provided a standardized diet during the inpatient periods at the research unit. Daily calories are individualized using a predictive BMR equation multiplied by an activity factor of 1.5 and macronutrient composition is standardized at 40-50% carbohydrate, 15-25% protein, and 30-40% fat. In Part 2, the same standardized meals are provided on Day −4 to Day −2 and Day 39 to Day 41, prior to PD assessments on Day −1 and Day 42. The timing and type of meals will also be specific for ECG, MRI-PDFF, and MMTT assessments, as described in each of the corresponding manuals.

Food intake and appetite are assessed using an ad libitum meal test and the VAS questionnaire. VAS questionnaires are standard techniques in appetite research that record feelings of hunger, satiety, fullness, and desire to eat specific tastes, such as sweet, salty, savory, and fatty [Flint 2000]. Subjects will complete a VAS questionnaire before and after an ad libitum meal on days specified in the schedule of assessments. The size of the ad libitum meal will exceed expected intake of healthy overweight and obese volunteers. During the test meal, subjects are isolated and environmental cues minimized (ie, no TV, cell phones, computers, etc.). Subjects are instructed that they have 30 minutes to consume as much or as little as they want, and they should eat until comfortably full. Pre and post meal weights are recorded to capture food intake, and caloric consumption is determined.

The basal metabolic rate (BMR) and resting energy exposure (REE) are assessed in the morning under fasting conditions and following a fasting period of at least 10 hours. Resting energy expenditure to be conducted on Days −1 and 42. BMR and REE are determined using the ventilated hood method (indirect calorimetry). Because BMR usually is the main component of daily energy expenditure, changes to BMR might be of clinical relevance within the context of a metabolic drug development program that targets energy expenditure.

Following a minimum 10 hour fast the subject will undergo a mixed meal tolerance test (MMTT) which will involve the consumption of a standardized liquid meal (6 fluid ounces of Ensure Plus [700 kcal], a nutritional supplement containing the components of fat, carbohydrate, and protein, which make up a standard MMTT) within 5 minutes. The t=0 minute sample (i.e. prior to the standardized liquid meal) are the last HOMA IR 2 blood sample (see above). Hormone markers will include glucose, insulin and C-peptide. Samples are collected at intervals of 5 minutes for the first 15 minutes and 30 minutes thereafter through 240 minutes after consumption of the standardized liquid meal (with no additional food intake during this time). The MMTT procedures are performed on days specified in the schedule of assessments. In order to standardize the test and reduce variability, each test is preceded by a 3-day standardized diet and standardized physical activity run-in period after admission to the clinical research unit.

Blood samples are collected for evaluation of ketone bodies after the subject has fasted overnight for at least 10 hours, 1 day prior to the first and second doses, and 6 days after the last dose. Blood samples for evaluation of FGF-21 and adiponectin are collected after the subject has fasted overnight for at least 10. Following a minimum 10 hour fast, blood is collected for assessment of lipids, including cholesterol (total, HDL, LDL), Apo A and B, lipoprotein(a), TG, and tripalmitin, prior to the first dose and 6 days after the last dose of study medication, as indicated in Table 4. Blood is collected for the assessment of inflammatory markers, including TNF-α, hs-CRP, leptin, MCP-1, and IL-6 prior to the first dose and 6 days after the last dose of study medication, as indicated in Table 4. Glucose homeostasis is assessed by 24-hour CGM using a Dexcom G6 CGM during the periods indicated in Part 1 and Part 2.

The Safety Population includes all randomized subjects who receive at least 1 dose of study medication. Subjects is analyzed according to the treatment that they receive. The PK Population includes all randomized subjects who receive at least 1 dose of ALT-801 and who have sufficient PK data for analysis. The QT Population includes all subjects in the PK Population who have at least 1 time-matched ECG at baseline and corresponding time-matched PK-ECG post-dose. The PD Population includes all randomized subjects who receive at least 1 dose of study medication and who have results from baseline and at least 1 post-baseline PD assessment.

In the statistical methods used, descriptive statistics are used to evaluate differences in demographic and baseline characteristics. Medical history is coded using the most current Medical Dictionary for Regulatory Activities (MedDRA) version and is listed by subject. Continuous safety data is summarized with descriptive statistics (arithmetic mean, standard deviation [SD], median, minimum, and maximum) by dose level and treatment (active or placebo). Categorical safety data is summarized with frequency counts and percentages by study part, dose level, treatment, and day where applicable.

AEs are coded using the most current MedDRA version. A by-subject AE data listing, including verbatim term, preferred term, SOC, treatment, severity, and relationship to study medication, are provided. The number of subjects experiencing treatment-emergent AEs (TEAEs) and number of individual TEAEs and injection site reactions are summarized by treatment group, SOC, and preferred term. TEAEs will also be summarized by severity (Grade 1 through 4) and by relationship to study medication (unlikely, possibly, probably). Relatedness for Stopping Rules are defined as possibly or probably related. Laboratory evaluations, vital signs assessments, continuous cardiac monitoring, ECG parameters (excluding Holter monitoring), CGM measurements, ABPM measurements, and meal tolerance test parameters are summarized by study part, treatment group, dose level, and protocol specified collection time point. A summary of change from baseline at each protocol specified time point by treatment group will also be presented. Changes in physical examinations are listed for each subject. The analysis of the PAGI-SYM is detailed in the statistical analysis plan (SAP). Concomitant medications are listed by subject and coded using the most current WHO drug dictionary.

Pharmacokinetics includes individual ALT-801 concentration data listed and summarized by cohort with descriptive statistics (sample size [N], arithmetic mean, SD, coefficient of variation [CV %], median, minimum, and maximum). Individual and mean±SD ALT-801 concentration-time profiles for each cohort will also be presented graphically. Plasma ALT-801 noncompartmental (NCA) PK parameters Cmax, time to maximum plasma concentration (Tmax), AUC0-t, AUC0-inf, elimination rate constant (Kel), t½, apparent total body clearance (CL/F), and apparent volume of distribution during terminal phase (Vz/F) (where data are sufficient for parameter determination) is estimated for the SAD part. For the MAD part, Tmax, Cmax, and AUCtau PK parameters are estimated following the first and the last dose (Week 1 and Week 6). If data permit, Kel, t½, apparent total body clearance at steady state (CLSS/F) and apparent volume of distribution at steady state (VSS/F) are estimated following Week 6 dosing. Pharmacokinetic parameters are listed for each individual and summarized by cohort using descriptive statistics (N, arithmetic mean, SD, CV %, median, minimum, maximum, geometric mean, and geometric CV %). The effects of baseline BMI on PK parameters are evaluated by correlation analyses. Dose proportionality is assessed using the power model approach, as appropriate. Accumulation is assessed as the ratio of Cmax and AUC0-tau at Week 6 to Week 1. Steady state is assessed by comparison of trough concentrations from the first to the last dose.

ECGs extracted from Holter monitors are analyzed by a central ECG laboratory with a selected group of skilled readers blinded to subject, visit, treatment, and nominal timepoint. A single reader will review an individual subject's ECGs, unless a second review based on quality control or availability is needed. All ECGs are analyzed using the same lead for an individual subject. The primary analysis lead is Lead II, unless not analyzable, then V2 or V5 is used for an individual subject's entire data set.

The primary analysis is the mean change and one-sided upper 95% confidence limit for the placebo-corrected, change from baseline postdose timepoint using the Fridericia corrected QT interval ($\Delta\Delta$QTcF). Other correction methods such as Bazett's (QTcB), individual corrected (QTcI), or population corrected (QTcP) may be explored and compared. At minimum, Fridericia's and Bazett's corrections are analyzed and presented. Secondary analyses will include the relationship between time-matched plasma concentrations and $\Delta\Delta$QTcF using linear mixed effects modelling. The immunogenicity of repeated dose administration of ALT-801 is assessed by evaluation of serum samples using an ELISA based assay collected at the final visit of the MAD phase. If end of study samples are positive, mid-study samples will also be analyzed. Immunogenicity may be correlated to safety and PK, if applicable.

Pharmacodynamics studies include changes in liver fat content, anthropomorphic parameters, GLP-1 engagement and insulin resistance, glucagon engagement, and lipid and inflammation markers are listed and summarized by treatment group with descriptive statistics (sample size [N], arithmetic mean, SD, median, minimum, maximum, geometric mean, and geometric CV %). Inferential statistics are applied, as applicable. The effects of baseline BMI on PD parameters are evaluated by co-variate analyses.

An interim analysis may be conducted following the completion of 2 or more doses in MAD Cohort 3. The objective of this analysis is to permit dose-selection for follow-on trials. For this analysis, the study will remain blinded and subject level safety, PD, and available PK data is de-identified for analysis. Summary data by study part, dose level, treatment group (active or placebo), and by day where applicable is reported. The conduct of the interim analysis is detailed in the SAP.

Example 4. ALT-801 Phase 1 Study in Overweight and Obese Volunteers (6-Week Interim Data)

This example presents the results of an ALT-801 Phase 1 clinical trial that is a placebo-controlled, first-in-human, single ascending dose (SAD) and multiple ascending dose (MAD) study in overweight and obese volunteers being conducted in Australia under a clinical trial application. The primary objectives of the study are to assess the safety and tolerability, pharmacokinetics, and weight loss in ALT-801 recipients compared to placebo over 12 weeks of weekly dosing. Dosing in the MAD phase commenced with a cohort receiving ALT-801 1.2 mg SC or placebo once weekly and is progressing through higher dose cohorts, with subjects in the 1.2 mg and 1.8 mg cohorts currently have completed six weeks of treatment. Interim analyses at six weeks of dosing have been performed for the first two study cohorts and is presented in this example.

This study shows that ALT-801 induces rapid and robust weight loss in healthy overweight and obese volunteers. Results of weight loss from a prespecified 6-week interim analysis of the ongoing 12-week, Phase 1, placebo-controlled, single and multiple ascending dose study of ALT-801, in healthy overweight and obese volunteers are presented in Table 7. Using a once weekly ALT-801 dose of 1.8 mg subcutaneously (SC), the analysis showed that a mean weight loss of 5.4% was achieved by Week 6 (Day 43) compared to a weight gain of 0.9% in the placebo group (net change from placebo of 6.3%), surpassing the pre-study treatment target of 2% weight loss (Table 7, FIG. 1). All but one of the 9 subjects who received the subcutaneous (sc) 1.8 mg SC dose achieved at least 3% weight loss by Week 6. A lower dose cohort that received a weekly 1.2 mg SC dose achieved a weight loss of 1.8% (net change from placebo of 2.7%) at the same time point.

TABLE 7

Weight - Observed Results and Change from Baseline by Timepoint - Multiple Ascending Dose (MAD)

| Parameter | Visit | Statistics | NASH MAD Cohorts | | |
| --- | --- | --- | --- | --- | --- |
| | | | M1 1.2 mg ALT-801 (N = 7) | M2 1.8 mg ALT-801 (N = 9) | PLACEBO (N = 4) |
| Observed Results | Baseline | n | 7 | 9 | 4 |
| | | Mean (SD) | 90.54 (15.4) | 86.41 (12.9) | 86.8 (6) |
| | | Median | 95.5 | 90.1 | 85.25 |
| | | Min, Max | 63.8, 106.2 | 62.8, 104.4 | 81.3, 95.4 |
| Observed Results | Day 8 | n | 7 | 9 | 4 |
| | | Mean (SD) | 89.34 (15.3) | 84.57 (12.3) | 86.62 (7.3) |
| | | Median | 94.9 | 88.9 | 84.8 |
| | | Min, Max | 62.7, 105.9 | 62.4, 102.6 | 79.9, 97 |
| Changed from Baseline (kg) | Day 8 | n | 7 | 9 | 4 |
| | | Mean (SD) | −1.2 (1) | −1.84 (1.4) | −0.18 (1.3) |
| | | Median | −1.1 | −1.2 | −0.45 |
| | | Min, Max | −2.9, −0.2 | −4.2, −0.4 | −1.4, 1.6 |
| % Changed from Baseline | Day 8 | n | 7 | 9 | 4 |
| | | Mean (SD) | −1.35 (1) | −2.06 (1.5) | −0.27 (1.4) |
| | | Median | −1.61 | −1.7 | −0.53 |
| | | Min, Max | −2.95, −0.24 | −4.49, −0.6 | −1.72, 1.68 |
| Observed Results | Day 15 | n | 6 | 9 | 4 |
| | | Mean (SD) | 94.3 (10.6) | 84.31 (13) | 87.28 (6.3) |
| | | Median | 95.3 | 87.8 | 85.7 |
| | | Min, Max | 79.3, 105.9 | 60, 102.3 | 81.5, 96.2 |
| Changed from Baseline (kg) | Day 15 | n | 6 | 9 | 4 |
| | | Mean (SD) | −0.7 (1.1) | −2.1 (0.9) | 0.48 (0.4) |
| | | Median | −0.6 | −2.2 | 0.5 |
| | | Min, Max | −2.6, 0.7 | −3.4, −0.7 | 0, 0.9 |
| % Changed from Baseline | Day 15 | n | 6 | 9 | 4 |
| | | Mean (SD) | −0.72 (1.1) | −2.51 (1.2) | 0.53 (0.5) |
| | | Median | −0.6 | −2.57 | 0.54 |
| | | Min, Max | −2.64, 0.83 | −4.46, −0.74 | 0, 1.05 |
| Observed Results | Day 22 | n | 6 | 9 | 4 |
| | | Mean (SD) | 94.63 (9.7) | 83.66 (13.3) | 87.85 (5.1) |
| | | Median | 94.7 | 87 | 86.6 |
| | | Min, Max | 79.4, 105.1 | 59.7, 102.7 | 83.2, 95 |
| Changed from Baseline (kg) | Day 22 | n | 6 | 9 | 4 |
| | | Mean (SD) | −0.37 (2.8) | −2.76 (1) | 1.05 (1) |
| | | Median | −1.05 | −3.1 | 1.35 |
| | | Min, Max | −2.9, 5.1 | −3.8, −1.3 | −0.4, 1.9 |
| % Changed from Baseline | Day 22 | n | 6 | 9 | 4 |
| | | Mean (SD) | −0.24 (3.2) | −3.32 (1.4) | 1.27 (1.2) |
| | | Median | −0.99 | −3.56 | 1.58 |
| | | Min, Max | −2.95, 6.05 | −5.25, −1.37 | −0.42, 2.34 |
| Observed Results | Day 29 | n | 6 | 9 | 4 |
| | | Mean (SD) | 93.82 (10.4) | 82.92 (12.8) | 87.82 (5.7) |
| | | Median | 94.15 | 87.3 | 86.55 |
| | | Min, Max | 79.5, 105.3 | 59.1, 100 | 82.6, 95.6 |
| Changed from Baseline (kg) | Day 29 | n | 6 | 9 | 4 |
| | | Mean (SD) | −1.18 (1.5) | −3.49 (1.2) | 1.02 (1.1) |
| | | Median | −0.9 | −3.7 | 0.75 |
| | | Min, Max | −3.9, 0.5 | −5, −1.7 | 0.1, 2.5 |
| % Changed from Baseline | Day 29 | n | 6 | 9 | 4 |
| | | Mean (SD) | −1.2 (1.6) | −4.12 (1.5) | 1.21 (1.3) |
| | | Median | −0.94 | −4.21 | 0.9 |
| | | Min, Max | −3.96, 0.59 | −5.89, −1.79 | 0.12, 2.92 |
| Observed Results | Day 36 | n | 7 | 9 | 4 |
| | | Mean (SD) | 89.23 (15) | 82.7 (13.5) | 87.83 (6) |
| | | Median | 93.2 | 86.3 | 85.85 |
| | | Min, Max | 62.3, 105.5 | 57.6, 102 | 83.1, 96.5 |
| Changed from Baseline (kg) | Day 36 | n | 7 | 9 | 4 |
| | | Mean (SD) | −1.31 (1.7) | −3.71 (1.4) | 1.02 (0.8) |
| | | Median | −1.5 | −3.3 | 1.2 |
| | | Min, Max | −3.7, 1.3 | −6.1, −1.9 | −0.1, 1.8 |
| % Changed from Baseline | Day 36 | n | 7 | 9 | 4 |
| | | Mean (SD) | −1.41 (1.8) | −4.51 (2.2) | 1.19 (1) |
| | | Median | −2.35 | −3.74 | 1.34 |
| | | Min, Max | −3.76, 1.54 | −8.28, −2.29 | −0.12, 2.21 |
| Observed Results | Day 43 | n | 6 | 9 | 4 |
| | | Mean (SD) | 93.2 (10.1) | 81.94 (13.5) | 87.58 (6) |
| | | Median | 93.7 | 85.9 | 85.5 |
| | | Min, Max | 78.7, 104.4 | 57.5, 100.4 | 83, 96.3 |
| Changed from Baseline (kg) | Day 43 | n | 6 | 9 | 4 |
| | | Mean (SD) | −1.8 (1.9) | −4.47 (2) | 0.77 (0.9) |
| | | Median | −1.45 | −4.9 | 0.9 |
| | | Min, Max | −5, 0.8 | −7.7, −0.5 | −0.4, 1.7 |

TABLE 7-continued

Weight - Observed Results and Change from Baseline by Timepoint - Multiple Ascending Dose (MAD)

| | | | NASH MAD Cohorts | | |
|---|---|---|---|---|---|
| Parameter | Visit | Statistics | M1 1.2 mg ALT-801 (N = 7) | M2 1.8 mg ALT-801 (N = 9) | PLACEBO (N = 4) |
| % Changed from Baseline | Day 43 | n | 6 | 9 | 4 |
| | | Mean (SD) | −1.82 (2) | −5.38 (2.6) | 0.9 (1.1) |
| | | Median | −1.66 | −5.28 | 1 |
| | | Min, Max | −5.08, 0.95 | −8.44, −0.53 | −0.47, 2.09 |

The study presented in this example also shows that ALT-801 is well-tolerated without dose titration. Results of adverse events from a prespecified six-week interim analysis of an ongoing 12-week, Phase 1, placebo-controlled, single and multiple ascending dose study of ALT-801, in healthy overweight and obese volunteers are presented in Table 8. The data shows that ALT-801 was well-tolerated without dose titration, with transient nausea rates of 14.3% at the 1.2 mg dose and 22.2% at the 1.8 mg dose, respectively, and there were no reports of vomiting, diarrhea or constipation at either dose. All nausea events at the 1.8 mg dose were mild in severity. These results place ALT-801 amongst the most effective and well-tolerated of GLP-1 based therapeutics. Gastrointestinal events have required other GLP-1 based agents to dose titrate over 16 to 20 weeks to maintain adequate tolerability.

TABLE 8

Summary of Subjects by Adverse Event Term and Severity - Multiple ascending dose (MAD)

| | NASH MAD Cohorts | | |
|---|---|---|---|
| ADVERSE EVENT SEVERITY | M1 1.2 mg ALT-801 (N = 7) | M2 1.8 mg ALT-801 (N = 9) | PLACEBO (N = 4) |
| ABNORMAL LIVER FUNCTION TESTS | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| ANEMIA | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| ANOREXIA | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| BLOATED ABDOMEN | 0 (0.0%) | 0 (0.0%) | 1 (25.0%) |
| MILD | 0 (0.0%) | 0 (0.0%) | 1 (25.0%) |
| MODERATE | 0 (0.0%) | 0 (0.0%) | 0 (0.0%) |
| SEVERE | 0 (0.0%) | 0 (0.0%) | 0 (0.0%) |
| DECREASE APPETITE/ ORAL INTAKE | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| DERANGED LIVER FUNCTION THS | 0 (0.0%) | 0 (0.0%) | 1 (25.0%) |
| MILD | 0 (0.0%) | 0 (0.0%) | 0 (0.0%) |
| MODERATE | 0 (0.0%) | 0 (0.0%) | 1 (25.0%) |
| SEVERE | 0 (0.0%) | 0 (0.0%) | 0 (0.0%) |
| DIZZINESS (POSTURED) SINGLE EPISODE | 1 (14.3%) | 0 (0.0%) | 0 (0.0%) |
| MILD | 1 (14.3%) | 0 (0.0%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| FATIGUE | 1 (14.3%) | 1 (11.1%) | 0 (0.0%) |
| MILD | 1 (14.3%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| FOLLICULITIS | 1 (14.3%) | 0 (0.0%) | 0 (0.0%) |
| MILD | 1 (14.3%) | 0 (0.0%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| HEADACHE | 1 (14.3%) | 1 (11.1%) | 0 (0.0%) |
| MILD | 1 (14.3%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| HEADACHE-TENSION TYPE | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| IMPACTED WISDOM TOOTH | 0 (0.0%) | 0 (0.0%) | 1 (25.0%) |
| MILD | 0 (0.0%) | 0 (0.0%) | 1 (25.0%) |
| MODERATE | 0 (0.0%) | 0 (0.0%) | 0 (0.0%) |
| SEVERE | 0 (0.0%) | 0 (0.0%) | 0 (0.0%) |
| LOSS OF APPETITE | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| LOWER JAW MOLAR TOOTH PAIN | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| MYALGIA | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| NAUSEA | 1 (14.3%) | 2 (22.2%) | 0 (0.0%) |
| MILD | 0 (0.0%) | 2 (22.2%) | 0 (0.0%) |
| MODERATE | 1 (14.3%) | 0 (0.0%) | 0 (0.0%) |
| SEVERE | 0 (0.0%) | 0 (0.0%) | 0 (0.0%) |
| PAIN BEHIND EYES | 1 (14.3%) | 0 (0.0%) | 0 (0.0%) |
| MILD | 1 (14.3%) | 0 (0.0%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| PAPULES ON ABDOMEN | 1 (14.3%) | 0 (0.0%) | 0 (0.0%) |
| MILD | 1 (14.3%) | 0 (0.0%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| POLYDIPSIE | 0 (0.0%) | 1 (11.1%) | 0 (0.0%) |
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| RAISED CREATININE KINASE | 0 (0.0%) | 1 (11.1%) | 0 (0.0%) |

TABLE 8-continued

Summary of Subjects by Adverse Event Term and
Severity - Multiple ascending dose (MAD)

NASH MAD Cohorts

| ADVERSE EVENT SEVERITY | M1 1.2 mg ALT-801 (N = 7) | M2 1.8 mg ALT-801 (N = 9) | PLACEBO (N = 4) |
|---|---|---|---|
| MILD | 0 (0.0%) | 1 (11.1%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| REDUCED APPETITE | 0 (0.0%) | 0 (0.0%) | 1 (25.0%) |
| MILD | 0 (0.0%) | 0 (0.0%) | 1 (25.0%) |
| MODERATE | 0 (0.0%) | 0 (0.0%) | 0 (0.0%) |
| SEVERE | 0 (0.0%) | 0 (0.0%) | 0 (0.0%) |
| RIGHT CUBITAL FOSSA DERMATITIS | 1 (14.3%) | 0 (0.0%) | 0 (0.0%) |
| MILD | 1 (14.3%) | 0 (0.0%) | 0 (0.0%) |
| MODERATE | 0 (0.0%) | 0 (0.0%) | 0 (0.0%) |
| SEVERE | 0 (0.0%) | 0 (0.0%) | 0 (0.0%) |
| RIGHT FOREARM SWELLING | 0 (0.0%) | 0 (0.0%) | 1 (25.0%) |
| MILD | 0 (0.0%) | 0 (0.0%) | 1 (25.0%) |
| MODERATE | 0 (0.0%) | 0 (0.0%) | 0 (0.0%) |
| SEVERE | 0 (0.0%) | 0 (0.0%) | 0 (0.0%) |
| URINARY TRACT INFECTION | 0 (0.0%) | 0 (0.0%) | 1 (25.0%) |
| MILD | 0 (0.0%) | 0 (0.0%) | 0 (0.0%) |
| MODERATE | 0 (0.0%) | 0 (0.0%) | 1 (25.0%) |
| SEVERE | 0 (0.0%) | 0 (0.0%) | 0 (0.0%) |
| URTI | 0 (0.0%) | 0 (0.0%) | 1 (25.0%) |
| MILD | 0 (0.0%) | 0 (0.0%) | 1 (25.0%) |
| MODERATE | 0 (0.0%) | 0 (0.0%) | 0 (0.0%) |
| SEVERE | 0 (0.0%) | 0 (0.0%) | 0 (0.0%) |

The analysis showed that a mean weight loss of 5.4% was achieved by Week 6 using a once weekly ALT-801 dose of 1.8 mg subcutaneously (SC) compared to a weight gain of 0.9% in the placebo group (net change from placebo of 6.3%), surpassing the pre-study treatment target of 2% weight loss. All but one of the 9 subjects who received the 1.8 mg SC dose achieved at least 3% weight loss by Week 6. A lower dose cohort that received a weekly 1.2 mg SC dose achieved a weight loss of 1.8% (net change from placebo of 2.7%) at the same time point. ALT-801 was well-tolerated without dose titration, with transient nausea rates of 14.3% at the 1.2 mg dose and 22.2% at the 1.8 mg dose, respectively, and no reports of vomiting, diarrhea or constipation at either dose. These results place ALT-801 among the most effective and well-tolerated of GLP-1 based therapeutics. Gastrointestinal events have required other GLP-1 based agents to dose titrate over 16 to 20 weeks to maintain adequate tolerability.

Example 5. ALT-801 (Pemvidutide) Phase 1 Study in Overweight and Obese Volunteers—12-Week Results This example presents the results of a Phase 1 clinical trial with ALT-801 (Pemvidutide) that is a placebo-controlled, first-in-human, single ascending dose (SAD) and multiple ascending dose (MAD) study in overweight and obese volunteers being conducted in Australia under a clinical trial application. The primary objectives of the study were to assess the safety and tolerability, pharmacokinetics, and weight loss in subjects administered ALT-801 compared to placebo over 12 weeks of once weekly dosing. The study was performed in the absence of calorie restriction or behavioral weight loss programs. In certain embodiments, ALT-801 (also known as Pemvidutide) may be used as a treatment for chronic weight management in obese (i.e., BMI of 30 or greater) or overweight (i.e., BMI of 25 of greater) subjects as a primary and standalone treatment. In certain other embodiments, ALT-801 (also known as Pemvidutide) may be used as an adjunct treatment for chronic weight management in obese (i.e., BMI of 30 or greater) or overweight (i.e., BMI of 25 of greater) subjects in combination with a reduced calorie diet and/or increased physical activity.

Eligible participants included healthy, non-diabetic subjects with a minimum body mass index (BMI) of 25 kg/m2. Thirty-four (34) subjects in the MAD portion of the study were assigned to receive one of three subcutaneous doses of Pemvidutide (1.2 mg, 1.8 mg and 2.4 mg) or placebo once weekly for 12 weeks without dose titration. Behavioral and caloric restrictive interventions were not employed. Dosing in the MAD phase commenced with a cohort receiving 1.2 mg SC of ALT-801 or placebo once weekly and has progressed through higher dose cohorts, with subjects in the 1.2 mg, 1.8 mg and 2.4 mg ALT-801 dose cohorts having completed 12 weeks of treatment as presented in this example. Demographics of the participants in the MAD phase are presented in Table 9.

TABLE 9

Demographics of the participants (MAD)

| | | Treatment | | | |
|---|---|---|---|---|---|
| Characteristic | | 1.2 mg | 1.8 mg | 2.4 mg | Pooled placebo |
| Age, years | mean (SD) | 27.7 (11) | 32.0 (11) | 31.4 (12) | 35.3 (12) |
| Sex | female, n (%) | 1 (14%) | 4 (44%) | 7 (64%) | 4 (57%) |
| | male, n (%) | 6 (86%) | 5 (56%) | 4 (36%) | 3 (43%) |
| Race | Caucasian, n (%) | 4 (57%) | 5 (56%) | 8 (67%) | 5 (71%) |
| | Caucasian Hispanic, n (%) | 0 (0%) | 1 (11%) | 0 (0%) | 1 (14%) |
| | Asian, n (%) | 2 (29%) | 3 (33%) | 3 (25%) | 1 (14%) |
| | African, n (%) | 1 (14%) | 0 (0%) | 0 (0%) | 0 (0%) |
| Body Weight, kg | mean (SD) | 90.5 (15) | 86.4 (13) | 91.9 (15) | 87.6 (14) |
| BMI, kg/m$^2$ | mean (SD) | 30.0 (4) | 30.1 (4) | 31.8 (3) | 31.0 (4) |

Note:
BMI = Body Mass Index

Figure 2:
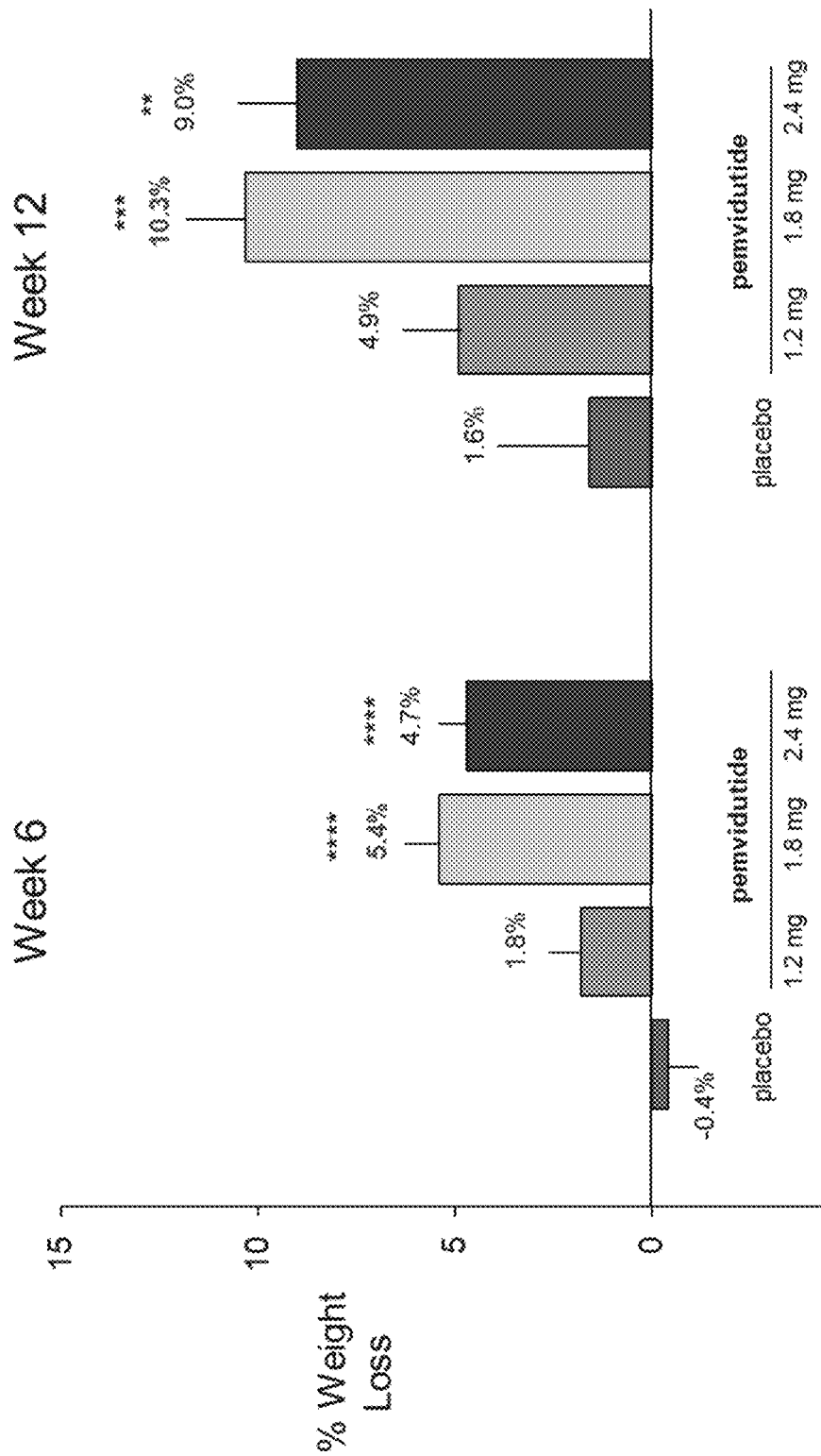
FIG. 2 illustrates the weight loss results following weekly administration of ALT-801 (Pemvidutide) after 6 and 12 week treatment across the different dose groups (1.2 mg, 1.8 mg and 2.4 mg) versus placebo group.
Figure 3:
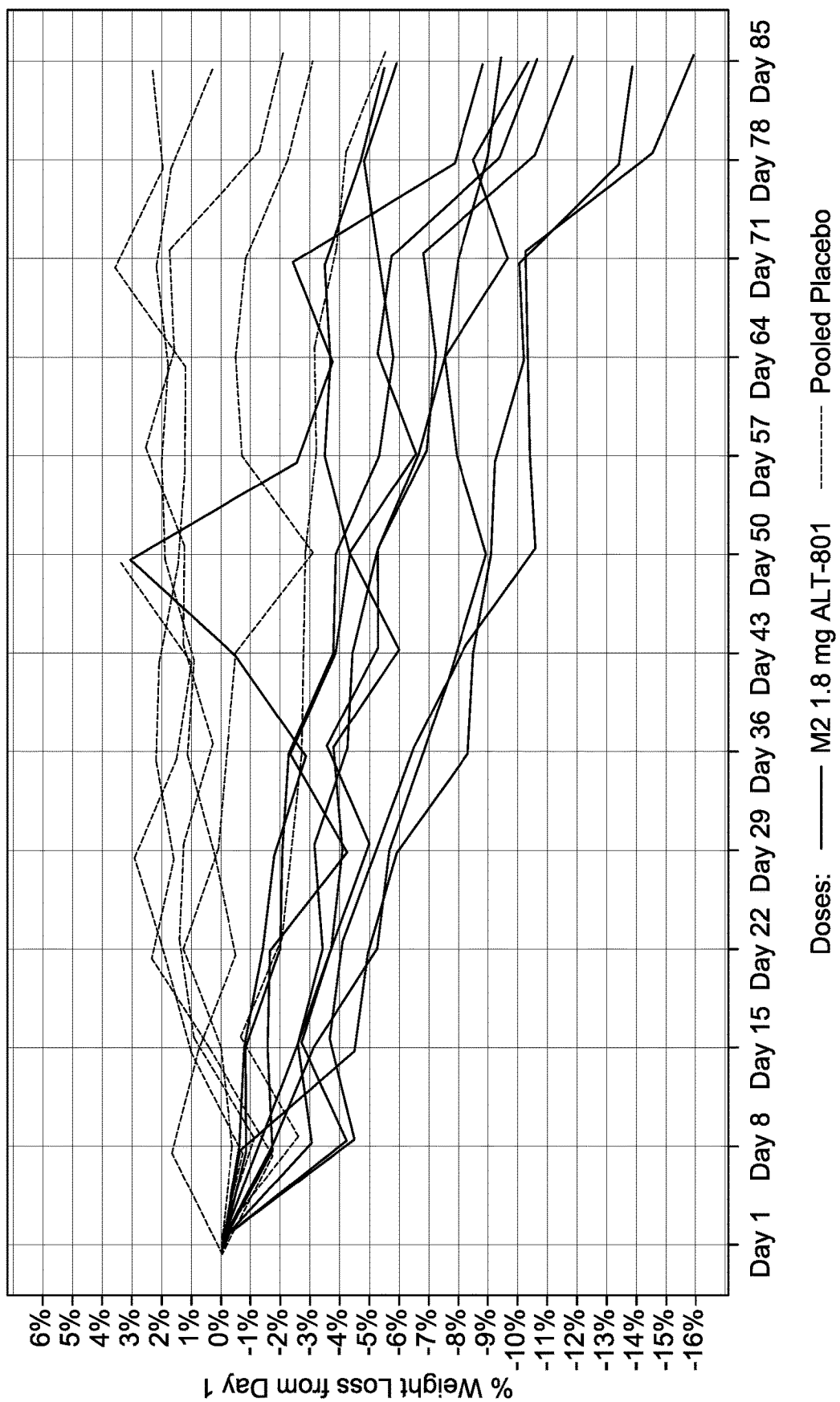
FIG. 3 illustrates the individual subject weight loss results following weekly administration of ALT-801 at 1.8 mg for 12 weeks versus placebo.
Figure 4:
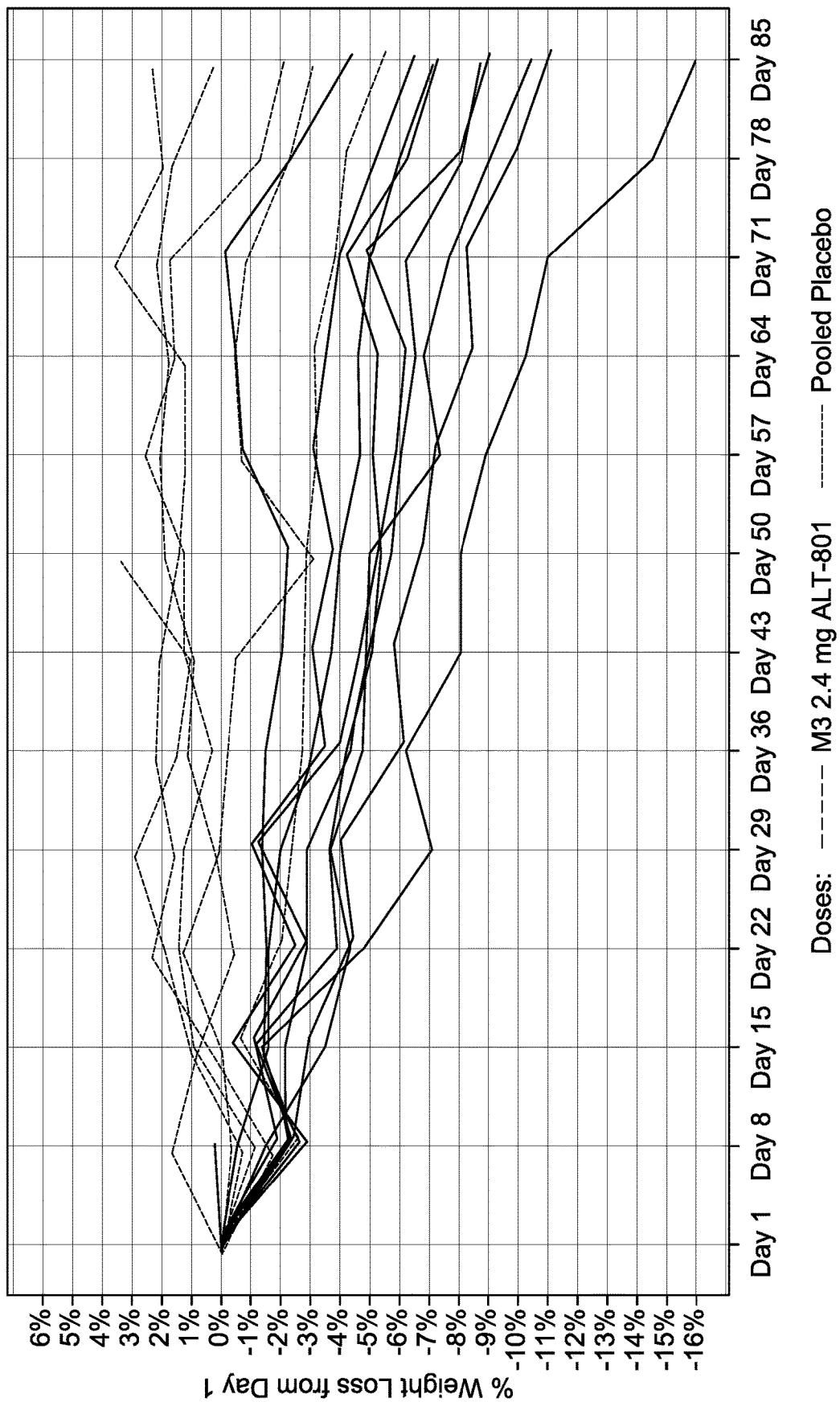
FIG. 4 illustrates the individual subject weight loss results following weekly administration of ALT-801 at 2.4 mg for 12 weeks versus placebo.
Figure 5B:
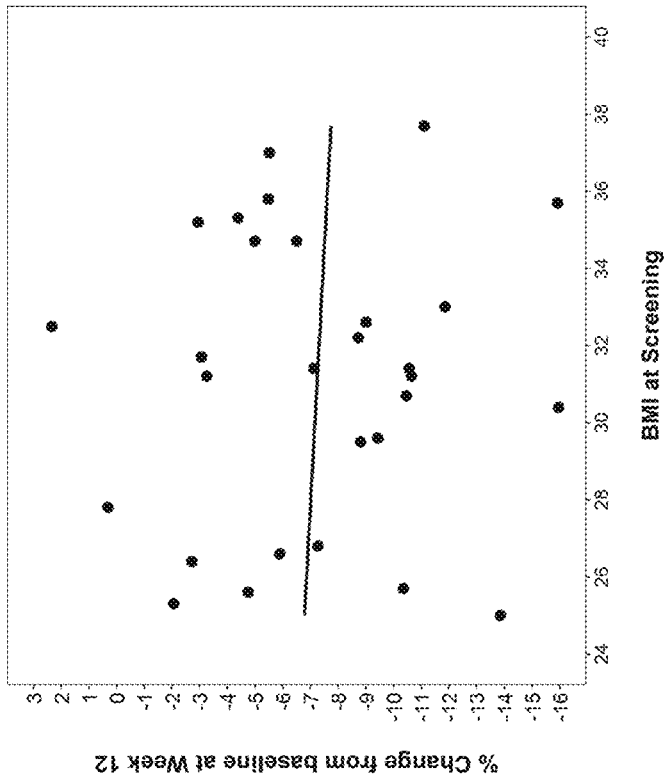
FIG. 5A and FIG. 5B illustrate the absence of correlation between weight loss and age or BMI (Body Mass Index) respectively.
Figure 5A:
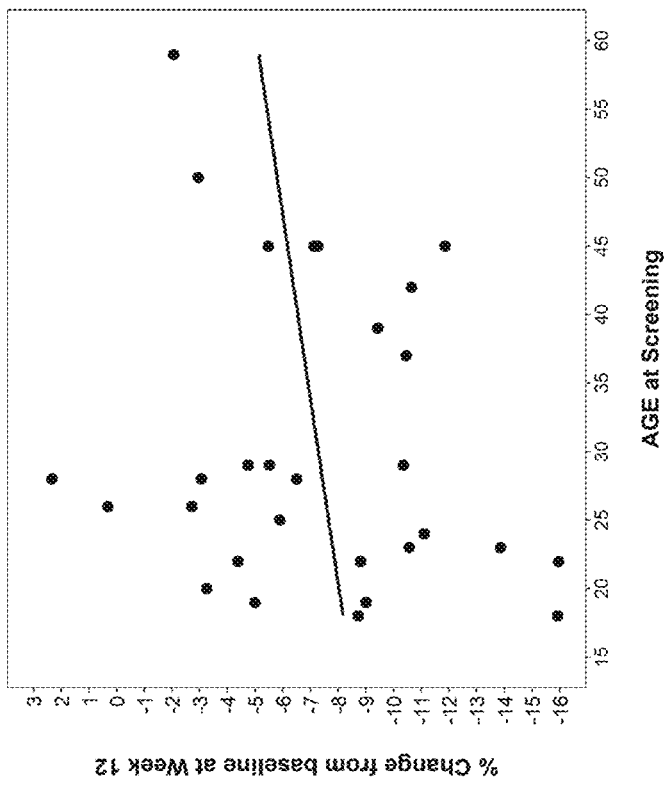

Results of weight loss following weekly dosing with ALT-801 in healthy overweight and obese volunteers are presented in Table 10. Results show that ALT-801 induces rapid and robust weight loss in healthy overweight and obese volunteers. Using a once weekly ALT-801 dose of 1.8 mg subcutaneously (SC), a mean weight loss of 10.25% was achieved by Week 12 (Day 85) compared to a mean weight loss of only 1.6% in the placebo group (Table 10, FIG. 2). Moreover, at the 1.8 mg dose, 100% of subjects achieved 5% or more weight loss by Week 12 and 55% of subjects losing at least 10% of their body weight by Week 12. (FIG. 2). At week 12, a lower dose cohort that received a weekly 1.2 mg SC dose achieved a weight loss of 4.87% while the higher dose cohort receiving weekly 2.4 mg SC dose achieved a weight loss of 8.95% (Table 10). At the 2.4 mg dose, all but one subject achieved 5% weight loss by Week 12 (FIG. 3). The amounts of weight loss at the 1.8 and 2.4 mg doses were essentially the same given the sample size and overlapping confidence intervals. As showed in FIGS. 3 and 4, weight loss trends were maintained through Week 12 indicative of higher level of weight loss anticipated if dosing was to be maintain for longer periods of time. By comparison, in participants with overweight or obesity, the mean change in body weight from baseline to week 12 at a dose of 2.4 mg of semaglutide once weekly plus lifestyle intervention was only 6% (Wilding J P H, Batterham R L, Calanna S, Davies M, Van Gaal L F, Lingvay I, McGowan B M, Rosenstock J, Tran M T D, Wadden T A, Wharton S, Yokote K, Zeuthen N, Kushner R F; STEP 1 Study Group. Once-Weekly Semaglutide in Adults with Overweight or Obesity. N Engl J Med. 2021 Mar. 18; 384(11):989). Interestingly, no correlation between body weight loss at week 12 across the different ALT-801 dose groups and subject age or BMI (Body Mass Index; $kg/m^2$) was found (FIG. 5), meaning that the robust weight loss observed in this study would be expected in all age and weight groups.

TABLE 10

Weight - Observed Results and Change from Baseline by Timepoint - Multiple Ascending Dose (MAD)

| Visit Statistic | Overall ALT-801 (N = 27) | 1.2 mg ALT-801 (N = 7) | 1.8 mg ALT-801 (N = 9) | 2.4 mg ALT-801 (N = 11) | PLACEBO (N = 7) |
|---|---|---|---|---|---|
| Baseline [1] | | | | | |
| n | 27 | 7 | 9 | 11 | 7 |
| Mean (SD) | 89.71 (14.1) | 90.54 (15.4) | 86.41 (12.9) | 91.87 (15.1) | 87.56 (14.3) |
| Median | 92.8 | 95.5 | 90.1 | 94.6 | 85.6 |
| Min, Max | 62.8, 118 | 63.8, 106.2 | 62.8, 104.4 | 68.8, 118 | 62.8, 108.8 |
| Weight (kg) Day 8 | | | | | |
| n | 26 | 6 | 9 | 11 | 7 |
| Mean (SD) | 89.03 (13.2) | 93.78 (10.8) | 84.57 (12.3) | 90.1 (15) | 87.13 (14.2) |
| Median | 89.15 | 95.2 | 88.9 | 92.3 | 85 |
| Min, Max | 62.4, 116.3 | 78.5, 105.9 | 62.4, 102.6 | 67, 116.3 | 62.1, 106 |
| Change from Baseline (kg) to Day 8 | | | | | |
| n | 26 | 6 | 9 | 11 | 7 |
| Mean (SD) | −1.67 (1.1) | −1.22 (1) | −1.84 (1.4) | −1.77 (0.9) | −0.43 (1.5) |
| Median | −1.75 | −1.1 | −1.2 | −2 | −0.6 |
| Min, Max | −4.2, 0.2 | −2.9, −0.2 | −4.2, −0.4 | −3, 0.2 | −2.8, 1.6 |
| % Change from Baseline to Day 8 | | | | | |
| n | 26 | 6 | 9 | 11 | 7 |
| Mean (SD) | −1.84 (1.2) | −1.28 (1.1) | −2.06 (1.5) | −1.96 (1) | −0.5 (1.5) |
| Median | −1.79 | −1.12 | −1.7 | −2.24 | −0.7 |
| Min, Max | −4.49, 0.25 | −2.95, −0.24 | −4.49, −0.6 | −3.23, 0.25 | −2.57, 1.68 |
| P-value vs. Placebo [2] | 0.2582 | 1.0000 | 0.2483 | 0.2086 | NA |
| Weight (kg) Day 15 | | | | | |
| n | 24 | 6 | 9 | 9 | 6 |
| Mean (SD) | 90.39 (13.1) | 94.3 (10.6) | 84.37 (13.1) | 93.8 (13.6) | 86.77 (15) |
| Median | 91.05 | 95.3 | 87.8 | 96.8 | 85.7 |
| Min, Max | 60, 114 | 79.3, 105.9 | 60, 102.8 | 68, 114 | 63.4, 108.1 |
| Change from Baseline (kg) to Day 15 | | | | | |
| n | 24 | 6 | 9 | 9 | 6 |
| Mean (SD) | −1.57 (1.1) | −0.7 (1.1) | −2.04 (0.9) | −1.68 (1.1) | 0.3 (0.6) |
| Median | −1.5 | −0.6 | −2.2 | −1.4 | 0.4 |
| Min, Max | −4, 0.7 | −2.6, 0.7 | −3.4, −0.7 | −4, −0.4 | −0.7, 0.9 |
| % Change from Baseline to Day 15 | | | | | |
| n | 24 | 6 | 9 | 9 | 6 |
| Mean (SD) | −1.74 (1.3) | −0.72 (1.1) | −2.46 (1.2) | −1.72 (1) | 0.41 (0.7) |
| Median | −1.48 | −0.6 | −2.57 | −1.43 | 0.54 |
| Min, Max | −4.46, 0.83 | −2.64, 0.83 | −4.46, −0.74 | −3.39, −0.38 | −0.64, 1.05 |
| P-value vs. Placebo [2] | 0.0001 | 0.2758 | 0.0003 | 0.0008 | NA |

TABLE 10-continued

Weight - Observed Results and Change from Baseline
by Timepoint - Multiple Ascending Dose (MAD)

| Visit Statistic | Overall ALT-801 (N = 27) | 1.2 mg ALT-801 (N = 7) | 1.8 mg ALT-801 (N = 9) | 2.4 mg ALT-801 (N = 11) | PLACEBO (N = 7) |
|---|---|---|---|---|---|
| Weight (kg) Day 22 | | | | | |
| n | 24 | 6 | 9 | 9 | 6 |
| Mean (SD) | 89.7 (13.1) | 94.63 (9.7) | 83.63 (13.3) | 92.47 (13.9) | 86.95 (14.2) |
| Median | 90.1 | 94.7 | 87 | 96.7 | 86.6 |
| Min, Max | 59.7, 112.9 | 79.4, 105.1 | 59.7, 102.7 | 66.1, 112.9 | 63.7, 106.6 |
| Change from Baseline (kg) to Day 22 | | | | | |
| n | 24 | 6 | 9 | 9 | 6 |
| Mean (SD) | −2.26 (1.9) | −0.37 (2.8) | −2.78 (1) | −3.01 (1.2) | 0.48 (1.5) |
| Median | −2.65 | −1.05 | −3.1 | −2.7 | 1 |
| Min, Max | −5.1, 5.1 | −2.9, 5.1 | −3.8, −1.3 | −5.1, −1.5 | −2.2, 1.9 |
| % Change from Baseline to Day 22 | | | | | |
| n | 24 | 6 | 9 | 9 | 6 |
| Mean (SD) | −2.51 (2.3) | −0.24 (3.2) | −3.35 (1.4) | −3.2 (1.2) | 0.75 (1.6) |
| Median | −2.87 | −0.99 | −3.74 | −2.89 | 1.36 |
| Min, Max | −5.25, 6.05 | −2.95, 6.05 | −5.25, −1.37 | −4.75, −1.53 | −2.02, 2.34 |
| P-value vs. Placebo [2] | 0.0095 | 1.0000 | 0.0024 | 0.0033 | NA |
| Weight (kg) Day 29 | | | | | |
| n | 24 | 6 | 9 | 9 | 5 |
| Mean (SD) | 89.33 (13.4) | 93.82 (10.4) | 82.92 (12.8) | 92.74 (14.5) | 82.98 (11.9) |
| Median | 89.7 | 94.15 | 87.3 | 96.9 | 85 |
| Min, Max | 59.1, 113.7 | 79.5, 105.3 | 59.1, 100 | 66.3, 113.7 | 63.6, 95.6 |
| Change from Baseline (kg) to Day 29 | | | | | |
| n | 24 | 6 | 9 | 9 | 5 |
| Mean (SD) | −2.63 (1.7) | −1.18 (1.5) | −3.49 (1.2) | −2.73 (1.6) | 0.98 (1) |
| Median | −2.55 | −0.9 | −3.7 | −2.5 | 0.8 |
| Min, Max | −5.8, 0.5 | −3.9, 0.5 | −5, −1.7 | −5.8, −1.1 | 0.1, 2.5 |
| % Change from Baseline to Day 29 | | | | | |
| n | 24 | 6 | 9 | 9 | 5 |
| Mean (SD) | −2.96 (2) | −1.2 (1.6) | −4.12 (1.5) | −2.98 (1.9) | 1.22 (1.1) |
| Median | −3 | −0.94 | −4.21 | −2.89 | 1.27 |
| Min, Max | −7.06, 0.59 | −3.96, 0.59 | −5.89, −1.79 | −7.06, −1.05 | 0.12, 2.92 |
| P-value vs. Placebo [2] | 0.0003 | 0.0659 | 0.0001 | 0.0011 | NA |
| Weight (kg) Day 36 | | | | | |
| n | 24 | 6 | 9 | 9 | 6 |
| Mean (SD) | 88.76 (13.3) | 93.72 (10) | 82.7 (13.5) | 91.52 (13.9) | 86.68 (14.4) |
| Median | 89.15 | 93.95 | 86.3 | 96.7 | 85.85 |
| Min, Max | 57.6, 112.4 | 79.8, 105.5 | 57.6, 102 | 65.9, 112.4 | 63, 105.8 |
| Change from Baseline (kg) to Day 36 | | | | | |
| n | 24 | 6 | 9 | 9 | 6 |
| Mean (SD) | −3.2 (1.8) | −1.28 (1.9) | −3.71 (1.4) | −3.96 (1.4) | 0.22 (1.7) |
| Median | −3.25 | −1.3 | −3.3 | −3.9 | 0.65 |
| Min, Max | −6.1, 1.3 | −3.7, 1.3 | −6.1, −1.9 | −5.8, −1.5 | −3, 1.8 |
| % Change from Baseline to Day 36 | | | | | |
| n | 24 | 6 | 9 | 9 | 6 |
| Mean (SD) | −3.57 (2.3) | −1.26 (2) | −4.51 (2.2) | −4.19 (1.5) | 0.39 (1.8) |
| Median | −3.65 | −1.39 | −3.74 | −4.22 | 0.74 |
| Min, Max | −8.28, 1.54 | −3.76, 1.54 | −8.28, −2.29 | −6.21, −1.53 | −2.76, 2.21 |
| P-value vs. Placebo [2] | 0.0039 | 0.6317 | 0.0016 | 0.0017 | NA |
| Weight (kg) Day 43 | | | | | |
| n | 24 | 6 | 9 | 9 | 6 |
| Mean (SD) | 88.19 (13.4) | 93.2 (10.1) | 81.94 (13.5) | 91.09 (14.1) | 86.62 (14.2) |
| Median | 88.5 | 93.7 | 85.9 | 96.2 | 85.5 |
| Min, Max | 57.5, 112.2 | 78.7, 104.4 | 57.5, 100.4 | 65.3, 112.2 | 63.6, 105.8 |
| Change from Baseline (kg) to Day 43 | | | | | |
| n | 24 | 6 | 9 | 9 | 6 |
| Mean (SD) | −3.77 (2.1) | −1.8 (1.9) | −4.47 (2) | −4.39 (1.4) | 0.15 (1.7) |
| Median | −4 | −1.45 | −4.9 | −4.4 | 0.85 |
| Min, Max | −7.7, 0.8 | −5, 0.8 | −7.7, −0.5 | −6.6, −2 | −3, 1.7 |

TABLE 10-continued

Weight - Observed Results and Change from Baseline
by Timepoint - Multiple Ascending Dose (MAD)

| Visit Statistic | Overall ALT-801 (N = 27) | 1.2 mg ALT-801 (N = 7) | 1.8 mg ALT-801 (N = 9) | 2.4 mg ALT-801 (N = 11) | PLACEBO (N = 7) |
|---|---|---|---|---|---|
| % Change from Baseline to Day 43 | | | | | |
| n | 24 | 6 | 9 | 9 | 6 |
| Mean (SD) | −4.23 (2.5) | −1.82 (2) | −5.38 (2.6) | −4.69 (1.7) | 0.36 (1.7) |
| Median | −4.57 | −1.66 | −5.28 | −4.89 | 1 |
| Min, Max | −8.44, 0.95 | −5.08, 0.95 | −8.44, −0.53 | −8.04, −2.04 | −2.76, 2.09 |
| P-value vs. Placebo [2] | 0.0011 | 0.2792 | 0.0008 | 0.0008 | NA |
| Weight (kg) Day 50 | | | | | |
| n | 24 | 6 | 9 | 9 | 6 |
| Mean (SD) | 88 (13.4) | 93.07 (9.7) | 81.97 (14) | 90.66 (13.9) | 86.63 (14.5) |
| Median | 88.05 | 93.5 | 83.7 | 96 | 85.5 |
| Min, Max | 57.1, 111.3 | 79, 104.4 | 57.1, 99.9 | 65.1, 111.3 | 63.6, 105.7 |
| Change from Baseline (kg) to Day 50 | | | | | |
| n | 24 | 6 | 9 | 9 | 6 |
| Mean (SD) | −3.96 (2.7) | −1.93 (2.3) | −4.44 (3.4) | −4.82 (1.6) | 0.17 (2.4) |
| Median | −4.25 | −1.45 | −4.7 | −4.5 | 1 |
| Min, Max | −9.9, 2.9 | −5.1, 1.3 | −9.9, 2.9 | −6.7, −2.2 | −3.1, 2.9 |
| % Change from Baseline to Day 50 | | | | | |
| n | 24 | 6 | 9 | 9 | 6 |
| Mean (SD) | −4.42 (3.2) | −1.92 (2.3) | −5.39 (4) | −5.12 (1.7) | 0.35 (2.7) |
| Median | −4.67 | −1.63 | −5.22 | −5.29 | 1.37 |
| Min, Max | −10.58, 3.06 | −5.18, 1.54 | −10.58, 3.06 | −8.04, −2.24 | −3.06, 3.39 |
| P-value vs. Placebo [2] | 0.0181 | 0.5835 | 0.0218 | 0.0092 | NA |
| Weight (kg) Day 57 | | | | | |
| n | 24 | 6 | 9 | 9 | 5 |
| Mean (SD) | 87.51 (13.4) | 93.1 (9.9) | 80.91 (13.3) | 90.38 (14.1) | 86.74 (15.7) |
| Median | 87.1 | 93.3 | 83.9 | 96.1 | 84.3 |
| Min, Max | 57, 110.9 | 78.8, 104.4 | 57, 100.8 | 65.3, 110.9 | 64.4, 105.3 |
| Change from Baseline (kg) to Day 57 | | | | | |
| n | 24 | 6 | 9 | 9 | 5 |
| Mean (SD) | −4.45 (2.5) | −1.9 (2.1) | −5.5 (2) | −5.1 (2.2) | 0.1 (2.2) |
| Min, Max | −9.7, 1.4 | −4.7, 1.4 | −9.7, −2.4 | −7.3, −0.7 | −3.5, 2 |
| % Change from Baseline to Day 57 | | | | | |
| n | 24 | 6 | 9 | 9 | 5 |
| Mean (SD) | −4.97 (3) | −1.9 (2.2) | −6.55 (2.5) | −5.43 (2.4) | 0.39 (2.4) |
| Median | −5.19 | −2.17 | −6.66 | −5.88 | 1.23 |
| Min, Max | −10.36, 1.66 | −4.78, 1.66 | −10.36, −2.53 | −8.89, −0.71 | −3.22, 2.55 |
| P-value vs. Placebo [2] | 0.0132 | 0.5357 | 0.0026 | 0.0082 | NA |
| Weight (kg) Day 64 | | | | | |
| n | 24 | 6 | 9 | 9 | 5 |
| Mean (SD) | 87.15 (13.3) | 92.48 (9.6) | 80.68 (13.2) | 90.06 (14.1) | 86.62 (15.9) |
| Median | 86.35 | 92.45 | 83.3 | 95.8 | 84.5 |
| Min, Max | 56.4, 110.3 | 79.2, 103.5 | 56.4, 100.5 | 65.2, 110.3 | 63.8, 105.4 |
| Change from Baseline (kg) to Day 64 | | | | | |
| n | 24 | 6 | 9 | 9 | 5 |
| Mean (SD) | −4.81 (2.6) | −2.52 (2.3) | −5.73 (1.9) | −5.42 (2.6) | −0.02 (2) |
| Median | −4.7 | −2.3 | −5.3 | −6.1 | 1 |
| Min, Max | −9.7, 0.3 | −6.4, 0.3 | −9.7, −3.5 | −8.4, −0.5 | −3.4, 1.7 |
| % Change from Baseline to Day 64 | | | | | |
| n | 24 | 6 | 9 | 9 | 5 |
| Mean (SD) | −5.35 (3) | −2.53 (2.3) | −6.81 (2.4) | −5.77 (2.8) | 0.2 (2.1) |
| Median | −5.52 | −2.31 | −7.22 | −6.17 | 1.23 |
| Min, Max | −10.36, 0.36 | −6.5, 0.36 | −10.36, −3.69 | −10.23, −0.51 | −3.12, 1.78 |
| P-value vs. Placebo [2] | 0.0041 | 0.2774 | 0.0009 | 0.0036 | NA |
| Weight (kg) Day 71 | | | | | |
| n | 24 | 6 | 9 | 9 | 5 |
| Mean (SD) | 87.17 (13.4) | 92.42 (9.1) | 80.71 (13.7) | 90.13 (14.2) | 86.88 (15.6) |
| Median | 86.65 | 92.45 | 82.9 | 96 | 84.2 |
| Min, Max | 56.5, 110.7 | 80.5, 103 | 56.5, 101.9 | 65.9, 110.7 | 63.9, 104.6 |

TABLE 10-continued

Weight - Observed Results and Change from Baseline
by Timepoint - Multiple Ascending Dose (MAD)

| Visit Statistic | Overall ALT-801 (N = 27) | 1.2 mg ALT-801 (N = 7) | 1.8 mg ALT-801 (N = 9) | 2.4 mg ALT-801 (N = 11) | PLACEBO (N = 7) |
|---|---|---|---|---|---|
| Change from Baseline (kg) to Day 71 | | | | | |
| n | 24 | 6 | 9 | 9 | 5 |
| Mean (SD) | −4.79 (2.7) | −2.58 (2.6) | −5.7 (2.2) | −5.34 (2.8) | 0.24 (2.8) |
| Median | −4.95 | −2.5 | −6.3 | −5 | 1.1 |
| Min, Max | −9.6, 0.4 | −6.5, 0.4 | −9.6, −2.5 | −9, −0.1 | −4.2, 2.9 |
| % Change from Baseline to Day 71 | | | | | |
| n | 24 | 6 | 9 | 9 | 5 |
| Mean (SD) | −5.34 (3.3) | −2.55 (2.6) | −6.85 (2.9) | −5.68 (3.1) | 0.57 (2.9) |
| Median | −5.12 | −2.49 | −6.79 | −4.95 | 1.75 |
| Min, Max | −10.96, 0.5 | −6.61, 0.5 | −10.26, −2.39 | −10.96, −0.1 | −3.86, 3.57 |
| P-value vs. Placebo [2] | 0.0262 | 0.4041 | 0.0070 | 0.0194 | NA |
| Weight (kg) Day 78 | | | | | |
| n | 24 | 6 | 9 | 9 | 5 |
| Mean (SD) | 85.25 (13.2) | 90.82 (9.9) | 78.58 (12.6) | 88.21 (14.2) | 85.82 (16.2) |
| Median | 84.1 | 90.35 | 80 | 93.9 | 83 |
| Min, Max | 54.4, 108.5 | 77.6, 102.4 | 54.4, 96.2 | 64.5, 108.5 | 62, 104.2 |
| Change from Baseline (kg) to Day 78 | | | | | |
| n | 24 | 6 | 9 | 9 | 5 |
| Mean (SD) | −6.71 (3.2) | −4.18 (2.9) | −7.83 (2.9) | −7.27 (3) | −0.82 (2.6) |
| Median | −7 | −3.35 | −8.1 | −8.2 | −0.8 |
| Min, Max | −13.6, −1.4 | −9.6, −1.4 | −13.6, −4 | −11.9, −2.4 | −4.6, 1.6 |
| % Change from Baseline to Day 78 | | | | | |
| n | 24 | 6 | 9 | 9 | 5 |
| Mean (SD) | −7.42 (3.7) | −4.31 (2.8) | −9.18 (3.4) | −7.73 (3.4) | −0.82 (2.6) |
| Median | −7.94 | −3.45 | −8.99 | −8.03 | −1.27 |
| Min, Max | −14.53, −1.66 | −9.76, −1.66 | −14.53, −4.64 | −14.49, −2.44 | −4.23, 1.97 |
| P-value vs. Placebo [2] | 0.0068 | 0.2583 | 0.0016 | 0.0065 | NA |
| Weight (kg) Day 85 | | | | | |
| n | 24 | 6 | 9 | 9 | 5 |
| Mean (SD) | 84.35 (13.3) | 90.33 (10.3) | 77.66 (12.5) | 87.06 (14.1) | 85.1 (15.8) |
| Median | 83.05 | 90.2 | 78.7 | 92.9 | 83.2 |
| Min, Max | 54.1, 107.7 | 76.3, 102.4 | 54.1, 95.2 | 63.8, 107.7 | 61.5, 102.8 |
| Change from Baseline (kg) to Day 85 | | | | | |
| n | 24 | 6 | 9 | 9 | 5 |
| Mean (SD) | −7.61 (3.3) | −4.67 (3) | −8.76 (3) | −8.42 (2.8) | −1.54 (3) |
| Median | −7.9 | −3.45 | −8.7 | −9.2 | −1.3 |
| Min, Max | −14.9, −2.3 | −10.4, −2.3 | −14.9, −4.9 | −13.1, −4.3 | −6, 1.9 |
| % Change from Baseline to Day 85 | | | | | |
| n | 24 | 6 | 9 | 9 | 5 |
| Mean (SD) | −8.42 (3.8) | −4.87 (2.9) | −10.25 (3.4) | −8.95 (3.3) | −1.6 (3) |
| Median | −8.77 | −4 | −10.35 | −8.73 | −2.07 |
| Min, Max | −15.96, −2.73 | −10.57, −2.73 | −15.92, −5.48 | −15.96, −4.38 | −5.51, 2.34 |
| P-value vs. Placebo [2] | 0.0136 | 0.4270 | 0.0031 | 0.0091 | NA |

Note:

SD = Standard deviation, min = minimum, max = maximum

[1] Baseline is defined as the last non-missing value collected prior to receiving first dose of study drug.

[2] Bonferroni adjusted p-values. P-values are from Student's t-test comparing the % changes from baseline in each ALT-801 dose group to the % changes in the pooled placebo.

Adverse events for 12-week monitoring are presented in Table 11. Results shows that ALT-801 is well-tolerated without the need for dose titration. All Treatment-Emergent Adverse Events were mild to moderate in nature with on drug resolution and not requiring specific treatment. One patient experienced elevated ALT levels that resolved rapidly after a pause in dosing. In particular, gastrointestinal adverse events were in majority transient, mild, with on-drug resolution. In addition, these gastrointestinal adverse events were transient in nature, with subjects often experienced single episodes and with frequency decreasing over treatment period. No subject withdrew from the study for adverse events (see Table 12). Gastrointestinal events have required other GLP-1-based agents to dose titrate over 16 to 20 weeks to maintain adequate tolerability. For example, WEGOVY (Semaglutide), approved for chronic weight management in adult patients (https://www.acces sdata.fda.gov/drugsatfda_docs/label/2021/215256s0001b1.pdf) necessitates a 16 weeks dose escalation from 0.5 to 2.4 mg to manage the emergence of adverse events. These results place ALT-801 amongst the most effective and well-tolerated of GLP-1 based therapeutics.

TABLE 11

Treatment-Emergent Adverse Events (TEAEs) by System Organ Class, Preferred Term, and Maximum Severity: Part 2 (MAD) Safety Population

| System Organ Class Preferred Term [n (%)] | Maximum Severity [1] | Overall ALT-801 (N = 27) | M1 1.2 mg ALT-801 (N = 7) | M2 1.8 mg ALT-801 (N = 9) | M3 2.4 mg ALT-801 (N = 11) | MAD PLACEDO (N = 7) |
|---|---|---|---|---|---|---|
| Any TEAE | Mild | 12 (44.4%) | 1 (14.3%) | 5 (55.6%) | 6 (54.5%) | 3 (42.9%) |
| | Moderate | 11 (40.7%) | 2 (28.6%) | 4 (44.4%) | 5 (45.5%) | 2 (28.6%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Blood and lymphatic system disorders | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Anaemia | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Cardiac disorders | Mild | 2 (7.4%) | 0 (0.0%) | 0 (0.0%) | 2 (18.2%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Palpitation | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Tachycardia | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Eye disorders | Mild | 1 (3.7%) | 1 (14.3%) | 0 (0.0%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Eye pain | Mild | 1 (3.7%) | 1 (14.3%) | 0 (0.0%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Gastrointestinal disorders | Mild | 11 (40.7%) | 1 (14.3%) | 5 (55.6%) | 5 (45.5%) | 2 (28.6%) |
| | Moderate | 9 (33.3%) | 1 (14.3%) | 3 (33.3%) | 5 (45.5%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Abdominal discomfort | Mild | 2 (7.4%) | 0 (0.0%) | 1 (11.1%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Abdominal distension | Mild | 1 (3.7%) | 0 (0.0%) | 0 (0.0%) | 1 (9.1%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Abdominal pain | Mild | 5 (18.5%) | 0 (0.0%) | 1 (11.1%) | 4 (36.4%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Constipation | Mild | 3 (11.1%) | 0 (0.0%) | 1 (11.1%) | 2 (18.2%) | 0 (0.0%) |
| | Moderate | 2 (7.4%) | 0 (0.0%) | 1 (11.1%) | 1 (9.1%) | 0 (0.0%) |
| | Severe | 0 (0.0%) | 0 (0.0%) | 0 (0.0%) | 0 (0.0%) | 0 (0.0%) |
| | Potentially PLT | 0 (0.0%) | 0 (0.0%) | 0 (0.0%) | 0 (0.0%) | 0 (0.0%) |
| Diarrhoea | Mild | 2 (7.4%) | 0 (0.0%) | 0 (0.0%) | 2 (18.2%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |

TABLE 11-continued

Treatment-Emergent Adverse Events (TEAEs) by System Organ Class, Preferred
Term, and Maximum Severity: Part 2 (MAD) Safety Population

| System Organ Class Preferred Term [n (%)] | Maximum Severity [1] | Overall ALT-801 (N = 27) | M1 1.2 mg ALT-801 (N = 7) | M2 1.8 mg ALT-801 (N = 9) | M3 2.4 mg ALT-801 (N = 11) | MAD PLACEDO (N = 7) |
|---|---|---|---|---|---|---|
| Dyspepsia | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Food poisoning | Mild | 0 (0.0%) | 0 (0.0%) | 0 (0.0%) | 0 (0.0%) | 0 (0.0%) |
| | Moderate | 1 (3.7%) | 0 (0.0%) | 1 (11.1%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Haematemesis | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Nausea | Mild | 11 (40.7%) | 1 (14.3%) | 5 (55.6%) | 5 (45.5%) | 1 (14.3%) |
| | Moderate | 7 (25.9%) | 1 (14.3%) | 1 (11.1%) | 5 (45.5%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Rectal haemorrhage | Mild | 2 (7.4%) | 0 (0.0%) | 1 (11.1%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Tooth impacted | Mild | 0 (0.0%) | 0 (0.0%) | 0 (0.0%) | 0 (0.0%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Toothache | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Vomiting | Mild | 7 (25.9%) | 1 (14.3%) | 1 (11.1%) | 5 (45.5%) | 1 (14.3%) |
| | Moderate | 4 (14.8%) | 0 (0.0%) | 1 (11.1%) | 3 (27.3%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| General disorders and administration site conditions | Mild | 7 (25.9%) | 1 (14.3%) | 4 (44.4%) | 2 (18.2%) | 2 (28.6%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Application site bruise | Mild | 0 (0.0%) | 0 (0.0%) | 0 (0.0%) | 0 (0.0%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Application site erythema | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Early satiety | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Fatigue | Mild | 2 (7.4%) | 1 (14.3%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Injection site bruising | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Injection site dermatitis | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Peripheral swelling | Mild | 0 (0.0%) | 0 (0.0%) | 0 (0.0%) | 0 (0.0%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Vessel puncture site pain | Mild | 1 (3.7%) | 0 (0.0%) | 1 (11.1%) | 0 (0.0%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Infections and infestations | Mild | 7 (25.9%) | 1 (14.3%) | 3 (33.3%) | 3 (27.3%) | 3 (42.9%) |
| | Moderate | 0 (0.0%) | 0 (0.0%) | 0 (0.0%) | 0 (0.0%) | 1 (14.3%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |

TABLE 11-continued

Treatment-Emergent Adverse Events (TEAEs) by System Organ Class, Preferred Term, and Maximum Severity: Part 2 (MAD) Safety Population

| System Organ Class Preferred Term [n (%)] | Maximum Severity [1] | Overall ALT-801 (N = 27) | M1 1.2 mg ALT-801 (N = 7) | M2 1.8 mg ALT-801 (N = 9) | M3 2.4 mg ALT-801 (N = 11) | MAD PLACEDO (N = 7) |
|---|---|---|---|---|---|---|
| Fungal infection | Mild | 1 (3.7%) | 1 (14.3%) | 0 (0.0%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Fungal skin infection | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Oral herpes | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Otitis externa | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Sinusitis | Mild | 0 (0.0%) | 0 (0.0%) | 0 (0.0%) | 0 (0.0%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Tonsillitis | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Upper respiratory tract infection | Mild | 0 (0.0%) | 0 (0.0%) | 0 (0.0%) | 0 (0.0%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Urinary tract infection | Mild | 0 (0.0%) | 0 (0.0%) | 0 (0.0%) | 0 (0.0%) | 1 (14.3%) |
| | Moderate | 0 (0.0%) | 0 (0.0%) | 0 (0.0%) | 0 (0.0%) | 1 (14.3%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Viral upper respiratory tract infection | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Wound infection | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Injury, poisoning and procedural complications | Mild | 1 (3.7%) | 0 (0.0%) | 0 (0.0%) | 1 (9.1%) | 0 (0.0%) |
| | Moderate | 1 (3.7%) | 0 (0.0%) | 1 (11.1%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Post procedural contusion | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Skin abrasion | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Tooth fracture | Mild | 0 (0.0%) | 0 (0.0%) | 0 (0.0%) | 0 (0.0%) | 0 (0.0%) |
| | Moderate | 1 (3.7%) | 0 (0.0%) | 1 (11.1%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Investigations | Mild | 1 (3.7%) | 0 (0.0%) | 1 (11.1%) | 0 (0.0%) | 0 (0.0%) |
| | Moderate | 1 (3.7%) | 0 (0.0%) | 1 (11.1%) | 0 (0.0%) | 1 (14.3%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Blood creatine phosphokinase increased | Mild | 0 (0.0%) | 0 (0.0%) | 0 (0.0%) | 0 (0.0%) | 0 (0.0%) |
| | Moderate | 1 (3.7%) | 0 (0.0%) | 1 (11.1%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Liver function test abnormal | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 1 (14.3%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Metabolism and nutrition disorders | Mild | 8 (29.6%) | 0 (0.0%) | 3 (33.3%) | 5 (45.5%) | 2 (28.6%) |
| | Moderate | 5 (18.5%) | 1 (14.3%) | 2 (22.2%) | 2 (18.2%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |

TABLE 11-continued

Treatment-Emergent Adverse Events (TEAEs) by System Organ Class, Preferred Term, and Maximum Severity: Part 2 (MAD) Safety Population

| System Organ Class Preferred Term [n (%)] | Maximum Severity [1] | Overall ALT-801 (N = 27) | M1 1.2 mg ALT-801 (N = 7) | M2 1.8 mg ALT-801 (N = 9) | M3 2.4 mg ALT-801 (N = 11) | MAD PLACEDO (N = 7) |
|---|---|---|---|---|---|---|
| Decreased appetite | Mild | 9 (33.3%) | 1 (14.3%) | 3 (33.3%) | 5 (45.5%) | 2 (28.6%) |
| | Moderate | 4 (14.8%) | 0 (0.0%) | 2 (22.2%) | 2 (18.2%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Hypoglycaemia | Mild | 2 (7.4%) | 0 (0.0%) | 1 (11.1%) | 1 (9.1%) | 0 (0.0%) |
| | Moderate | 2 (7.4%) | 1 (14.3%) | 1 (11.1%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Polydipsia | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Musculoskeletal and connective tissue disorders | Mild | 2 (7.4%) | 0 (0.0%) | 2 (22.2%) | 0 (0.0%) | 0 (0.0%) |
| | Moderate | 1 (3.7%) | 0 (0.0%) | 0 (0.0%) | 1 (9.1%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Axillary mass | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Back pain | Mild | 0 (0.0%) | 0 (0.0%) | 0 (0.0%) | 0 (0.0%) | 0 (0.0%) |
| | Moderate | 1 (3.7%) | 0 (0.0%) | 0 (0.0%) | 1 (9.1%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Myalgia | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Pain in extremity | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Nervous system disorders | Mild | 11 (40.7%) | 1 (14.3%) | 2 (22.2%) | 8 (72.7%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Dizziness | Mild | 4 (14.8%) | 1 (14.3%) | 1 (11.1%) | 2 (18.2%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Dysgeusia | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Headache | Mild | 8 (29.6%) | 1 (14.3%) | 1 (11.1%) | 6 (54.5%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Hypogeusia | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Somnolence | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Syncope | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Tension headache | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Reproductive system and breast disorders | Mild | 1 (3.7%) | 0 (0.0%) | 1 (11.1%) | 0 (0.0%) | 0 (0.0%) |
| | Moderate | 1 (3.7%) | 0 (0.0%) | 1 (11.1%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Dysmenorrhoea | Mild | 0 (0.0%) | 0 (0.0%) | 0 (0.0%) | 0 (0.0%) | 0 (0.0%) |
| | Moderate | 1 (3.7%) | 0 (0.0%) | 1 (11.1%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |

TABLE 11-continued

Treatment-Emergent Adverse Events (TEAEs) by System Organ Class, Preferred Term, and Maximum Severity: Part 2 (MAD) Safety Population

| System Organ Class Preferred Term [n (%)] | Maximum Severity [1] | Overall ALT-801 (N = 27) | M1 1.2 mg ALT-801 (N = 7) | M2 1.8 mg ALT-801 (N = 9) | M3 2.4 mg ALT-801 (N = 11) | MAD PLACEBO (N = 7) |
|---|---|---|---|---|---|---|
| Menorrhagia | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Respiratory, thoracic and mediastinal disorders | Mild | 2 (7.4%) | 0 (0.0%) | 0 (0.0%) | 2 (18.2%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Cough | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Oropharyngeal pain | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Skin and subcutaneous tissue disorders | Mild | 9 (33.3%) | 2 (28.6%) | 4 (44.4%) | 3 (27.3%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Dermatitis contact | Mild | 4 (14.8%) | 1 (14.3%) | 0 (0.0%) | 3 (27.3%) | 1 (14.3%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Eczema | Mild | 3 (11.1%) | 0 (0.0%) | 3 (33.3%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Papule | Mild | 1 (3.7%) | 1 (14.3%) | 0 (0.0%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Pruritus | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Rash | Mild | 2 (7.4%) | 0 (0.0%) | 2 (22.2%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Skin lesion | Mild | 1 (3.7%) | 0 (0.0%) | 1 (11.1%) | 0 (0.0%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Vascular disorders | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| Hot flush | Mild | 1 (3.7%) | 0 (0.0%) | 0 (0.0%) | 1 (9.1%) | 0 (0.0%) |
| | Moderate | 0 (0.0%) | 0 (0.0%) | 0 (0.0%) | 0 (0.0%) | 0 (0.0%) |
| | Severe | 0 (0.0%) | 0 (0.0%) | 0 (0.0%) | 0 (0.0%) | 0 (0.0%) |
| | PLT | 0 (0.0%) | 0 (0.0%) | 0 (0.0%) | 0 (0.0%) | 0 (0.0%) |
| | Hyperglycemia | | 0 (0%) | 0 (0%) | 0 (0%) | 0 (0%) |

Note:
TEAE = Treatment-Emergent Adverse Event;

Note:
PLT = Potentially Life Threatening

Note:
Adverse Events are coded using MedDRA version MedDRA v23.1 - Sep 2020. For each system organ class and preferred term, subjects are counted only once per system organ class and preferred term.
[1] For maximum severity: Life-threatening > Severe > Moderate > Mild.

TABLE 12

Study disposition (MAD)

| Characteristic | | 1.2 mg | 1.8 mg | 2.4 mg | Pooled placebo |
|---|---|---|---|---|---|
| Safety population[1] | n (%) | 7 (100%) | 9 (100%) | 11 (91.7%) | 7 (100%) |
| Completed study | n (%) | 6 (86%) | 9 (100%) | 9 (82%) | 5 (71%) |
| Early withdrawal | n (%) | 1 (14%) | 0 (0%) | 2 (18%) | 2 (29%) |
| Lost to follow-up | n (%) | 0 (0%) | 0 (0%) | 0 (0%) | 1 (14%) |
| Withdrawal of consent | n (%) | 1 (14%) | 0 (0%) | 2 (18%) | 1 (14%) |
| Due to adverse event | n (%) | 0 (0%) | 0 (0%) | 0 (0%) | 0 (0%) |

[1] Subjects who were randomized, dosed and had one or more post-dose assessments As presented in Table 13, treatment with ALT-801 also tends to show reduced systolic and diastolic blood pressure considered as biomarkers of cardiovascular risk. In addition, treatment with ALT-801 also tends to lower lipids (Table 14) also considered as biomarkers of cardiovascular risk. Moreover, ALT-801 reduces pre-diabetic and metabolic syndromes as shown in Table 15. Treatment with ALT-801 maintains glucose homeostasis indicating that GLP-1 activity of ALT-801 effectively balances the glucagon effects on blood sugar (Table 16). Table 17 shows results of ketone body production indicatives of the impact of ALT-801 on increased fat burn, an effect that can be attributed to the glucagon activity of ALT-801.

TABLE 13

Systolic and Diastolic Blood Pressure - Change from baseline (MAD)

| Characteristic Change from Baseline, Weeks 1-12 [1] | | 1.2 mg | 1.8 mg | 2.4 mg | Pooled placebo |
|---|---|---|---|---|---|
| Systolic Blood Pressure | mm Hg (%) | −10.2 (−8.2%) | −9.2 (−7.8%) | −12.7 (−10.4%) | −5.4 (−4.5%) |
| Diastolic Blood Pressure | mm Hg (%) | −5.2 (−6.7%) | −3.9 (−5.3%) | −7.2 (−9.4%) | −1.7 (−2.3%) |

[1] means of weekly measurements, Weeks 1-12, compared to Baseline

TABLE 14

LDL (Low Density Lipoprotein) and HDL (High Density Lipoprotein)

| Characteristic | | 1.2 mg | 1.8 mg | 2.4 mg | Pooled placebo |
|---|---|---|---|---|---|
| | | Change from Baseline | | | |
| Total cholesterol (mg/dL) | mean (SD) | −41.4 (−20.0%) | −60.6 (−28.05) | −52.7 (−28.0%) | −17.1 (−9.1%) |
| HDL cholesterol (mg/dL) | mean (SD) | −7.1 (−16.7%) | −14.2 (−30.25) | −15.9 (−36.0%) | −10.3 (−19.2%) |
| LDL cholesterol (mg/dL) | mean (SD) | −24.7 (−16.9%) | −37.4 (−30.35) | −29.4 (−26.7%) | −4.8 (−4.3%) |
| Triglycerides (mg/dL) | mean (SD) | −59.0 (−37.0%) | −43.3 (−37.95) | −33.0 (−29.3%) | −9.8 (−8.2%) |

TABLE 15

Pre-diabetic and metabolic syndrome

| | | Treatment [1] | | | |
|---|---|---|---|---|---|
| Characteristic | | 1.2 mg | 1.8 mg | 2.4 mg | Pooled placebo |
| Pre-diabetes | | | | | |
| Baseline | n (%) | 3 (50.0%) | 5 (55.6%) | 7 (77.8%) | 2 (40.0%) |
| Week 12 | n (%) | 0 (0.0%) | 3 (33.3%) | 1 (11.1%) | 0 (0.0%) |
| Metabolic syndrome | | | | | |
| Baseline | n (%) | 3 (50.0%) | 4 (44.4%) | 5 (55.6%) | 2 (40.0%) |
| Week 12 | n (%) | 3 (50.0%) | 2 (22.2%) | 6 (66.7%) | 2 (40.0%) |

[1] Analysis includes only subjects with non-missing data at Days 1 and 84

TABLE 16

Fasting Plasma Glucose and Hemoglobin A1c (HbA1c %)

| | | Treatment | | | |
|---|---|---|---|---|---|
| Characteristic | | 1.2 mg | 1.8 mg | 2.4 mg | Pooled placebo |
| Fasting Plasma Glucose [1] | | | | | |
| Change from Baseline | mg/dL (%) | +3.0 (+3.5%) | −0.4 (−0.5%) | −0.8 (−0.9%) | −0.2 (−0.2%) |
| HbA1c (%) | | | | | |
| Baseline | Mean (SD) | 5.3 (0.1) | 5.5 (0.2) | 5.3 (0.2) | 5.3 (0.2) |
| Week 12 | Mean (SD) | 5.4 (0.2) | 5.4 (0.3) | 5.3 (0.3) | 5.3 (0.3) |
| HOMA-IR (insulin resistance) | | | | | |
| Baseline | Mean (SD) | 2.5 (1.2) | 2.4 (2.5) | 3.1 (1.8) | 2.4 (1.7) |
| Week 12 | Mean (SD) | 2.0 (1.4) | 2.2 (2.5) | 2.4 (1.2) | 2.4 (1.2) |

[1] mean of weekly measurements, Weeks 1-12, compared to Baseline

TABLE 17

Ketone body production

| | | Treatment | | | |
|---|---|---|---|---|---|
| Characteristic | | | | | Pooled |
| Ketone bodies | | 1.2 mg | 1.8 mg | 2.4 mg | placebo |
| Baseline (mmol/L) | mean (SD) | 2.2 (0.9) | 1.3 (0.7) | 1.8 (0.6) | 1.3 (0.4) |
| Week 12 (mmol/L) | mean (SD) | 6.1 (10.2) | 9.3 (11.1) | 7.5 (3.8) | 3.6 (3.6) |

ALT-801 also presents a favorable pharmaco-kinetic (PK) profile that supports weekly dosing and that may be associated with acceptable gastrointestinal tolerability as shown in Table 18.

TABLE 18

Pharmaco-kinetic (PK) parameters of ALT-801

| PK PARAMETER | ALT-801 1.8 mg SC |
|---|---|
| Peak concentration ($C_{max}$) | 27.1 nmol/L |
| Area under the curve ($AUC$)$_{0-168}$ | 3400 nmol · hr |
| Half-life ($t_{1/2}$) | 110 hrs |
| Time to peak concentration ($T_{max}$) | 70 hrs |

In summary, impressive 10.3% weight loss was observed in this study after only 12-week treatment with ALT-801 at 1.8 mg subcutaneous dose. This effect was maintained at the 2.4 mg dose. A majority (55%) of subjects at 1.8 mg dose realized greater than 10% weight loss. Weight loss trends were maintained through Week 12. ALT-801 was well-tolerated, with predominantly mild adverse events. The treatment led to no study discontinuations due to adverse events. Linear rate of weight loss suggest these effects will be sustained. Compared to other GLP-1-receptor biased agonist like Semaglutide, no dose titration is required to achieve rapid weight loss with good patient compliance. In addition, no hyperglycemic AEs, and no adverse effects on blood glucose control or heart rate were observed.

Example 6: Phase 1, Randomized, Double-Blind, Placebo-Controlled, Parallel Group Study to Evaluate the Safety and Tolerability, Pharmacodynamics and Pharmacokinetics of ALT-801 in Overweight and Obese Subjects with Type 2 Diabetes Mellitus This is a Phase 1, randomized, double-blind, placebo-controlled, parallel group study to evaluate the safety and tolerability, pharmacodynamic (PD) and pharmacokinetic (PK) of ALT-801 and its effects on glucose control in overweight and obese (18- to 65-year old male or non-pregnant female subjects having a body mass index (BMI) of 28.0-40.0 kg/m$^2$) subjects with T2DM that, for at least three months prior to screening, any combination of (1) diet and exercise, (2) metformin with absent or mild gastrointestinal symptoms (nausea, vomiting, or diarrhea), and/or (3) sodium glucose cotransporter (SGLT-2) therapy. In this study, ALT-801 or placebo is administered by subcutaneous (SC) injection (preferably in the abdomen) once weekly for up to 12 doses to patients with type 2 diabetes mellitus (T2DM) (e.g., 48 subjects) for approximately 4.5 months including up to a 35-day screening period, an 85-day treatment period, and a 25-day follow-up period.

The primary safety objective is to assess the safety and tolerability of ALT-801 in T2DM subjects and the secondary safety objective is to assess the effect of ALT-801 on glycemic parameters and incidences of hyperglycemia and hypoglycemia in T2DM subjects. Primary safety endpoints include adverse events (AEs), vital signs, rate-pressure product (mean heart rate×mean systolic blood pressure), liver function tests, incidence of hyperglycemic and hypoglycemic adverse events, physical examinations, injection site reactions, and immunogenicity. Secondary safety endpoints include change from baseline glycemic parameters including fasting serum glucose, CGM parameters (area under the glucose concentration-time profile, time in range and hyperglycemia and hypoglycemia), and HbA1c. Continuous safety data will be summarized with descriptive statistics (arithmetic mean, standard deviation [SD], median, minimum, and maximum) by dose level and treatment (active or placebo). Categorical safety data will be summarized with frequency counts and percentages by dose level, treatment group, and day where applicable. AEs will be coded using the most current Medical Dictionary for Regulatory Activities (MedDRA) version. A by-subject AE data listing, including verbatim term, preferred term, system organ class (SOC), treatment, severity, and relationship to study medication, will be provided. The number of subjects experiencing treatment-emergent AEs (TEAEs) and number of individual TEAEs and injection site reactions will be summarized by treatment group, SOC and preferred term. TEAEs will also be summarized by severity and by relationship to study medication. Laboratory evaluations, including liver function tests and fasting serum glucose, vital signs (including calculation of RPP), and ECG assessments will be summarized by treatment group, dose levels, and protocol specified collection time point. A summary of change from baseline at each protocol specified time point by treatment group will also be presented. Changes in physical examinations will be listed for each subject. Concomitant medications will be listed by subject and coded using the most current version of the World Health Organization (WHO) drug dictionary. Medical history will be coded using the most current MedDRA version and will be listed by subject.

The primary pharmacodynamic (PD) objective is to assess the effect of ALT-801 on insulin sensitivity and secretion in T2DM subjects. These include changes from baseline insulin secretion and sensitivity as measured by MMTT (area under the curve over four hours (AUC0-4) of serum glucose, C-peptide and insulin) and the Homeostasis Model Assessment for Insulin Resistance (HOMA IR) (fasting plasma glucose and insulin). The secondary PD objectives are to assess the effect of ALT-801 on gastric emptying (lag phase, half-time, gastric emptying coefficient) as measured by the $^{13}$C-spirulina breath test, anthropometric parameters (e.g., body weight, waist circumference, BMI), lipid metabolism (cholesterol (total, low density lipoprotein (LDL), high density lipoprotein (HDL), apolipoprotein (Apo) A and B, lipoprotein(a), and triglycerides (TG)), metabolic markers (leptin, adiponectin), inflammatory markers (tumor necrosis factor (TNF), high-sensitivity C-reactive protein (hs-CRP), plasminogen activator inhibitor-1 (PAI-1), monocyte chemoattractant protein-1 (MCP-1), and interleukin-6 (IL-6)), and lipotoxicity markers in T2DM subjects. Changes in insulin sensitivity and secretion, anthropometric parameters, lipid metabolism, metabolic markers, lipotoxicity markers, and inflammation markers will be listed and summarized by treatment group with descriptive statistics (sample size (N), arithmetic mean, SD, median, minimum, maximum, geometric mean, and geometric coefficient of variation (CV %)). The effects of baseline BMI on PD parameters will be evaluated by covariate analyses. Change from baseline lag phase, half-time, gastric emptying coefficient data will be listed and summarized with descriptive statistics (N, arithmetic mean, SD, CV %, median, minimum, and maximum).

Quality of life (QoL) effects are also monitored (changes in Short Form-36 and Impact of Weight on Quality of Life-Lite Clinical Trials version (IWQoL-Lite for CT) compared to baseline). Changes from baseline in the two summary scores for physical health and mental health, and eight domain scores for SF-36 and the composite score for the IWQoL-Lite for CT will be listed and summarized by treatment group with descriptive statistics (N, arithmetic mean, SD, median, minimum, maximum, geometric mean, and geometric CV %). Inferential statistics applicable to continuous endpoints will be applied, as described above.

The pharmacokinetic (PK) objective is to assess ALT-801 concentrations and change from baseline metformin concentration. Individual ALT-801 and metformin concentration data will be listed and summarized by treatment group and timepoint with descriptive statistics (N, arithmetic mean, SD, CV %, median, minimum, and maximum). Individual and mean±SD ALT-801 concentration-time profiles for each cohort will also be presented graphically. Change from baseline metformin concentrations be listed and summarized by treatment group and timepoint with descriptive statistics (N, arithmetic mean, SD, CV %, median, minimum, and maximum). A population PK model will be developed to enable the prediction of individual subject ALT-801 plasma concentration time curves and related PK parameters. Covariates, including sex, age, body weight, BMI, and concomitant medications will be explored wherever possible and exposure response relationships will be explored for efficacy and safety endpoints where possible.

After providing informed consent, subjects will undergo a screening period of up to 35 days. Subjects will be instructed how to maintain their normal diets, alcohol consumption and physical activities and not to start any new diets, supplements, or exercise programs at any time while participating in the study. Counseling will be provided on diet and exercise starting on the Day −8 visit and will be reinforced at each visit during the treatment period. Subjects who meet inclusion and do not meet exclusion criteria will be randomized 1:1:1:1 to one of the following treatment arms: ALT-801 1.2 mg subcutaneous (SC) once weekly for 12 weeks; ALT-801 1.8 mg SC once weekly for 12 weeks; ALT-801 0.6 mg SC at week 1, 1.2 mg SC at week 2, 1.8 mg SC once weekly for 2 weeks (weeks 3 and 4), and 2.4 mg SC once weekly for weeks 5 through 12; and, placebo (0.9% NaCl) SC once weekly for 12 weeks. Subjects will be stratified by presence or absence of metformin use at baseline. There will be 12 subjects in each treatment arm. Subjects will receive the first dose of study medication on Day 1. Subsequent visits will be conducted weekly at the clinic, home or work through Day 85 or early termination Table 1. Subjects will return for a safety follow-up visit on Day 110. Investigators will follow the decision criteria for the timing and method of intervention in subjects who develop worsening abnormal liver function tests during the 12-week treatment period. Subjects will undergo 7 days of continuous glucose monitoring (CGM) to measure blood glucose at screening, during Week 5, and during the final week of the study. A mixed meal tolerance test (MMTT) with measurements of glucose and hormonal markers will be performed at screening and at the end of the treatment period. Subjects will also undergo $^{13}$C-spirulina gastric emptying breath test during screening (Day −8) and at Week 8 (Day 50) to assess the effect of ALT-801 on gastric emptying rate. Fasting glucose levels will be measured by a glucometer and documented by study staff starting on Day −35 and at every visit during the treatment period. On non-visit days, subjects will also monitor and record fasting glucose each morning and will contact the study site for a reading >240 mg/dL or <70 mg/dL. During the weeks when CGM is performed (screening, Week 4, and Week 12), any CGM readings <70 mg/dL will be confirmed by a glucometer reading. Subjects will also be educated on symptoms and treatment of hypoglycemia and will obtain a glucometer reading if they experience blood glucose <70 mg/mL or symptoms suggestive of hypoglycemia. Subjects will record any symptoms of hypoglycemia experienced at home in a log along with a glucometer reading at the time of the event, which will be reviewed by the Investigator at each visit. Investigators will counsel subjects on how to keep their fasting glucose within the limits, including repeated diet counseling, and will follow the decision criteria for the timing and method of intervention in subjects with persistent hyperglycemia during the 12-week treatment period. If a significant decrease of fasting glucose is repeatedly observed (<50 mg/dL) or a subject requires interventions or external assistance to treat hypoglycemia, the subject may be dropped from the study and replaced. Sparse blood samples will be collected for ALT-801 PK to be combined with data from other studies in population PK and PK-PD modeling and for metformin PK to assess the change in metformin concentrations over time in the presence of ALT-801. Blood samples will also be collected to assess immunogenicity.

The results of this trial will show that ALT-801 administered by subcutaneous (SC) injection once weekly for up to 12 doses in subjects with T2DM is safe and tolerable, has positive PD, quality of life, and PK effects as well as glucose control in the subjects.

Example 7: Phase 1, 12-Week, Randomized, Double-Blind, Placebo-Controlled Study of ALT-801 in Diabetic and Non-Diabetic Overweight and Obese Subjects with Non-Alcoholic Fatty Liver Disease ALT-801 is a modified 29-amino peptide with equipotent dual agonist properties for the glucagon-like peptide 1 receptor (GLP-1R) and glucagon receptor (GCGR). ALT-801 is being developed for non-alcoholic steatohepatitis (NASH), a subgroup of non-alcoholic fatty liver disease (NAFLD) where steatosis leads to hepatocyte injury and inflammation (steatohepatitis), with or without fibrosis. In the United States (US), NASH has become the leading cause of end-stage liver disease or liver transplantation [Goldberg 2017]. Obesity is the core driver of NASH and weight loss results in reduction in liver fat and NASH improvement [Vilar-Gomez 2015]. More than 80% of individuals with NASH are overweight or obese [Diehl 2017], and with no currently available US Food and Drug Administration (FDA) approved pharmacologic options for inducing weight loss, therapy has largely been based on lifestyle interventions directed at achieving weight loss. However, it is difficult to attain and maintain long-term weight loss with lifestyle changes alone. Glucagon-like peptide-1 receptor agonists (GLP-1RA) have emerged as a treatment option for patients with NASH. Liraglutide, a daily GLP-1RA, was associated with resolution of NASH, with a trend towards improvement of liver fibrosis [Armstrong 2016]. In a recent trial, semaglutide doses up to 0.4 mg/day were associated with a mean weight loss of up to 12.5% along with significantly higher rates of NASH resolution. Ten percent or greater weight loss has been considered the cutoff optimal NASH resolution and improvement of fibrosis [Vilar-Gomez 2015]. Higher levels of weight loss have also been associated with lower incidences of cardiovascular disease and non-hepatic malignancies, which represent the most serious comorbidities facing NASH patients. Unfortunately, the doses of liraglutide and semaglutide employed in these studies were associated with high rates of gastrointestinal (GI) AEs that could lead to patient discomfort and non-compliance. GLP-1RAs exert central effects on appetite and food intake, while GCGR agonists (GCGRAs) drive increased energy expenditure in animal models and humans [Lynch 2104]. The effects of GCGRAs and GLP-1RAs have been shown to be synergistic in driving greater degrees of weight loss compared to a GLP-1RAs alone [Day 2012]. GCGRAs also enhance lipolysis and suppress liver fat synthesis, providing an additional pathway for liver fat reduction and NASH resolution [Schade 1979]. Dual agonists combine GCGRA with GLP-1RA in the same molecule. In obese non-human primates, chronic administration of a GLP-1RA/GCGRA dual agonist reduced body weight and improved glucose tolerance to a greater degree compared to a GLP-1RA mono-agonist [Tschop 2016]. Clinical studies of cotadutide, a GLP-1/GCGR dual agonist with a 5:1 bias of GLP-1 to glucagon activity, demonstrated an impressive 39% reduction in hepatic fat fraction in just 6 weeks and greater improvement in NASH-related alanine aminotransferase (ALT) reduction than liraglutide alone. However, the degree of weight loss over 26 weeks of cotadutide administration was not significantly greater than liraglutide (5.4% vs. 5.5%), suggesting that the 5:1 ratio was acceptable for liver fat reduction but suboptimal for weight reduction [Alba 2021, Ambery 2018, Nahra 2021, Armstrong 2016]. Balanced (1:1) agonism has been shown to be associated with greater weight loss and metabolic effects than biased ratios that favor one agonist over the other [Day 2012]. A recent study with JNJ 64565111 [Alba 2021], a balanced dual agonist, achieved impressive reductions in body weight in just 12 weeks (NCT03586830). Evidence suggests that GLP-1RA/GCGRA dual agonists may also exert positive effects on glycemic control [Nahra 2021]. GLP-1R and GLP-1 based dual receptor agonists with bias towards GLP-1 have been commonly associated with GI adverse effects, including nausea, vomiting and diarrhea [Filippatos 2014]. These agents must also be titrated over prolonged periods to reduce side effects [Ambery 2018, Newsome 2020, Frias 2018], and agents with improved tolerability and dosing regimens are needed. Because both GLP-1R and GCGR agonism contribute to weight loss, less aggressive dosing is anticipated with unimolecular GLP-1R/GCGR dual agonists, providing for the possibility of lower rates of GI toxicity.

This example describes a Phase 1, randomized, double-blind, placebo-controlled, parallel group study to assess the safety of ALT-801 and its effects on hepatic fat fraction, anthropometric parameters, lipid metabolism, inflammatory markers and fibrosis markers in diabetic and non-diabetic overweight and obese (body mass index [BMI] 28.0-40.0 kg/m$^2$) subjects with Non-alcoholic Fatty Liver Disease (NAFLD). This study is designed to assess changes in hepatic fat fraction by MRI-PDFF in diabetic and non-diabetic overweight and obese subjects with NAFLD after 12 weeks of ALT-801 treatment. The study will also assess changes in body weight, lipid metabolism, metabolic markers, and inflammatory markers and safety and tolerability of ALT-801 after 12 weeks of treatment. Subjects will be stratified for the presence of absence of diabetes at baseline. This study is designed to assess changes in hepatic fat fraction by MRI-PDFF in diabetic and non-diabetic overweight and obese subjects with NAFLD after 12 weeks of ALT-801 treatment. The study will also assess changes in body weight, lipid metabolism, metabolic markers, and inflammatory markers and safety and tolerability of ALT-801 after 12 weeks of treatment. Subjects will be stratified for the presence of absence of diabetes at baseline.

For this study, suitable subjects are those with NAFLD without significant fibrosis, defined as FibroScan® controlled attenuation parameter (CAP)≥280 dB/m and liver stiffness measurement (LSM)<8.5 kPa, and magnetic resonance imaging derived proton density fat fraction (MRI-PDFF)≥10%. If a subject has Type 2 diabetes mellitus (T2DM), on stable regimen, for at least 3 months prior to screening, of any combination of (1) diet and exercise, (2) metformin with absent or mild gastrointestinal symptoms (nausea, vomiting or diarrhea), and/or (3) sodium glucose cotransporter-2 (SGLT-2) therapy. After providing informed consent, subjects will undergo a screening period of up to 35 days. Subjects will be instructed how to maintain their normal diets, alcohol consumption and physical activities and not to start any new diets, supplements, or exercise programs at any time while participating in the study. Counseling will be provided on diet and exercise on the Day 1 visit and will be reinforced at subsequent visits. Subjects who meet inclusion and do not meet exclusion criteria will be randomized 1:1:1:1 to one of the following treatment arms: 1) ALT-801 1.2 mg SC once weekly for 12 weeks; 2) ALT-801 1.8 mg SC once weekly for 12 weeks; 3) ALT-801 0.6 mg SC at week 1, 1.2 mg SC at week 2, 1.8 mg SC once weekly for 2 weeks (weeks 3 and 4), and 2.4 mg SC once weekly for weeks 5 through 12; or, Placebo (0.9% NaCl) subcutaneously (SC) once weekly for 12 weeks. Subjects will be stratified by presence or absence of diabetes at baseline. There will be 18 subjects in each treatment arm. Subjects will receive the first dose of study medication on Day 1. Subsequent visits will be conducted weekly, at the clinic, home or work, through Day 85 or early termination. Subjects will return for a safety follow-up visit on Day 110. Investigators will follow the decision criteria for the timing and method of intervention in subjects who develop worsening abnormal liver function tests during the 12-week treatment period. Fasting plasma glucose (FPG) levels will be measured by a glucometer and documented by study staff at baseline and prior to each dose. On non-visit days, subjects will also monitor and record FPG each morning and will contact the study site for a reading >240 mg/dL or <70 mg/dL. Subjects will also be educated on symptoms and treatment of hypoglycemia and will obtain a glucometer reading if they experience plasma glucose <70 mg/mL or symptoms suggestive of hypoglycemia. Subjects will record any symptoms of hypoglycemia experienced at home in a log, which will be reviewed by the Investigator at each visit commencing with Day 8. Investigators will counsel subjects on how to keep their FPG within the limits, including repeated diet counseling, and will follow the decision criteria for the timing and method of intervention in subjects with persistent hyperglycemia during the 12-week treatment period. If a significant decrease of FPG is repeatedly observed (FPG<50 mg/dL) or a subject requires interventions or external assistance to treat hypoglycemia, the subject may be dropped from the study and replaced. Sparse blood samples will be collected for ALT-801 pharmacokinetics (PK) to be combined with data from other studies in population PK and PK-PD (pharmacodynamic) modeling and for metformin PK to assess the change in metformin concentrations over time in the presence of ALT-801. Blood samples will also be collected to assess immunogenicity.

Safety endpoints include adverse events (AEs), Vital signs and Rate-Pressure Product (RPP calculated as mean heart rate×mean systolic blood pressure), safety labs, including liver function tests and serum glucose, urinalysis, physical examination, injection site reactions, and immunogenicity (neutralizing antibodies). Pharmacodynamic (PD) endpoints include changes in hepatic fat fraction by MRI-PDFF compared to baseline (relative and absolute % change, proportion of subjects achieving 30%, 40% and 50% relative reductions in hepatic fat fraction, proportions of subjects with normalization of liver fat), changes compared to baseline in anthropometric parameters (body weight, waist circumference, and body composition by MRI scanning), lipid metabolism (total cholesterol (TC), low density lipoprotein cholesterol (LDL-C), high-density lipoprotein cholesterol (HDL-C), apolipoprotein A (Apo A) and B (Apo B), lipoprotein(a), triglycerides (TG)), metabolic markers (hemoglobin A1c (HbA1c), adiponectin, leptin), inflammatory markers (TNF, high-sensitivity C-reactive protein (hs-CRP), monocyte chemoattractant protein-1 (MCP-1), interleukin-6 (IL-6), plasminogen activator inhibitor (PAI-1)), fibrosis markers (N-terminal type III collagen pro-peptide (Pro-C3), enhanced liver fibrosis (ELF) test), lipotoxicity markers, quality of life endpoint, and pharmacokinetic (PK) endpoints. Based on treatment effects observed in prior studies of NAFLD, this study has adequate power to detect meaningful differences in the change in hepatic fat fraction by MRI-PDFF compared to baseline in the subjects with ALT-801 compared to subjects who received placebo SC injection at a 0.05 level of significance (2-sided). All randomized subjects who received at least one dose of study medication (Safety Population) will be included in the safety analyses.

The safety objective is to assess the safety and tolerability of ALT-801 in subjects with NAFLD. Primary safety endpoints include adverse events (AEs), vital signs, rate-pressure product (mean heart rate×mean systolic blood pressure), liver function tests, incidence of hyperglycemic and hypoglycemic adverse events, physical examinations, injection site reactions, and immunogenicity. Secondary safety endpoints include change from baseline glycemic parameters including fasting serum glucose, CGM parameters (area under the glucose concentration-time profile, time in range and hyperglycemia and hypoglycemia), and HbA1c. Continuous safety data will be summarized with descriptive statistics (arithmetic mean, standard deviation [SD], median, minimum, and maximum) by dose level and treatment (active or placebo). Categorical safety data will be summarized with frequency counts and percentages by dose level, treatment group, and day where applicable. AEs will be coded using the most current Medical Dictionary for Regulatory Activities (MedDRA) version. A by-subject AE data listing, including verbatim term, preferred term, system organ class (SOC), treatment, severity, and relationship to study medication, will be provided. The number of subjects experiencing treatment-emergent AEs (TEAEs) and number of individual TEAEs and injection site reactions will be summarized by treatment group, SOC and preferred term. TEAEs will also be summarized by severity and by relationship to study medication. Laboratory evaluations, including liver function tests and fasting serum glucose, vital signs (including calculation of RPP), and ECG assessments will be summarized by treatment group, dose levels, and protocol specified collection time point. A summary of change from baseline at each protocol specified time point by treatment group will also be presented. Changes in physical examinations will be listed for each subject. Concomitant medications will be listed by subject and coded using the most current version of the World Health Organization (WHO) drug dictionary. Medical history will be coded using the most current MedDRA version and will be listed by subject.

The pharmacodynamic (PD) objectives are to assess is to assess the effect of ALT-801 on hepatic fat fraction, anthropometric parameters (e.g., body weight, waist circumference, BMI), lipid metabolism (e.g., cholesterol (total, low density lipoprotein (LDL-C), high density lipoprotein (HDL-C), apolipoprotein (Apo) A and B, lipoprotein(a), and triglycerides (TG)), metabolic markers (e.g., leptin, hemoglobin A1c (HbA1c), adiponectin), inflammatory markers (e.g., tumor necrosis factor (TNF), high-sensitivity C-reactive protein (hs-CRP), plasminogen activator inhibitor-1 (PAI-1), monocyte chemoattractant protein-1 (MCP-1), interleukin-6 (IL-6), and plasminogen activator inhibitor-1 (PAI-1)), fibrosis markers (e.g., N-terminal type III collagen propeptide (Pro-C3), enhanced liver fibrosis (ELF) test), and lipotoxicity markers in the NASH subjects. Changes in insulin sensitivity and secretion, anthropometric parameters, lipid metabolism, metabolic markers, lipotoxicity markers, and inflammation markers will be listed and summarized by treatment group with descriptive statistics (sample size (N), arithmetic mean, SD, median, minimum, maximum, geometric mean, and geometric coefficient of variation (CV %)). The effects of baseline BMI on PD parameters will be evaluated by covariate analyses.

Quality of life (QoL) effects are also monitored (changes in Short Form-36 and Impact of Weight on Quality of Life-Lite Clinical Trials version (IWQoL-Lite for CT) compared to baseline). Changes from baseline in the two summary scores for physical health and mental health, and eight domain scores for SF-36 and the composite score for the IWQoL-Lite for CT will be listed and summarized by treatment group with descriptive statistics (N, arithmetic mean, SD, median, minimum, maximum, geometric mean, and geometric CV %). Inferential statistics applicable to continuous endpoints will be applied, as described above.

The pharmacokinetic (PK) objective is to assess ALT-801 concentrations and change from baseline metformin concentration. Individual ALT-801 and metformin concentration data will be listed and summarized by treatment group and timepoint with descriptive statistics (N, arithmetic mean, SD, CV %, median, minimum, and maximum). Individual and mean±SD ALT-801 concentration-time profiles for each cohort will also be presented graphically. Change from baseline metformin concentrations be listed and summarized by treatment group and timepoint with descriptive statistics (N, arithmetic mean, SD, CV %, median, minimum, and maximum). A population PK model will be developed to enable the prediction of individual subject ALT-801 plasma concentration time curves and related PK parameters. Covariates, including sex, age, body weight, BMI, and concomitant medications will be explored wherever possible and exposure response relationships will be explored for efficacy and safety endpoints where possible.

The results of this trial will show that ALT-801 administered by subcutaneous (SC) injection once weekly for up to 12 doses in subjects with NASH is safe and tolerable, has positive PD, quality of life, and PK effects, as well as glucose control in the subjects.

Example 8: Reduction of Liver Fat by Treatment with ALT-801

Figure 6:
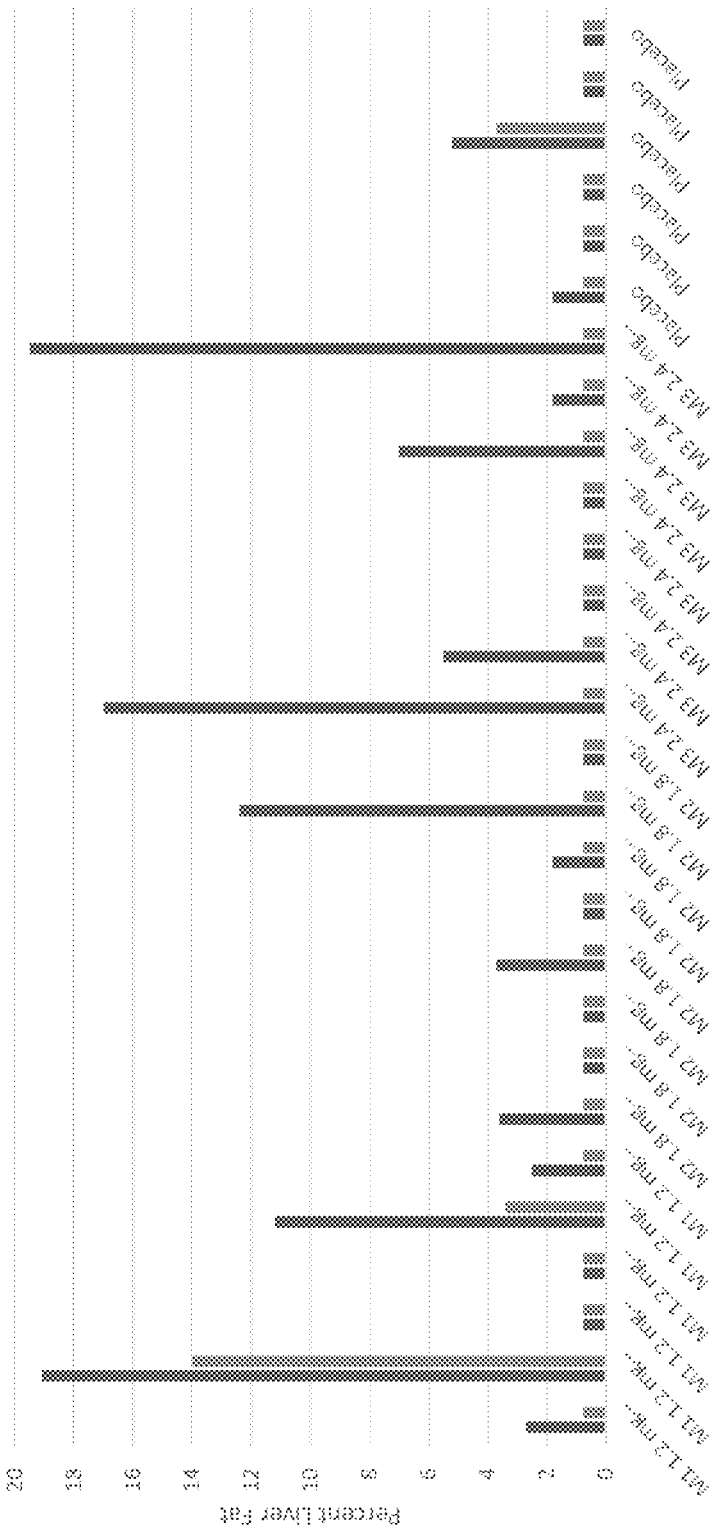
FIG. 6 illustrates pre- vs. post-treatment (ALT-801 at 1.2, 1.8, or 2.4 mg) liver fat levels in all measurable subjects, wherein the first bar is the measurement at screening (baseline) and the second is the measurement at week 6.
Figure 7:
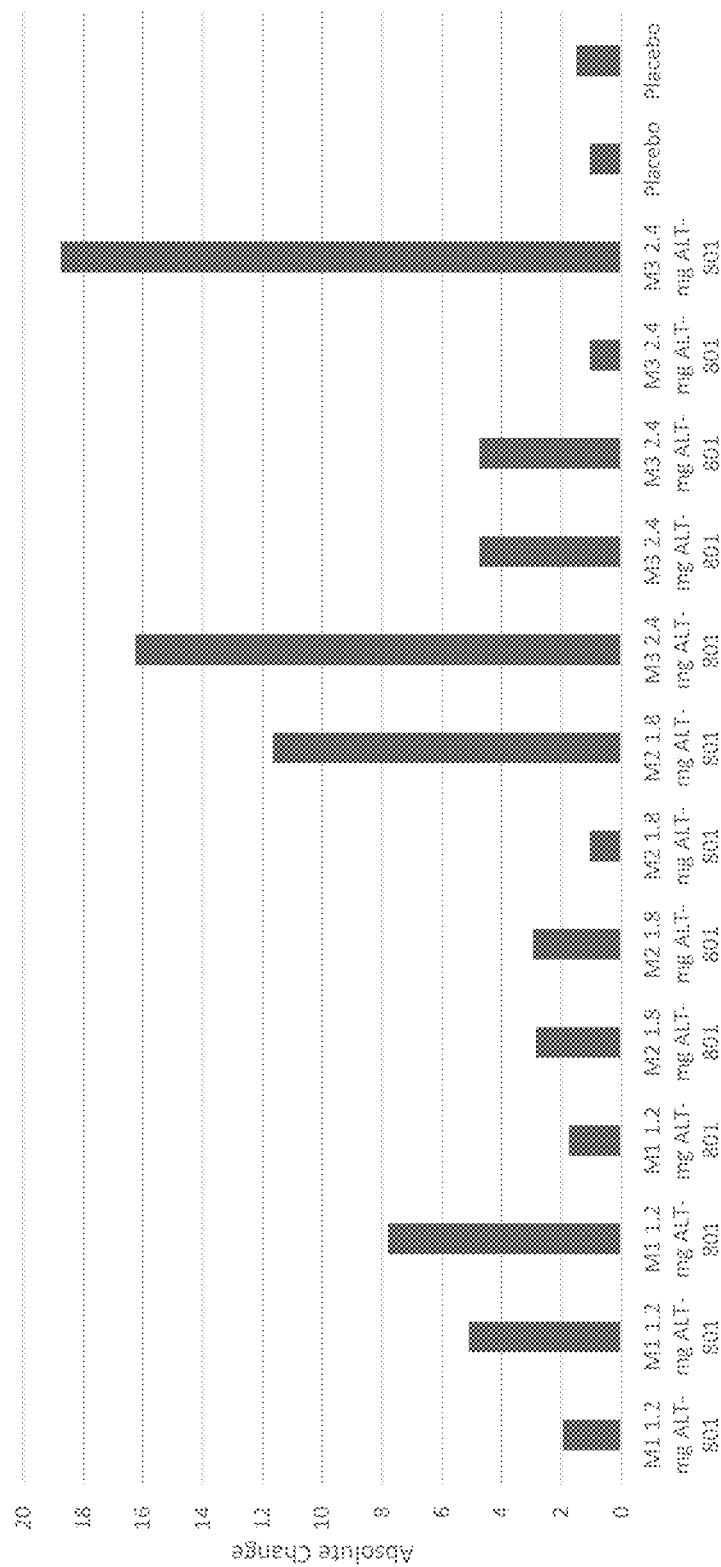
FIG. 7 illustrates the absolute change in liver fat levels at six weeks post-treatment with ALT-801 (1.2, 1.8 or 2.4 mg treatments) in all measurable subjects as compared to placebo.
Figure 8:
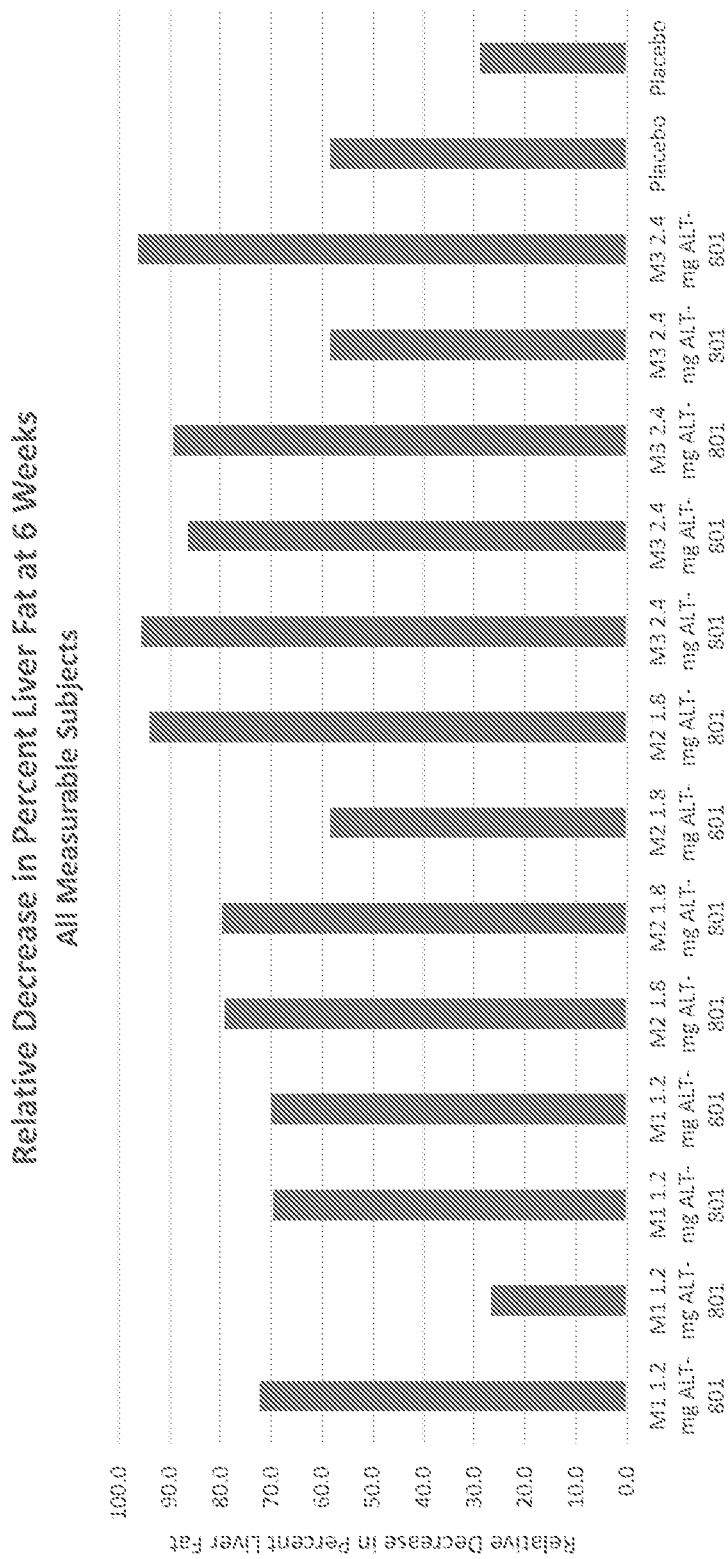
FIG. 8 illustrates the relative change in liver fat levels at six weeks post-treatment with ALT-801 (1.2, 1.8 or 2.4 mg treatments) in all measurable subjects as compared to placebo.
Figure 9:
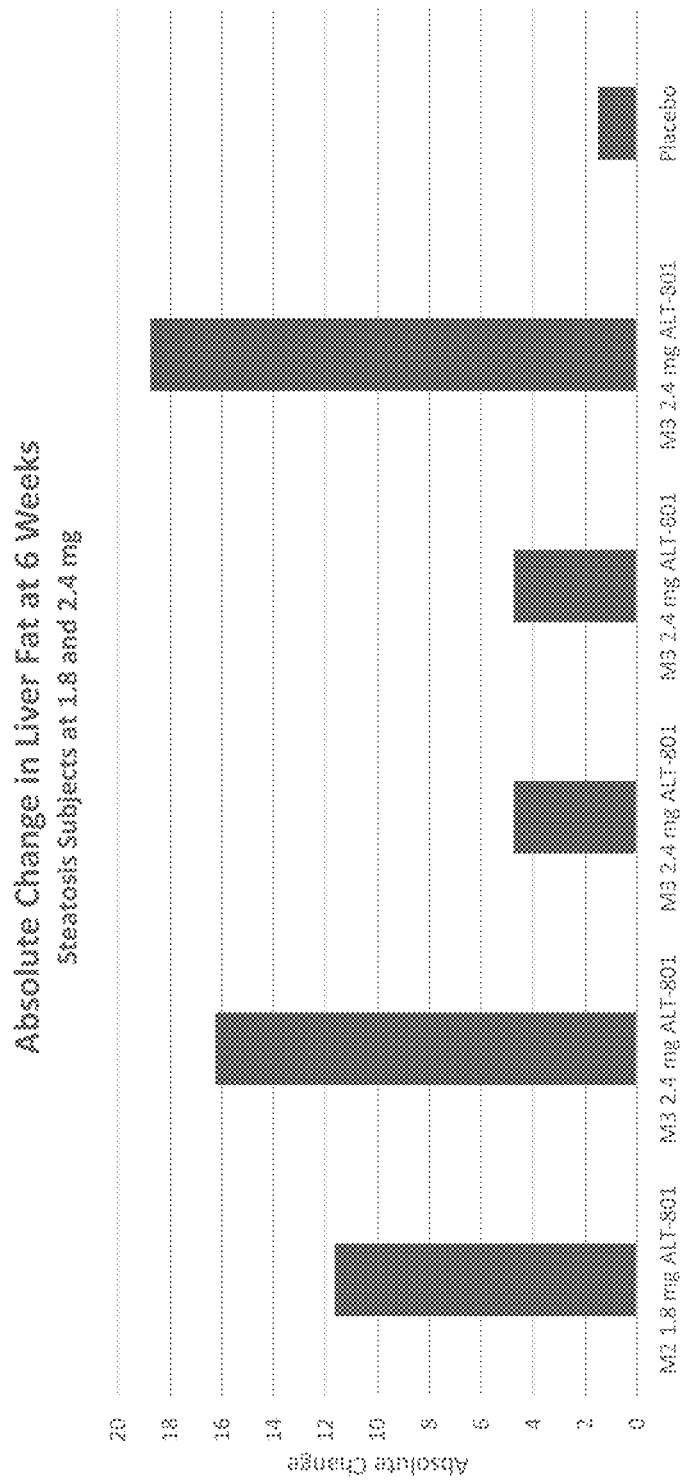
FIG. 9 illustrates the absolute change in liver fat levels at six weeks post-treatment with ALT-801 (1.8 or 2.4 mg treatments) in all steatosis subjects as compared to placebo.
Figure 10:
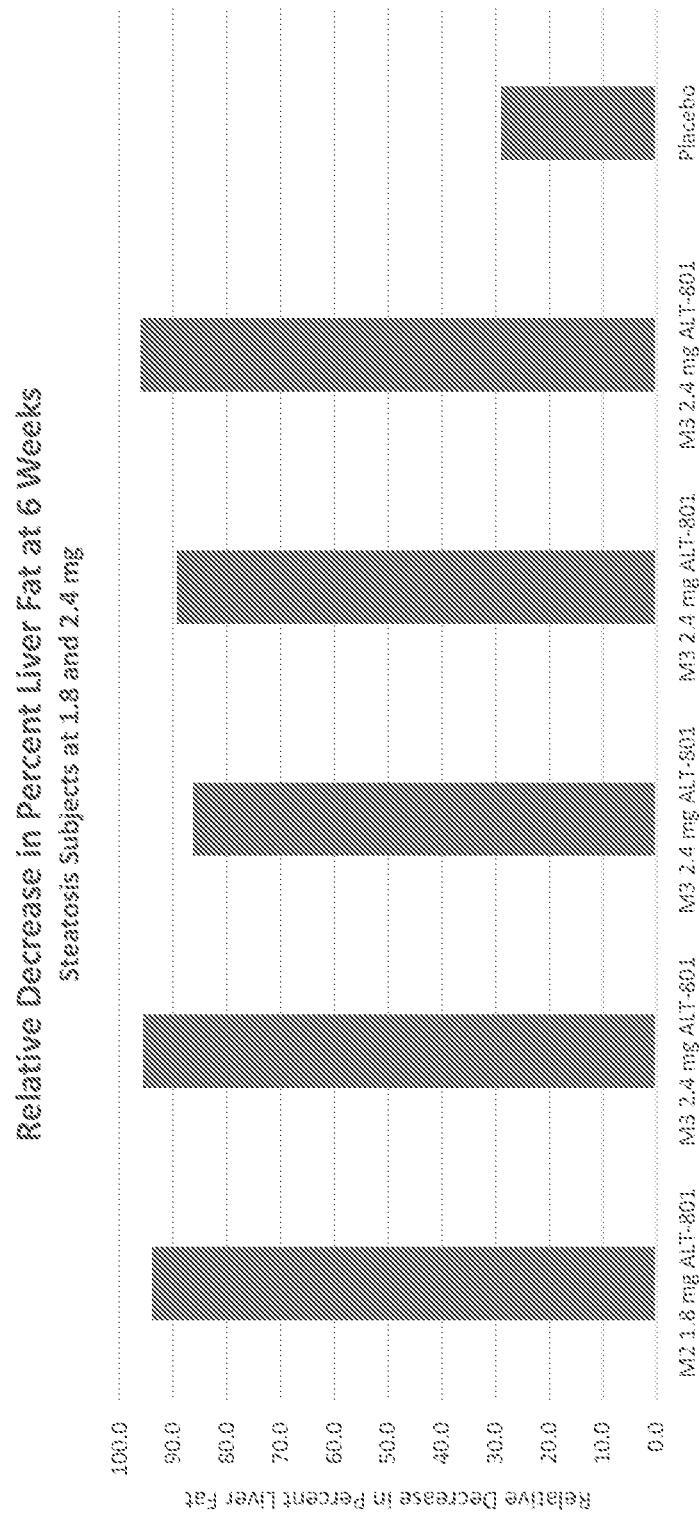
FIG. 10 illustrates the relative change in liver fat levels at six weeks post-treatment with ALT-801 (1.8 or 2.4 mg treatments) in all steatosis subjects as compared to placebo.
Figure 11:
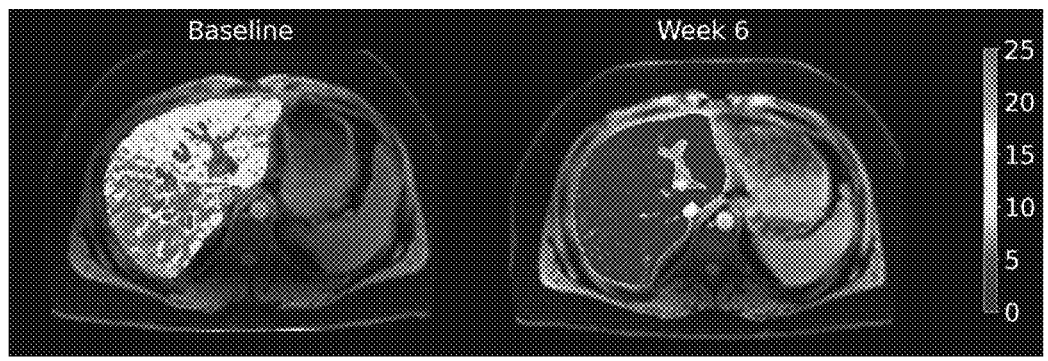
FIG. 11 shows greater than 90% reduction in liver fat to undetectable levels by MRI-PDFF (Magnetic Resonance Imaging Proton Density Fat Fraction) following six week treatment with ALT-801 (1.8 and 2.4 mg doses), wherein each subject had a baseline liver fat content of 19.5%, 17% and 12.5%, respectively. Weekly treatment with a dose of 1.8 mg or 2.4 mg of ALT-801 decreased the liver fat content (LFC) to undetectable levels (below the LOD (limit of detection).
Figure 11:
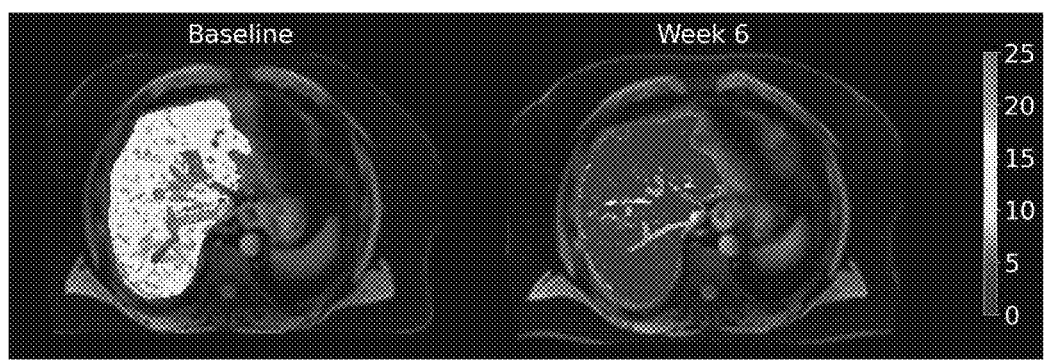
Figure 11:
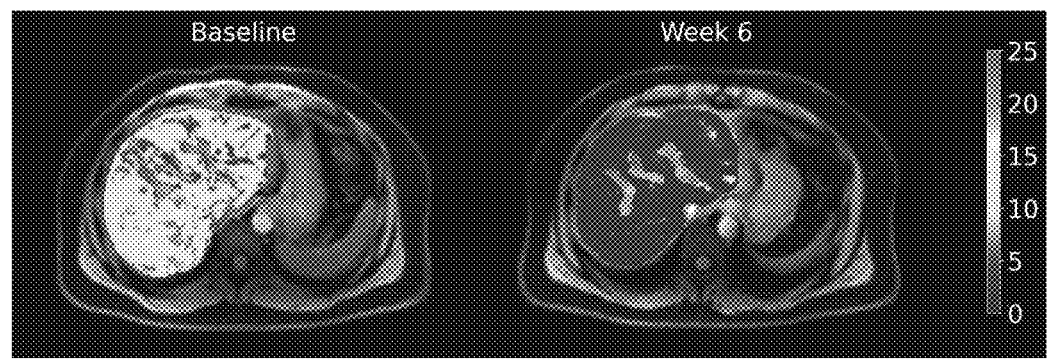
Figure 12:
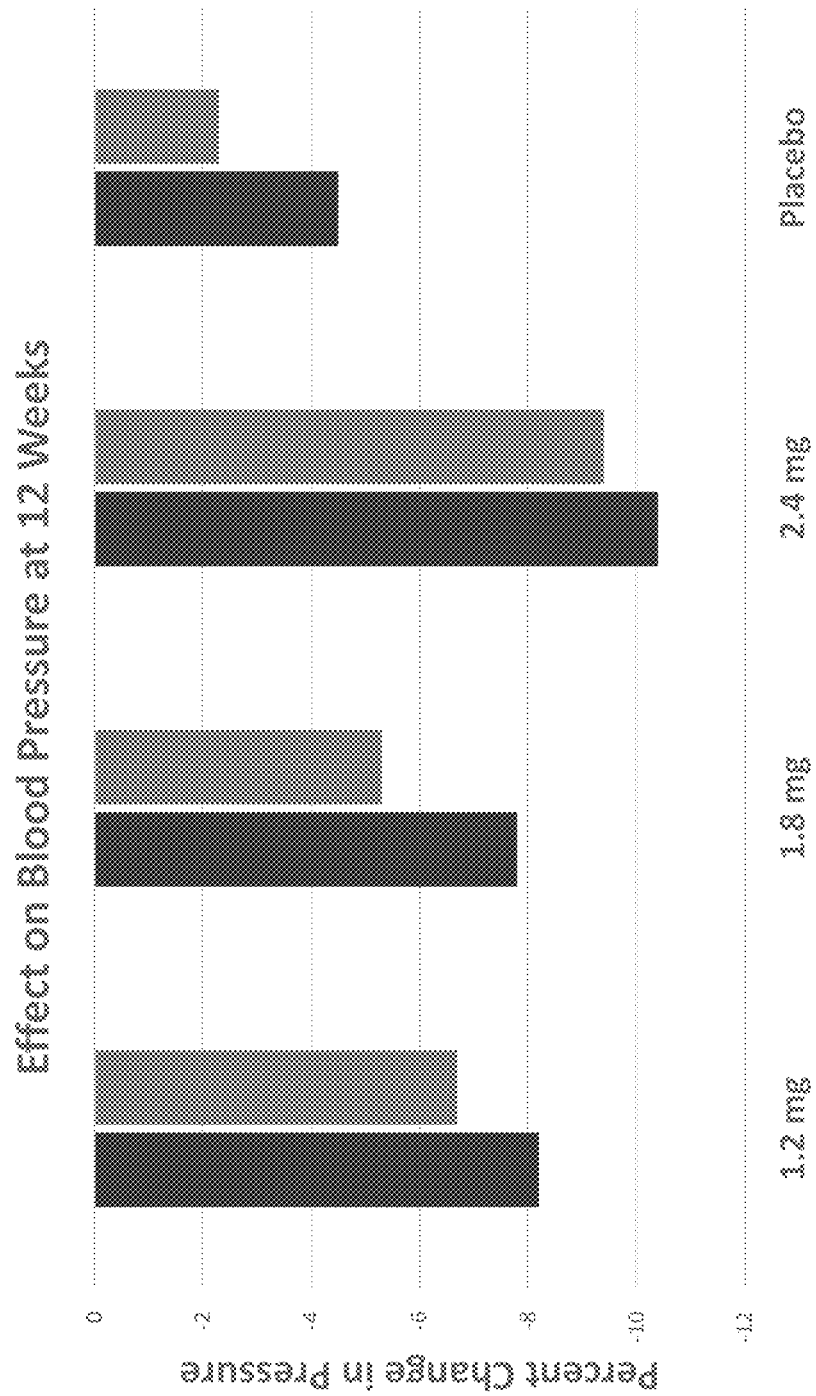
FIG. 12 illustrates improved blood pressure, as a biomarker for cardiovascular risk, in all groups following 12 week treatment with ALT-801 (1.2, 1.8 and 2.4 mg doses) as compared to placebo, wherein the first bar in each group is the systolic pressure and the second bar is the diastolic pressure. Weekly treatment with ALT-801 improved blood pressure across all dose groups (1.2 mg, 1.8 mg or 2.4 mg)
Figure 13:
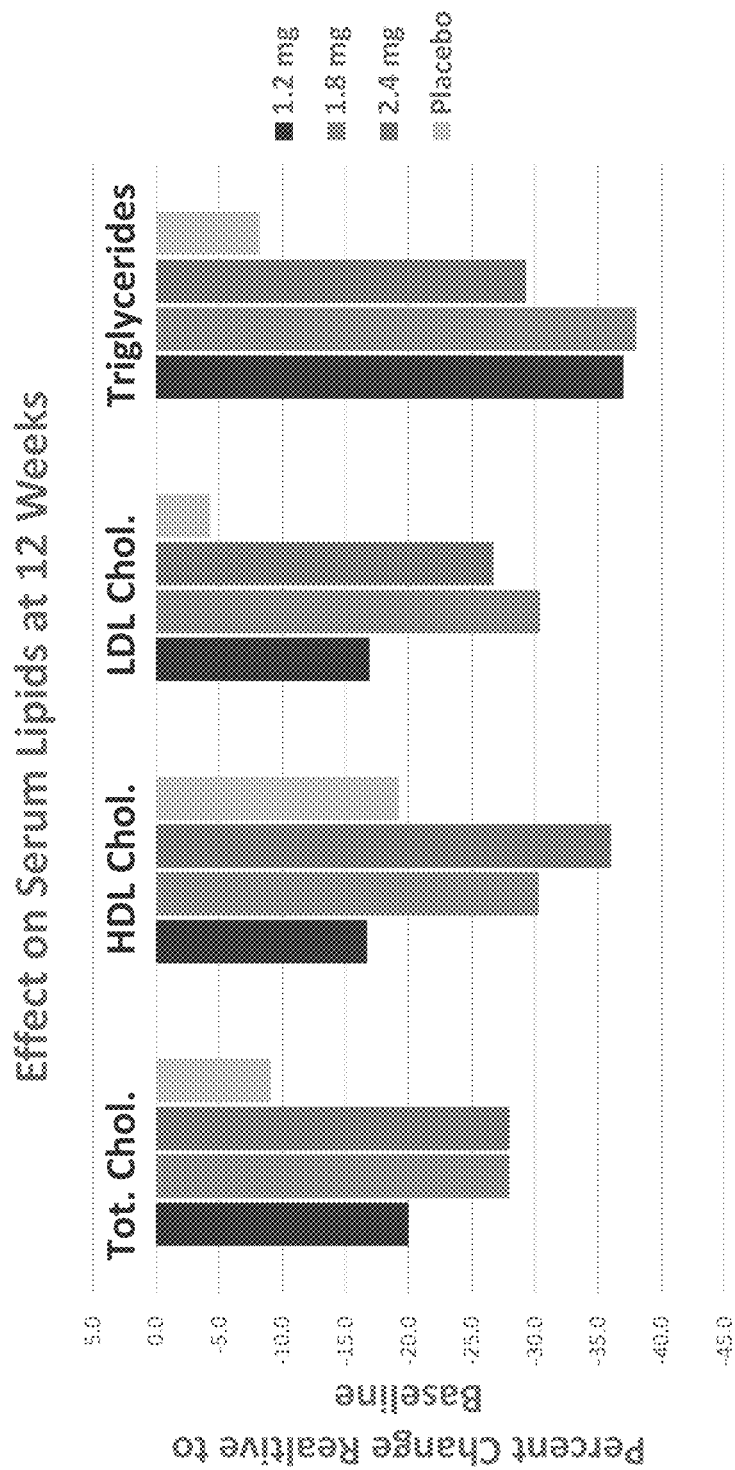
FIG. 13 illustrates improvements in serum lipid levels, as a biomarker of cardiovascular risk, (total cholesterol ("Tot. Chol."), high density lipoprotein ("HDL Chol."), low density lipoprotein ("LDL Chol."), and Triglycerides) across all dose groups (1.2, 1.8 and 2.4 mg doses) as compared to placebo following 12 weeks of treatment.

This example describes a study assessing the effects of ALT-801 on hepatic fat fraction in human subjects. Subjects who meet inclusion and do not meet exclusion criteria will be randomized 1:1:1:1 to one of the following treatment arms: 1) ALT-801 1.2 mg SC once weekly for 12 weeks; 2) ALT-801 1.8 mg SC once weekly for 12 weeks; 3) ALT-801 0.6 mg SC at week 1, 1.2 mg SC at week 2, 1.8 mg SC once weekly for 2 weeks (weeks 3 and 4), and 2.4 mg SC once weekly for weeks 5 through 12; or, Placebo (0.9% NaCl) subcutaneously (SC) once weekly for 12 weeks. The results are shown in Tables 19-23 (See also Tables 11 and 16-18 from previous example) and FIGS. 6-13. FIG. 6-8 present the data relating to all measurable subjects, and show liver fat reductions with no significant safety issues. FIGS. 9-10 present data related to steatosis subjects (those having fatty liver disease).

TABLE 19

Robust Changes in Liver Fat Content by MRI-PDFF*

| Treatment Group | Weight Loss (%) at Week 6 | MRI-PDFF (%) Baseline | MRI-PDFF (%) Week 6 | Absolute Δ at Week 6 (%) Individual | Absolute Δ at Week 6 (%) Mean | Relative Δ at Week 6 (%) Individual | Relative Δ at Week 6 (%) Mean |
|---|---|---|---|---|---|---|---|
| ALT-801 1.2 mg | 1.0 | 19.1 | 14.0 | 5.10 | 6.50 | 26.7 | 48.2 |
|  | 5.1 | 11.2 | 3.4 | 7.80 |  | 69.6 |  |
| ALT-801 1.8 mg | 4.4 | 12.4 | <LOD | 11.65 | 11.65 | 94.0 | 94.0 |
| ALT-801 2.4 mg | 3.7 | 17.0 | <LOD | 16.25 | 11.50 | 95.6 | 91.9 |
|  | 4.9 | 5.5 | <LOD | 4.75 |  | 86.4 |  |
|  | 3.1 | 7.0 | <LOD | 6.25 |  | 89.3 |  |
|  | 4.7 | 19.5 | <LOD | 18.75 |  | 96.2 |  |
| Placebo | 0.5 | 5.2 | 3.7 | 1.5 | 1.5 | 28.8 | 28.8 |

*LOD (limit of detection) = 1.5%; for absolute and relative change (Δ), values < LOD are set at 0.75%

TABLE 20

Changes in Liver Fat Content by MRI-PDFF at Week 6 (Individual Subjects)*

| Treatment Group | Weight Loss (%) at Week 6 | MRI-PDFF Baseline | MRI-PDFF Week 6 | Absolute Δ at Week 6 (%) Individual | Absolute Δ at Week 6 (%) Mean | Relative Δ at Week 6 (%) Individual | Relative Δ at Week 6 (%) Mean |
|---|---|---|---|---|---|---|---|
| Placebo | −2.1 | 1.8 | <LOD | 1.05 | 1.3 | 58.3 | 43.6 |
|  | 0.5 | 5.2 | 3.7 | 1.50 |  | 28.8 |  |
| ALT-801 1.2 mg | 2.5 | 2.7 | <LOD | 1.95 | 4.2 | 72.2 | 59.6 |
|  | 1.0 | 19.1 | 14.0 | 5.10 |  | 26.7 |  |
|  | 5.1 | 11.2 | 3.4 | 7.80 |  | 69.6 |  |
|  | 1.6 | 2.5 | <LOD | 1.75 |  | 70.0 |  |
| ALT-801 1.8 mg | 0.5 | 3.6 | <LOD | 2.85 | 4.6 | 79.2 | 77.8 |
|  | 3.7 | 3.7 | <LOD | 2.95 |  | 79.7 |  |
|  | 6.0 | 1.8 | <LOD | 1.05 |  | 58.3 |  |
|  | 4.4 | 12.4 | <LOD | 11.65 |  | 94.0 |  |
| ALT-801 2.4 mg | 3.7 | 17.0 | <LOD | 16.25 | 9.4 | 95.6 | 85.1 |
|  | 4.9 | 5.5 | <LOD | 4.75 |  | 86.4 |  |
|  | 3.1 | 7.0 | <LOD | 6.25 |  | 89.3 |  |
|  | 2.0 | 1.8 | <LOD | 1.05 |  | 58.3 |  |
|  | 4.7 | 19.5 | <LOD | 18.75 |  | 96.2 |  |

*LOD (limit of detection) = 1.5%; for absolute and relative change (Δ), values < LOD are set at 0.75%

TABLE 22

Safety Overview*

| Characteristic |  | 1.2 mg | 1.8 mg | 2.4 mg | Pooled placebo |
|---|---|---|---|---|---|
| AEs leading to discontinuation | n (%) | 0 (%) | 0 (%) | 0 (%) | 0 (%) |
| Serious or severe AEs | n (%) | 0 (%) | 0 (%) | 0 (%) | 0 (%) |
| Nausea |  |  |  |  |  |
| Mild | n (%) | 1 (14.3%) | 5 (55.6%) | 5 (45.5%) | 1 (14.3%) |
| Moderate | n (%) | 1 (14.3%) | 1 (11.1%) | 5 (45.5%) | 0 (0.0%) |
| Vomiting |  |  |  |  |  |
| Mild | n (%) | 1 (14.3%) | 1 (11.1%) | 5 (45.5%) | 1 (14.3%) |
| Moderate | n (%) | 0 (0.0%) | 1 (11.1%) | 3 (27.3%) | 0 (0.0%) |
| Diarrhea |  |  |  |  |  |
| Mild | n (%) | 0 (0.0%) | 0 (0.0%) | 2 (18.2%) | 0 (0.0%) |
| Moderate | n (%) | 0 (0.0%) | 0 (0.0%) | 0 (0.0%) | 0 (0.0%) |

TABLE 22-continued

Safety Overview*

| Characteristic | | Treatment | | | |
|---|---|---|---|---|---|
| | | 1.2 mg | 1.8 mg | 2.4 mg | Pooled placebo |
| Constipation | | | | | |
| Mild | n (%) | 0 (0.0%) | 1 (11.1%) | 2 (18.2%) | 0 (0.0%) |
| Moderate | n (%) | 0 (0.0%) | 1 (11.1%) | 1 (9.1%) | 0 (0.0%) |
| Hyperglycemia | n (%) | 0 (0.0%) | 0 (0.0%) | 0 (0.0%) | 0 (0.0%) |

*One subject receiving the 1.8 mg dose and one receiving placebo experienced 3-5 times ALT elevations with subsequent resolutions. Most frequently mild at 1.8 mg dose with on-drug resolution and not requiring treatment. No study discontinuations due to adverse events (AEs).

TABLE 23

Ketone Body Production

| Characteristic | | Treatment | | | |
|---|---|---|---|---|---|
| | | 1.2 mg | 1.8 mg | 2.4 mg | Pooled placebo |
| | | Ketone Bodies | | | |
| Baseline (mmol/L) | Mean (SD) | 0.12 (0.05) | 0.07 (0.04) | 0.10 (0.04) | 0.07 (0.02) |
| Week 12 (mmol/L) | Mean (SD) | 0.34 (0.57) | 0.52 (0.62) | 0.42 (0.21) | 0.20 (0.20) |

As shown above, robust changes (mean relative change of greater than 90%) in liver fat content as determined by MRI-PDFF in subjects with MRI-PDFF≥5% at baseline following six weeks of treatment with ALT-801 at 1.8 and 2.4 mg. Mean weight losses at Week 6 were 1.8%, 5.4%, and 4.7% at ALT-801 1.2 mg, 1.8 and 2.4 mg, respectively, with a mean weight gain of 0.9% in placebos. The results of this trial show that ALT-801 reduced liver fat in the subjects, including those having steatosis (fatty liver disease). The PK profile confirmed weekly dosing as appropriate. Blood pressure and serum lipid levels also improved among all groups. Glucose homeostasis was maintained. Ketone body production, an indicator of increased fat burn (an expected glucagon effect) was also improved.

Other advantages of the reagents and methods of using the same are also provided herein, as would be understood by those of ordinary skill in the art. While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A method for reducing body weight of a human being in need thereof comprising administering to the human being a once weekly therapeutic effective amount of a pharmaceutical dosage formulation comprising SEQ ID NO: 1 for at least 12 weeks.

2. The method of claim 1, wherein the method induces liver fat loss.

3. The method of claim 1, wherein the method is a treatment for blood glucose control.

4. The method of claim 1, wherein the method does not comprise a treatment initiation phase to titrate a therapeutic dose of the pharmaceutical dosage formulation.

5. The method of claim 1, wherein the method is an adjunct treatment with diet and/or exercise.

6. The method of claim 1 wherein the pharmaceutical dosage is administered on about days 1, 8, 15, 22, 29, and 36.

7. The method of claim 1, wherein the pharmaceutical dosage formulation is administered subcutaneously.

8. The method of claim 1, wherein the pharmaceutical dosage is an aqueous formulation comprising one or more of polysorbate 20, arginine, or mannitol.

9. The method of claim 1, wherein the pharmaceutical dosage formulation comprises about 0.025-0.075% (w/w) polysorbate 20, about 0.2-0.5% (w/w) arginine, about 3-6% (w/w) mannitol in deionized water (pH 7.7±0.1); optionally about 0.050% (w/w) polysorbate 20, about 0.348% (w/w) arginine, about 4.260% (w/w) mannitol in deionized water (pH 7.7±0.1).

10. The method of claim 1, wherein the weight of the human being is reduced by at least 5% from baseline at week 12.

11. A method for reducing body weight of a human being with a body mass index (BMI kg/m2) of at least 25 comprising administering to the human being a once weekly therapeutic effective amount of a pharmaceutical dosage formulation comprising SEQ ID NO: 1, wherein the weight of the human being is reduced by at least 5% from baseline at week 12.

12. The method of claim 11, wherein the weight of the human being is reduced by at least 6% from baseline at week 12; by at least 7% from baseline at week 12; by at least 8% from baseline at week 12; by at least 9% from baseline at week 12 or by at by at least 10% from baseline at week 12.

13. The method of claim 11, wherein the treatment is an adjunct treatment with increased physical activity and/or a reduced calorie diet.

14. The method of claim 11, wherein the treatment is not in combination with increased physical activity and/or a reduced calorie diet.

15. The method of claim 11, wherein the BMI of the human being is at least 30 kg/m2.

16. The method of claim 11, wherein the human being at week 0 is non-diabetic.

17. The method of claim 11, wherein the pharmaceutical dosage formulation is administered subcutaneously to the human being.

18. The method of claim 11, wherein the pharmaceutical dosage formulation is administered to the human being once per week for at least six weeks and results in at least about 3% whole-body weight loss.

19. The method of claim 11, wherein liver fat is reduced.

* * * * *

SEQUENCE LISTING

```
<160> NUMBER OF SEQ ID NOS: 11

<210> SEQ ID NO 1
<211> LENGTH: 30
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: SITE
<222> LOCATION: (16)..(20)
<223> OTHER INFORMATION: cyclic
<220> FEATURE:
<221> NAME/KEY: MOD_RES
<222> LOCATION: (17)..(17)
<223> OTHER INFORMATION: Z17CO2H
<220> FEATURE:
<221> NAME/KEY: SITE
<222> LOCATION: (20)..(20)
```

-continued

```
<223> OTHER INFORMATION: Lys side chain lactam linkage to Glu
<220> FEATURE:
<221> NAME/KEY: MOD_RES
<222> LOCATION: (30)..(30)
<223> OTHER INFORMATION: NH2

<400> SEQUENCE: 1

His Xaa Gln Gly Thr Phe Thr Ser Asp Tyr Ser Lys Tyr Leu Asp Glu
1               5                   10                  15

Lys Ala Ala Lys Glu Phe Ile Gln Trp Leu Leu Gln Thr Xaa
            20                  25                  30

<210> SEQ ID NO 2
<211> LENGTH: 30
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: SITE
<222> LOCATION: (16)..(20)
<223> OTHER INFORMATION: cyclic
<220> FEATURE:
<221> NAME/KEY: MOD_RES
<222> LOCATION: (17)..(17)
<223> OTHER INFORMATION: Me15CO2H
<220> FEATURE:
<221> NAME/KEY: SITE
<222> LOCATION: (20)..(20)
<223> OTHER INFORMATION: Lys side chain lactam linkage to Glu
<220> FEATURE:
<221> NAME/KEY: MOD_RES
<222> LOCATION: (30)..(30)
<223> OTHER INFORMATION: NH2

<400> SEQUENCE: 2

His Xaa Gln Gly Thr Phe Thr Ser Asp Tyr Ser Lys Tyr Leu Asp Glu
1               5                   10                  15

Lys Ala Ala Lys Glu Phe Ile Gln Trp Leu Leu Gln Thr Xaa
            20                  25                  30

<210> SEQ ID NO 3
<211> LENGTH: 30
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: SITE
<222> LOCATION: (16)..(20)
<223> OTHER INFORMATION: cyclic
<220> FEATURE:
<221> NAME/KEY: SITE
<222> LOCATION: (20)..(20)
<223> OTHER INFORMATION: Lys side chain lactam linkage to Glu
<220> FEATURE:
<221> NAME/KEY: MOD_RES
```

```
<222> LOCATION: (24)..(24)
<223> OTHER INFORMATION: Z15CO2H
<220> FEATURE:
<221> NAME/KEY: MOD_RES
<222> LOCATION: (30)..(30)
<223> OTHER INFORMATION: NH2

<400> SEQUENCE: 3

His Xaa Gln Gly Thr Phe Thr Ser Asp Tyr Ser Lys Tyr Leu Asp Glu
1               5                   10                  15

Gln Ala Ala Lys Glu Phe Ile Lys Trp Leu Leu Gln Thr Xaa
            20                  25                  30

<210> SEQ ID NO 4
<211> LENGTH: 30
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: SITE
<222> LOCATION: (16)..(20)
<223> OTHER INFORMATION: cyclic
<220> FEATURE:
<221> NAME/KEY: SITE
<222> LOCATION: (20)..(20)
<223> OTHER INFORMATION: Lys side chain lactam linkage to Glu
<220> FEATURE:
<221> NAME/KEY: MOD_RES
<222> LOCATION: (24)..(24)
<223> OTHER INFORMATION: Z17CO2H
<220> FEATURE:
<221> NAME/KEY: MOD_RES
<222> LOCATION: (30)..(30)
<223> OTHER INFORMATION: NH2

<400> SEQUENCE: 4

His Xaa Gln Gly Thr Phe Thr Ser Asp Tyr Ser Lys Tyr Leu Asp Glu
1               5                   10                  15

Gln Ala Ala Lys Glu Phe Ile Lys Trp Leu Leu Gln Thr Xaa
            20                  25                  30

<210> SEQ ID NO 5
<211> LENGTH: 30
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: SITE
<222> LOCATION: (16)..(20)
<223> OTHER INFORMATION: cyclic
<220> FEATURE:
<221> NAME/KEY: MOD_RES
<222> LOCATION: (17)..(17)
<223> OTHER INFORMATION: Z17CO2H
<220> FEATURE:
```

```
<221> NAME/KEY: SITE
<222> LOCATION: (20)..(20)
<223> OTHER INFORMATION: Lys side chain lactam linkage to Glu
<220> FEATURE:
<221> NAME/KEY: MOD_RES
<222> LOCATION: (30)..(30)
<223> OTHER INFORMATION: NH2

<400> SEQUENCE: 5

His Xaa Gln Gly Thr Phe Thr Ser Asp Tyr Ser Arg Tyr Leu Asp Glu
1               5                   10                  15

Lys Ala Ala Lys Glu Phe Ile Gln Trp Leu Leu Gln Thr Xaa
            20                  25                  30

<210> SEQ ID NO 6
<211> LENGTH: 29
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(20)
<223> OTHER INFORMATION: cyclic
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: MOD_RES
<222> LOCATION: (17)..(17)
<223> OTHER INFORMATION: Lys(N-omega(1-(17-carboxyl-heptadecyloxy)beta-
      D-glucuronyl)) or Lys(Z17CO2H)
<220> FEATURE:
<221> NAME/KEY: SITE
<222> LOCATION: (20)..(20)
<223> OTHER INFORMATION: Lys side chain lactam linkage to Glu

<400> SEQUENCE: 6

His Xaa Gln Gly Thr Phe Thr Ser Asp Tyr Ser Lys Tyr Leu Asp Glu
1               5                   10                  15

Xaa Ala Ala Lys Glu Phe Ile Gln Trp Leu Leu Gln Thr
            20                  25

<210> SEQ ID NO 7
<211> LENGTH: 29
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(20)
<223> OTHER INFORMATION: cyclic
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: MOD_RES
<222> LOCATION: (17)..(17)
<223> OTHER INFORMATION: Me17CO2H
<220> FEATURE:
<221> NAME/KEY: SITE
<222> LOCATION: (20)..(20)
```

<223> OTHER INFORMATION: Lys side chain lactam linkage to Glu

<400> SEQUENCE: 7

His Xaa Gln Gly Thr Phe Thr Ser Asp Tyr Ser Lys Tyr Leu Asp Glu
1               5                   10                  15

Xaa Ala Ala Lys Glu Phe Ile Gln Trp Leu Leu Gln Thr
            20                  25

<210> SEQ ID NO 8
<211> LENGTH: 29
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(20)
<223> OTHER INFORMATION: cyclic
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: SITE
<222> LOCATION: (20)..(20)
<223> OTHER INFORMATION: Lys side chain lactam linkage to Glu
<220> FEATURE:
<221> NAME/KEY: MOD_RES
<222> LOCATION: (24)..(24)
<223> OTHER INFORMATION: Lys(Z15CO2H)

<400> SEQUENCE: 8

His Xaa Gln Gly Thr Phe Thr Ser Asp Tyr Ser Lys Tyr Leu Asp Glu
1               5                   10                  15

Gln Ala Ala Lys Glu Phe Ile Xaa Trp Leu Leu Gln Thr
            20                  25

<210> SEQ ID NO 9
<211> LENGTH: 29
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (16)..(20)
<223> OTHER INFORMATION: cyclic
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: SITE
<222> LOCATION: (20)..(20)
<223> OTHER INFORMATION: Lys side chain lactam linkage to Glu
<220> FEATURE:
<221> NAME/KEY: MOD_RES
<222> LOCATION: (24)..(24)
<223> OTHER INFORMATION: Lys(Z17CO2H)

<400> SEQUENCE: 9

His Xaa Gln Gly Thr Phe Thr Ser Asp Tyr Ser Lys Tyr Leu Asp Glu
1               5                   10                  15

```
Gln Ala Ala Lys Glu Phe Ile Xaa Trp Leu Leu Gln Thr
            20                  25
```

```
<210> SEQ ID NO 10
<211> LENGTH: 29
<212> TYPE: PRT
<213> ORGANISM: Artificial squence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(12)
<223> OTHER INFORMATION: Arg
<220> FEATURE:
<221> NAME/KEY: SITE
<222> LOCATION: (16)..(20)
<223> OTHER INFORMATION: cyclic
<220> FEATURE:
<221> NAME/KEY: SITE
<222> LOCATION: (16)..(16)
<223> OTHER INFORMATION: Glu side chain lactam linkage to Lys
<220> FEATURE:
<221> NAME/KEY: MOD_RES
<222> LOCATION: (17)..(17)
<223> OTHER INFORMATION: Lys(N-omega(1-(17-carboxyl-heptadecyloxy)beta-
      D-glucuronyl)) or Lys(Z17CO2H)
<220> FEATURE:
<221> NAME/KEY: SITE
<222> LOCATION: (20)..(20)
<223> OTHER INFORMATION: Lys side chain lactam linkage to Glu

<400> SEQUENCE: 10

His Xaa Gln Gly Thr Phe Thr Ser Asp Tyr Ser Xaa Tyr Leu Asp Glu
1               5                   10                  15

Xaa Ala Ala Lys Glu Phe Ile Gln Trp Leu Leu Gln Thr
            20                  25
```

```
<210> SEQ ID NO 11
<211> LENGTH: 31
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Lys(yGlu-2xOEG)

<400> SEQUENCE: 11

His Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30
```